United States Patent
Srinivasan et al.

(10) Patent No.: US 11,134,868 B2
(45) Date of Patent: Oct. 5, 2021

(54) METAL PILLAR DEVICE STRUCTURES AND METHODS FOR MAKING AND USING THEM IN ELECTROCHEMICAL AND/OR ELECTROCATALYTIC APPLICATIONS

(71) Applicant: MEDTRONIC MINIMED, INC., Northridge, CA (US)

(72) Inventors: Akhil Srinivasan, Sherman Oaks, CA (US); Melissa Tsang, Lansdowne, PA (US); Robert C. Mucic, Glendale, CA (US); Tyler R. Wong, Pasadena, CA (US); Rui Kong, Northridge, CA (US); Barry P. Pham, Burbank, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 307 days.

(21) Appl. No.: 15/922,718

(22) Filed: Mar. 15, 2018

(65) Prior Publication Data

US 2019/0008425 A1 Jan. 10, 2019

Related U.S. Application Data

(60) Provisional application No. 62/472,712, filed on Mar. 17, 2017.

(51) Int. Cl.
*A61B 5/145* (2006.01)
*A61B 5/1486* (2006.01)
(Continued)

(52) U.S. Cl.
CPC ...... *A61B 5/14532* (2013.01); *A61B 5/14865* (2013.01); *B81B 3/0021* (2013.01);
(Continued)

(58) Field of Classification Search
CPC ............... C12Q 1/006; G01N 27/3278; G01N 27/3272; B81B 2203/0361; B81B 3/0021;
(Continued)

(56) References Cited

U.S. PATENT DOCUMENTS

| | | | |
|---|---|---|---|
| 4,755,173 A | 7/1988 | Konopka et al. | |
| 5,391,250 A | 2/1995 | Cheney, II et al. | |

(Continued)

FOREIGN PATENT DOCUMENTS

| | | |
|---|---|---|
| CN | 102556952 | 1/2015 |
| WO | 2013168956 | 11/2013 |

OTHER PUBLICATIONS

Angel Barranco, Ana Borras, Agustin R. Gonzalez-Elipe, Alberto Palmero, Progress in Materials Science pp. 59-153. "Perspectives on oblique angle depositon of thin films: From fundamentals to devices." Available online Aug. 28, 2015. (Year: 2015).*

(Continued)

*Primary Examiner* — Devin B Henson
*Assistant Examiner* — Joseph A Tombers
(74) *Attorney, Agent, or Firm* — Gates & Cooper LLP

(57) ABSTRACT

The invention disclosed herein includes electrode compositions formed from processes that sputter metal in a manner that produces pillar architectures. Embodiments of the invention can be used in analyte sensors having such electrode architectures as well as methods for making and using these sensor electrodes. A number of working embodiments of the invention are shown to be useful in amperometric glucose sensors worn by diabetic individuals. However, the metal pillar structures have wide ranging applicability and should increase surface area and decrease charge density for catalyst layers or electrodes used with sensing, power generation, recording, and stimulation, in vitro and/or in the body, or outside the body.

15 Claims, 80 Drawing Sheets

(51) Int. Cl.
*C12Q 1/00* (2006.01)
*B81B 3/00* (2006.01)
*G01N 27/327* (2006.01)
*C23C 14/34* (2006.01)

(52) U.S. Cl.
CPC ......... *C12Q 1/006* (2013.01); *G01N 27/3278* (2013.01); *A61B 2562/0209* (2013.01); *A61B 2562/125* (2013.01); *B81B 2203/0361* (2013.01); *C23C 14/3442* (2013.01); *G01N 27/3272* (2013.01)

(58) Field of Classification Search
CPC ............ C23C 14/3442; A61B 5/14532; A61B 5/14865; A61B 2562/0209; A61B 2562/125
See application file for complete search history.

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2002/0013006 A1 | 1/2002 | Miki et al. |
| 2005/0260453 A1* | 11/2005 | Jiao ........................ B82Y 40/00 428/698 |
| 2007/0123819 A1 | 5/2007 | Mernoe et al. |
| 2010/0066346 A1 | 3/2010 | Zhang et al. |
| 2010/0160861 A1 | 6/2010 | Causey, III et al. |
| 2011/0042237 A1* | 2/2011 | Fukuda .................. G01N 27/27 205/775 |
| 2012/0091586 A1* | 4/2012 | Ginley .................. C23C 14/046 257/741 |
| 2012/0190950 A1* | 7/2012 | Yang ...................... C12Q 1/001 600/345 |
| 2013/0066182 A1* | 3/2013 | Seymour .................. A61B 5/68 600/377 |
| 2014/0228660 A1* | 8/2014 | Mujeeb-U-Rahman ..................... A61B 5/14532 600/345 |
| 2018/0338681 A1 | 11/2018 | Scherer et al. |
| 2019/0008425 A1 | 1/2019 | Srinivasan et al. |

OTHER PUBLICATIONS

PCT International Search Report & Written Opinion dated Aug. 22, 2018, International Application No. PCT/US18/22805.
Canadian Office Action dated Dec. 15, 2020 for Canadian Application No. 3,056,105.
PCT International Search Report & Written Opinion dated Oct. 2, 2020 for PCT Application No. PCT/US2020/043971.

* cited by examiner

Regions shaded in blue, green, and red correspond to counter, working, and reference electrode sites, respectively

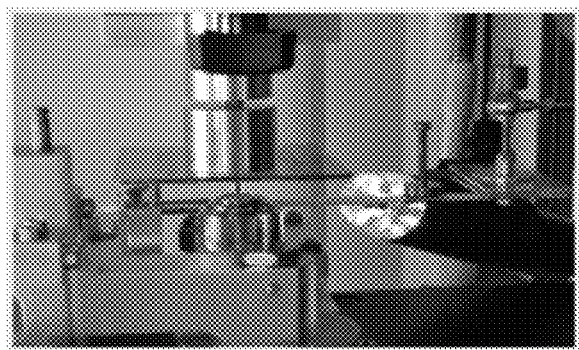
FIG. 45C
FIG. 45B
FIG. 45A

Plate3

Plate4

Plate5

Sensor2-Electrode2

Sensor7-Electrode2

Sensor6-Electrode2

Sensor11-Electrode2

Results comparing scratch testing Plate1, Plate2, Plate3, Plate4, Plate5, and Plate6

Results for scratch testing Plate 1

| | | |
|---|---|---|
| | | 7.36 |
| | | 7.07 |
| | | 58.02 |
| | | 8.17 |
| Min. | | 7.28 |
| Max. | | 69.05 |
| Avg. | | 28.05 |
| STDEV | | 26.71 |

FIG. 52A

Results for scratch testing Plate 2

| | | |
|---|---|---|
| | | 19.02 |
| | | 6.72 |
| | | 7.83 |
| | | 20.24 |
| Min. | | 7.83 |
| Max. | | 20.24 |
| Avg. | | 13.70 |
| STDEV | | 6.34 |

| | | |
|---|---|---|
| 2.3 | | 160.16 |
| 6.3 | | 61.28 |
| 7.3 | | 53.86 |
| 11.3 | | 164.67 |
| Min. | 53.86 | |
| Max. | 164.67 | |
| Avg. | 107.44 | |
| STDEV | 58.99 | |

| 2.3 | | 44.32 |
| 6.3 | | 17.69 |
| 7.3 | | 15.41 |
| 11.3 | | 48.74 |
| Min. | | 15.43 |
| Max. | | 48.74 |
| Avg. | | 31.54 |
| STDEV | | 17.43 |

FIG. 52B

Results for scratch testing Plate 3

| | | |
|---|---|---|
| 2.2 | | 64.14 |
| 6.2 | | 56.27 |
| 7.2 | | 47.51 |
| 11.2 | | 142.93 |
| Min. | | 47.51 |
| Max. | | 142.93 |
| Avg. | | 77.71 |
| STDEV | | 44.93 |

| 2.2 | | 38.54 |
| 6.2 | | 18.03 |
| 7.2 | | 18.54 |
| 11.2 | | 42.21 |
| Min. | | 18.54 |
| Max. | | 42.21 |
| Avg. | | 29.83 |
| STDEV | | 13.22 |

FIG. 52C

Results for scratch testing Plate 4

| | | |
|---|---|---|
| 2.2 | | 25.53 |
| 6.2 | | 33.14 |
| 7.2 | | 33.25 |
| 11.2 | | 38.57 |
| Min. | | 25.53 |
| Max. | | 35.98 |
| Avg. | | 33.07 |
| STDEV | | 2.38 |

| 2.2 | | 9.41 |
| 6.2 | | 8.03 |
| 7.2 | | 4.66 |
| 11.2 | | 19.98 |
| Min. | | 4.66 |
| Max. | | 19.98 |
| Avg. | | 10.53 |
| STDEV | | 6.61 |

| 2.2 | | 9.93 |
| 6.2 | | 8.57 |
| 7.2 | | 6.8 |
| 11.2 | | 9.6 |
| Min. | | 6.67 |
| Max. | | 9.93 |
| Avg. | | 9.24 |
| STDEV | | 0.66 |

FIG. 52D

Continue.......Results comparing scratch testing Plate1, Plate2, Plate3, Plate4, Plate5, and Plate6

Results for scratch testing Plate5

| Sample Finish Number | Distance to first Delamination (mm) | Load at First Delamination (lbs) | Feed at First Delamination (lbs) (Normalized Load Resistance) |
|---|---|---|---|
| 2.2 | 123.55 | 36.4 | 10.73 |
| 6.2 | 53.72 | 9.66 | 3.28 |
| 7.2 | 30.41 | 8.43 | 3.49 |
| 11.2 | 69.13 | 24.27 | 6.47 |
| Min. | 30.41 | 8.43 | 3.28 |
| Max | 123.55 | 36.40 | 10.73 |
| Avg. | 67.70 | 19.69 | 5.99 |
| STDEV | 44.36 | 13.26 | 3.48 |

FIG. 53A

Results for scratch testing Plate6

| Sample Finish Number | Distance to first Delamination (mm) | Load at First Delamination (lbs) | Feed at First Delamination (lbs) (Normalized Load Resistance) |
|---|---|---|---|
| 2.2 | 31.16 | 8.65 | 2.37 |
| 6.2 | 28.82 | 7.95 | 3.56 |
| 7.2 | 25.08 | 6.81 | 2.46 |
| 11.2 | 27.70 | 7.86 | 2.54 |
| Min. | 25.09 | 6.81 | 2.37 |
| Max | 31.16 | 8.65 | 3.56 |
| Avg. | 28.19 | 7.82 | 2.73 |
| STDEV | 2.52 | 0.76 | 0.56 |

FIG. 53B

METAL PILLAR DEVICE STRUCTURES AND METHODS FOR MAKING AND USING THEM IN ELECTROCHEMICAL AND/OR ELECTROCATALYTIC APPLICATIONS

CROSS-REFERENCE TO RELATED APPLICATIONS

This application claims the benefit under 35 U.S.C. Section 119(e) of U.S. Provisional Application Ser. No. 62/472,712, filed on Mar. 17, 2017, by Akhil Srinivasan, Melissa Tsang, Robert C. Mucic, Tyler R. Wong, Rui Kong, and Barry P. Pham, entitled "METAL PILLAR DEVICE STRUCTURES AND METHODS FOR MAKING AND USING THEM IN ELECTROCHEMICAL AND/OR ELECTROCATALYTIC APPLICATIONS," which application is incorporated by reference herein.

TECHNICAL FIELD

The invention relates to electrode compositions useful in devices such as glucose sensors used in the management of diabetes.

BACKGROUND OF THE INVENTION

Electrochemical sensors are commonly used to detect or measure the concentrations of in vivo analytes, such as glucose. Typically in such analyte sensing systems, an analyte (or a species derived from it) is electro-active and generates a detectable signal at an electrode in the sensor. This signal is then correlated with the presence or concentration of the analyte within a biological sample. In some conventional sensors, an enzyme is provided that reacts with the analyte to be measured, the byproduct of the reaction being qualified or quantified at the electrode. In one conventional glucose sensor, immobilized glucose oxidase catalyzes the oxidation of glucose to form hydrogen peroxide, which is then quantified by amperometric measurements (e.g. change in electrical current) through one or more electrodes.

A variety of electrochemical glucose sensors are multi-layered, comprising electrodes on top of and/or coated by layers of various materials. Multilayered sensors have a number of desirable properties including the fact that the functional properties of such sensors can be tailored by altering certain design parameters (e.g. number of internal layers, layer thickness, electrodes area and architecture etc). The fabrication of such multilayered sensors can require complicated processes steps that, for example, ensure that the various material layers exhibit appropriate functional characteristics, are of a uniform consistency, and are adapted to adhere to the group of materials that make up a stable sensor stack. In this context, certain electroplating processes can result in plated electrodes having a non-uniform surface, for example one that exhibits excessive growth at electrode edges. This edge growth can then cause non-uniformity in the subsequent layers of materials that are coated onto such electrodes, a phenomena which appears to contribute to certain undesirable glucose sensor phenomena, including layer delamination, sensor signal variability and high oxygen responses.

There is a need for methods and materials that can provide multilayered amperometric sensors with a number of desirable characteristics such as stability and optimized oxygen responses as well as improved manufacturing processes for fabricating such sensors.

SUMMARY OF THE INVENTION

A process has been developed to create metal (e.g. platinum) on the surface of an electrode to form an electroactive architecture which shows at least comparable (if not superior) performance to electroplated platinum for the purposes of increasing surface area of an electrode without increasing the geometric area of the electrode. Not only does the sputtering process achieve desirable performance, but the process developed is also significantly more controllable and efficient compared to the process of electroplating allowing significant manufacturing cost savings. The process that has been developed is easily transferable to multiple sensor and substrate designs, including wafer, square glass plate, and sheet and Roll-to-Roll processing. In one embodiment, the metal (e.g. Pt) pillar architectures are patterned using conventional photolithography and liftoff processes, enabling high throughput, reclamation of residual metal, outsourcing of the processing, and easy transfer between plates and a wafer. Moreover, the processes and designs detailed here are not only specific to platinum but apply to all sputtered materials where rough or high surface area designs may be advantageous.

The invention disclosed herein includes electrodes formed from sputtering processes that produce highly desirable electrode morphologies including a pillar structures having a selected architecture. In one or more embodiments of the invention, the pillars form an electroactive surface of an electrode, comprise a metal composition, have a height of not more than 10 micrometers and have a diameter in a range of 1 nanometer (nm)-1000 nm. In some embodiments, the pillars have a height in a range of 500 nm-4 micrometers and a diameter of 50 nm-200 nm. In other embodiments, the pillars have a height in a range of 2 micrometers-4 micrometers and a diameter of 100 nm-900 nm. In one or more examples, the heights of the pillars do not vary by more than 25% or 10% and/or the electroactive surface has a SAR in a range of 0-500.

In illustrative embodiments of the invention, the sputtering processes disclosed herein can be used to produce electrodes having a number of desirable material properties that make them well suited for use in amperometric glucose sensors that are worn by diabetic individuals. One embodiment of the invention comprises a method of sensing an analyte within the body of a mammal (e.g. a human diagnosed with Type I diabetes). Typically, this method comprises implanting an analyte sensor having sputtered electrodes disclosed herein within the mammal (e.g. in the interstitial space of a diabetic individual), sensing an alteration in current at the working electrode in the presence of the analyte; and then correlating the alteration in current with the presence of the analyte, so that the analyte is sensed.

However, importantly, this design and process is applicable to not only glucose sensors but metal electrodes used in a variety of contexts, for example those where surface area and charge density are important utility/design criteria. Examples include, but are not limited to, cardiac leads and neural electrodes. Furthermore, the sputtered metal pillar design is also applicable to electrodes and applications other than electrodes used in the body and/or in-vitro (e.g., applications including electrocatalysis, electrochemistry, batteries, fuel cells, solar cells, stimulation/recording (charge transfer)), where controllable or high surface area is advantageous or required. In one or more embodiments, the pillar structures are disposed in multi electrode arrays, such as micro-electrode arrays.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 1A illustrates the advantages of smooth and porous Pt structures as an electrocatalytic material conventionally used as a WE or CE electrode, wherein current output in a sensor proportional to active surface area and high surface area ensures reaction limited conditions.

As shown in FIG. 4, a potentiostat 300 may include an op amp 310 that is connected in an electrical circuit so as to have two inputs: Vset and Vmeasured. As shown, Vmeasured is the measured value of the voltage between a reference electrode (RE) and a working electrode (WE). Vset, on the other hand, is the optimally desired voltage across the working and reference electrodes. The current between the counter and reference electrode is measured, creating a current measurement (isig) that is output from the potentiostat.

FIG. 13D is a zoomed view of FIG. 13C.

FIG. 17A-17B are SEM images of the Pt pillars on the CE electrode, wherein FIG. 17A is a cross sectional view and FIG. 17B is a top view of the indicated area in FIG. 17A.

FIGS. 35-38 present results of pig in-vivo experiments using sensors with Pt pillars as compared to electroplated Pt, wherein FIG. 35 shows data for sensors comprising Pt pillars with SAR=95 (Pi95) (number N of sensors=4 sensors), Pt pillars with SAR=250 (Pi250) (N=10 sensors), electroplated Pt with SAR=95 (Ep95) (N=4 sensors), and electroplated Pt with SAR=250 (Ep250) (N=10 sensors) over a period of days, FIG. 36 shows data for sensors comprising Pt pillars with SAR=250 (Pi250) and sensors comprising electroplated Pt with SAR=250 (Ep250), FIG. 37 shows data for sensors comprising Pt pillars with SAR=95 (Pi95) and sensors comprising electroplated Pt with SAR=95 (Ep95), and FIG. 38 shows data for sensors comprising Pt pillars with SAR=95 (Pi95), Pt pillars with SAR=250 (Pi250), electroplated Pt with SAR=95 (Ep95), and electroplated Pt with SAR=250 (Ep250) over a period of hours on day 1.

FIGS. 39-43 are images of a novel implementation of pillars below & before the manufacturing process for the polyimide insulation layer in the sensors. Conventionally, the Pt pillars had been implemented above & after the manufacturing process for the polyimide insulation, wherein FIG. 39 and FIG. 40 are top view optical and scanning electron microscope (SEM) images, respectively, FIG. 41 is a close up top view, FIG. 42 is a close up side view, and FIG. 43 is a close up top and side view.

FIGS. 44-58B illustrate scratch testing of Pt Pillars, and present results on adhesion testing performed to measure adhesion until the point of failure of the Pt Pillars to the underlying gold electrode surface, wherein FIG. 44 shows electrode configuration, FIGS. 46A-51D are images of scratch testing for the indicated plates, sensors, and electrodes, FIG. 45A-45B illustrate an apparatus for scratch testing (FIG. 45B is a close up view of the indicated area in FIG. 45A), FIG. 45C illustrates parameters for scratch testing, FIGS. 52A-53B are tables comparing scratch testing of plates 1-6 illustrated in FIGS. 46A-51D, FIG. 54 is a variability chart for scratch distance to delamination, FIG. 55 is a variability chart for normal force at first delamination (newton meters nM), FIG. 56 is a variability chart for shear force at first delamination (nM), FIGS. 58A and 58B show the analysis of variance for scratch distance to first delamination when the data for plate 1 and outliers are left out, showing a clear grouping formed between the plates.

FIGS. 59-63 illustrate the same highly organized nano/micro pillar structures comprising gold (Au) instead of platinum (Pt), wherein FIGS. 59, 60, and 61 are top views of different magnification and FIGS. 62 and 63 are side view SEM images having different magnification and wherein a pillar height in FIG. 63 is 2.22 micrometers.

DETAILED DESCRIPTION OF THE INVENTION

Figure 1B:
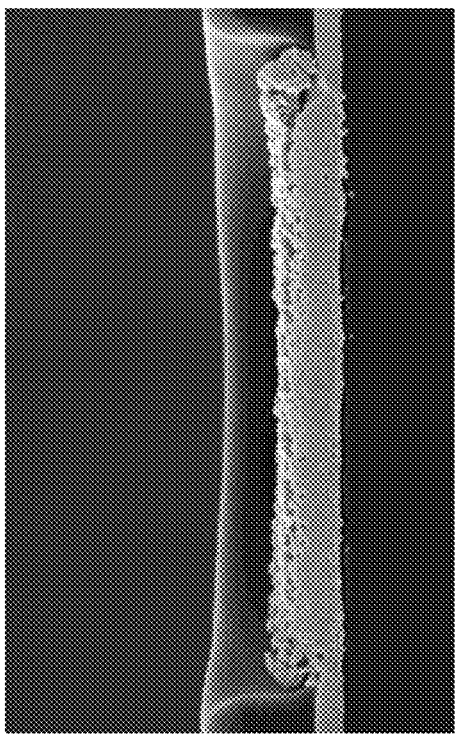
FIG. 1B and FIG. 1C are SEM images of electroplated Pt.

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All numbers recited in the specification and associated claims that refer to values that can be numerically characterized with a value other than a whole number (e.g. a thickness) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors elements, including for example, those disclosed in U.S. Patent Application Nos. 20050115832, 20050008671, 20070227907, 20400025238, 20110319734, 20110152654 and Ser. No. 13/707,400 filed Dec. 6, 2012, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042, 625, and WO 03/074107, and European Patent Application EP 1153571, the contents of each of which are incorporated herein by reference.

A. Illustrative Embodiments of the Invention and Associated Characteristics

Figure 1C:
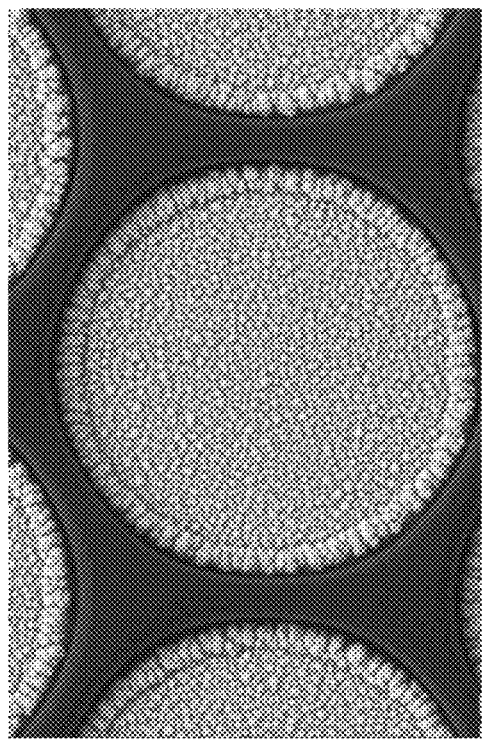
Figure 1A:
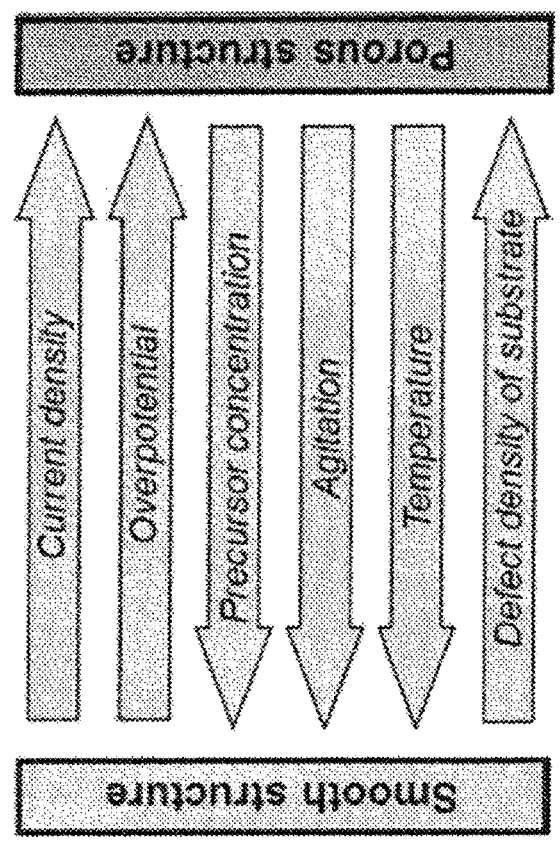
FIG. 1A illustrates the advantages of smooth and porous Pt structures.

The benefits of conventional electrodeposited Pt black electrodes include the potential for a high degree of design control, micro-patterning, and scalabilty. However, while conventional electrodeposition processes that use electroplating to form platinum black electrodes can produce electrodes having high active surface areas that are useful for electrochemical reactions, these processes can also produce electrodes having certain challenging features including significant edge growth (see, e.g. FIGS. 1B and 1C). The dendrite structures that form this edge growth can contribute to non-uniformity in subsequent layers of material that are coated into such electrodes (e.g. layer cracking, layer delamination and the like). Such non-uniformity in a plurality of layered sensor elements can contribute to certain undesirable phenomena such as sensor signal variability and high oxygen response.

In addition, electroplating sensor structures is a time consuming process, taking approximately 8 hours to fabricate 8 plates, costly (electroplating equipment and replenishing chemicals are expensive), and complex (patterning an 8" wafer requires control of circuit resistivity, yield due to ganging sensors, a complex processing, and requires challenging process control of the electroplating solution).

The sputtered pillar architecture disclosed herein, on the other hand, enables a more efficient electrode design than can be achieved using electroplating. For example, the pillar structures are easily transferable to 8" wafers and any sensor platform. Furthermore, the sputtering process enables elimination of additional processing required for scaling up. At the same time, the sputtering process deposits uniform films of Pt pillars achieving high surface areas normally achieved by electroplating Pt. Thus, the Pt pillars disclosed herein offer excellent design and process control for increasing the surface area of electrodes, and more efficient Pt design and utilization than electroplated Pt, realizing desirable performance at the same time as large cost reduction in Pt utilization (including reclaiming of residual Pt material), process simplification, and excellent repeatability.

In addition, the new sputtering process disclosed herein for depositing metal electrodes produces electrodes having electrochemically robust active surface areas and an electrochemical performance at least comparable to that formed in conventional plating processes. Indeed, with minimal optimization, sensors comprising the pillar structures exhibit performance comparable to nominal electroplated electrodes.

Thus, the sputtering processes disclosed herein produce metal compositions having material properties that made them very useful as electrodes in multilayered amperometric glucose sensors. For example, platinum electrode compositions produced by the sputtering processes are shown to exhibit electroactive surfaces having a number of desirable qualities that make them useful in devices such as glucose sensors. For example, when used in amperometric glucose oxidase based sensors, electrode structures comprising pillar architectures are observed to exhibit highly desirable oxygen response profiles. Specific to Diabetes, the pillar design and sputtering process enables sensor designs that will meet Harmony 2 and Harmony 3 requirements as well as enable the next generation NDT glucose sensor platform.

In certain embodiments of the invention, the sputtering process is selected to produce a metal layer having an average thickness between 1 µm and 20 µm (and typically about 1, 2, 3, 4, 5, 6, 7, 8, 9, or 10 µm) in the central planar region. In certain embodiments of the invention, the sputtering process produces a metal layer having an edge that is less than 15, 14, 13, 12, 11, 10, 9, 8, 7, 6 or 5 µm in thickness. In some embodiments, the top of the edge region rises less than about 7, 6, 5, 4, 3, 2 or 1 µm above the top of the central planar region. In certain embodiments of the invention, the average thickness of the metal layer in the edge region is less than 2×, 1.5× or 1× the average thickness of the metal layer not in the edge region (e.g. in the central planar region).

The methods for forming analyte sensors that comprise the electrodes disclosed herein can include a number of other steps. For example, such methods can include forming a working electrode, a counter electrode (CE) and a reference electrode (RE) on the base substrate and/or forming a plurality of contact pads on the base substrate, and/or forming a plurality of electrical conduits on the base substrate. In certain embodiments of the invention, the methods comprise forming a plurality of working electrodes, counter electrodes and reference electrodes clustered together in units consisting essentially of one working electrode, one counter electrode and one reference electrode are formed on the base substrate and these clustered units are longitudinally distributed on at least one longitudinal arm of the base substrate in a repeating pattern of units. Optionally in such methods, the working electrode is formed as an array of electrically conductive members disposed on the base substrate, the electrically conductive members are circular and have a diameter between 10 µm and 400 µm, and the array comprises at least 10 electrically conductive members. The methods can further comprise forming an analyte sensing layer on the working electrode, wherein the analyte sensing layer detectably alters the electrical current at the working electrode in the presence of an analyte. Typically these methods also include forming an analyte modulating layer on the analyte sensing layer, wherein the analyte modulating layer modulates the diffusion of analyte therethrough.

Yet another embodiment of the invention is an analyte sensor apparatus that includes a base substrate comprising a well that holds a metal electrode composition formed using the sputtering processes disclosed herein. In such embodiments, the structure of the platinum composition is formed to include a central planar region and an edge or ridge like region that surrounds the central planar region. In such embodiments, the thickness or height of the metal composition at the edge is less than 2× the average thickness of metal composition in the central planar region. In certain embodiments of the invention, the well comprises a lip that surrounds the well; and the edge region of the metal composition is below the lip of the well. Typically in these embodiments, both the central planar region forms an electroactive surface of a working electrode in the sensor. Sensor embodiments of the invention typically include additional layers of material coated over the working electrode, for example an analyte sensing layer disposed over the working electrode, one that detectably alters the electrical current at the working electrode in the presence of an analyte as well as an analyte modulating layer disposed over the analyte sensing layer that modulates the diffusion of analyte therethrough.

In typical embodiments of the invention, the electrode is formed in a well of a base substrate comprising a dielectric material (e.g. a polyimide). Typically, the well includes a conductive material disposed at the bottom of the well (e.g. Au). Optionally the well in the base substrate is rectangular or circular. In certain embodiments of the invention, the base substrate comprises at least 10, 20 or 30 wells formed into a microarray. In typical sensor embodiments, a base substrate is formed so that it includes a well that comprises a lip surrounding the well. In certain processes disclosed herein, the metal composition is sputtered so that the metal composition is below the lip of the well. In addition, a variety of different electrically conductive elements can be disposed on the base substrate. In some embodiments of the invention, the base substrate comprises a plurality of reference electrodes, a plurality of working electrodes and a plurality of counter electrodes clustered together in units consisting essentially of one working electrode, one counter electrode and one reference electrode, and the clustered units are longitudinally distributed on the base substrate in a repeating pattern of units.

Embodiments of the invention include further elements designed for use with the sensor apparatuses that are disclosed herein, for example those that are designed to analyze electrical signal data obtained from sputtered electrodes disposed on the base substrate. In some embodiments of the invention, the analyte sensor apparatus includes a processor and a computer-readable program code having instructions, which when executed, cause the processor to assess electrochemical signal data obtained from at least one working electrode and then compute analyte concentrations based upon the electrochemical signal data obtained from the working electrode. In certain embodiments of the invention, the processor compares electrochemical signal data obtained from multiple working electrodes in order to, for example, adapt different electrodes to sense different analytes, and/or to focus on different concentration ranges of a single analyte; and/or to indentify or characterize spurious sensor signals (e.g. sensor noise, signals caused by interfering compounds and the like) so as to enhance the accuracy of the sensor readings.

In some embodiments of the invention, the base structure comprises a flexible yet rigid and flat structure suitable for use in photolithographic mask and etch processes. In this regard, the base structure typically includes at least one surface having a high degree of uniform flatness. Base structure materials can include, for example, metals such as stainless steel, aluminum and nickel titanium memory alloys (e.g. NITINOL) as well as polymeric/plastic materials such as delrin, etc. Base structure materials can be made from, or coated with, a dielectric material. In some embodiments, the base structure is non-rigid and can be a layer of film or insulation that is used as a substrate for patterning electrical elements (e.g. electrodes, traces and the like), for example plastics such as polyimides and the like. An initial step in the methods of the invention typically includes the formation of a base substrate of the sensor. Optionally, the planar sheet of material is formed and/or disposed on a support such as a glass or ceramic plate during sensor production (see, e.g. FIG. 2). The base structure can be disposed on a support (e.g. a glass plate) by any desired means, for example by controlled spin coating. Optionally, a base substrate layer of insulative material is formed on the support, typically by applying the base substrate material onto the support in liquid form and thereafter spinning the support to yield a base substrate structure that is thin and of a substantially uniform thickness. These steps can be repeated to build up a base substrate structure to a desired thickness. This can then be followed by a sequence of photolithographic and/or chemical mask and etch steps to form the electrically conductive components. In an illustrative form, the base substrate comprises a thin film sheet of insulative material, such as a polyimide substrate that is used to pattern electrical elements. The base substrate structure may comprise one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof.

The methods of the invention include forming an electrically conductive layer on the base substrate that function as one or more sensing elements. Typically these sensing elements include electrodes, electrical conduits (e.g. traces and the like), contact pads and the like that are formed by one of the variety of methods known in the art such as photolithography, etching and rinsing to define the geometry of the active electrodes. The electrodes can then be made from electrochemically active materials having defined architectures, for example by using sputtered Pt black for the working electrode. A sensor layer such as a analyte sensing enzyme layer can then be disposed on the sensing layer by electrochemical deposition or a method other than electrochemical deposition such as spin coating, followed by vapor crosslinking, for example with a dialdehyde (glutaraldehyde) or a carbodi-imide.

In an exemplary embodiment of the invention, the base substrate is initially coated with a thin film conductive layer by electrode deposition, surface sputtering, or other suitable patterning or other process step. In one embodiment this conductive layer may be provided as a plurality of thin film conductive layers, such as an initial chrome-based layer suitable for chemical adhesion to a polyimide base substrate followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base substrate. In an illustrative sensor construction designed for use as a subcutaneous glucose sensor, each sensor trace can include two or three parallel sensor elements corresponding with two or three separate electrodes such as a working electrode, a counter electrode and a reference electrode.

Embodiments of the invention include methods of adding a plurality of materials to the surface(s) of the sputtered electrode(s). One such embodiment of the invention is a method of making a sensor apparatus (e.g. a glucose sensor) for implantation within a mammal comprising the steps of: providing a base substrate; forming a conductive layer on the base substrate, wherein the conductive layer includes an electrode formed from a sputtering process that generates metallic columns of a certain architecture, forming an analyte sensing layer on the conductive layer, wherein the analyte sensing layer includes a composition that can alter the electrical current at the electrode in the conductive layer in the presence of an analyte (e.g. glucose oxidase); optionally forming a protein layer over the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer.

In the working embodiments of the invention that are disclosed herein, the analyte sensing layer comprises glucose oxidase. Optionally, the apparatus comprises an adhesion promoting layer disposed between the analyte sensing layer and the analyte modulating layer. In some embodiments of the invention, the analyte modulating layer comprises a hydrophilic comb-copolymer having a central chain and a plurality of side chains coupled to the central chain, wherein at least one side chain comprises a silicone moiety. Typically, the apparatus comprises a biocompatible material on an external surface that is adapted to contact biological tissues or fluids when implanted in vivo. In the working embodiments of the invention that are disclosed herein, the analyte sensor apparatus is an amperometric glucose sensor exhibits a highly desirable oxygen response profile. In such embodiments, the amperometric glucose sensor generates a first signal in a solution comprising 100 mg/dL glucose and 5% oxygen and a second signal in a solution comprising 100 mg/dL glucose and 0.1% oxygen (i.e. test conditions where the only substantive difference is the % oxygen), and the first signal and the second signal differ by less than 10%.

Additional functional coatings or cover layers can then be applied to an electrode or other sensor element by any one of a wide variety of methods known in the art, such as spraying, dipping, etc. Some embodiments of the present invention include an analyte modulating layer deposited over an enzyme-containing layer that is disposed over a working electrode. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as the exact composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein.

In some embodiments of the invention, the sensor is made by methods which apply an analyte modulating layer that comprises a hydrophilic membrane coating which can regulate the amount of analyte that can contact the enzyme of the sensor layer. For example, a cover layer that is added to the glucose sensing elements of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a hydrophilic polymer. In some embodiments of the invention, the analyte modulating layer comprises a linear polyurethane/polyurea polymer and/or a branched acrylate polymer; and/or a mixture of such polymers.

In some embodiments of the methods of invention, an adhesion promoter layer is disposed between a cover layer (e.g. an analyte modulating membrane layer) and a analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art.

The finished sensors produced by such processes are typically quickly and easily removed from a support structure (if one is used), for example, by cutting along a line surrounding each sensor on the support structure. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. Since the base substrate is typically not physically attached or only minimally adhered directly to the underlying support, the sensors can be lifted quickly and easily from the support structure, without significant further processing steps or potential damage due to stresses incurred by physically pulling or peeling attached sensors from the support structure. The support structure can thereafter be cleaned and reused, or otherwise discarded. The functional coating layer(s) can be applied either before or after other sensor components are removed from the support structure (e.g. by cutting).

Embodiments of the invention also include methods of sensing an analyte (e.g. glucose) within the body of a mammal (e.g. a diabetic patient), the method comprising implanting a analyte sensor embodiment disclosed herein into an in vivo environment and then sensing one or more electrical fluctuations such as alteration in current at the working electrode and correlating the alteration in current with the presence of the analyte, so that the analyte is sensed. Typically, this method comprises implanting a glucose sensor disclosed herein within the interstitial space of a diabetic individual, sensing an alteration in current at the working electrode in the presence of glucose; and then correlating the alteration in current with the presence of the glucose, so that glucose is sensed. While typical embodiments of the invention pertain to glucose sensors, the sputtered sensor electrodes disclosed herein can be adapted for use with a wide variety of devices known in the art.

As discussed in detail below, embodiments of the invention include sensor systems comprising addition elements designed to facilitate sensing of an analyte. For example, in certain embodiments of the invention, the base material comprising the sensor electrodes is disposed within a housing (e.g. a lumen of a catheter) and/or associated with other components that facilitate analyte (e.g. glucose) sensing. One illustrative sensor system comprises a processor, a base comprising a first longitudinal member and a second longitudinal member, the first and second longitudinal members each comprising at least one electrode having an electrochemically reactive surface, wherein the electrochemically reactive surface generates an electrochemical signal that is assessed by the processor in the presence of an analyte; and a computer-readable program code having instructions, which when executed cause the processor to assess electrochemical signal data obtained from the electrodes; and compute an analyte presence or concentration based upon the electrochemical signal data obtained from the electrode. Embodiments of the invention described herein can also be adapted and implemented with amperometric sensor structures, for example those disclosed in U.S. Patent Application Publication Nos. 20070227907, 20400025238, 20110319734 and 20110152654, the contents of each of which are incorporated herein by reference.

B. Illustrative Analyte Sensor Constituents Used in Embodiments of the Invention The following disclosure provides examples of typical elements/constituents used in sensor embodiments of the invention. While these elements can be described as discrete units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Figure 2:
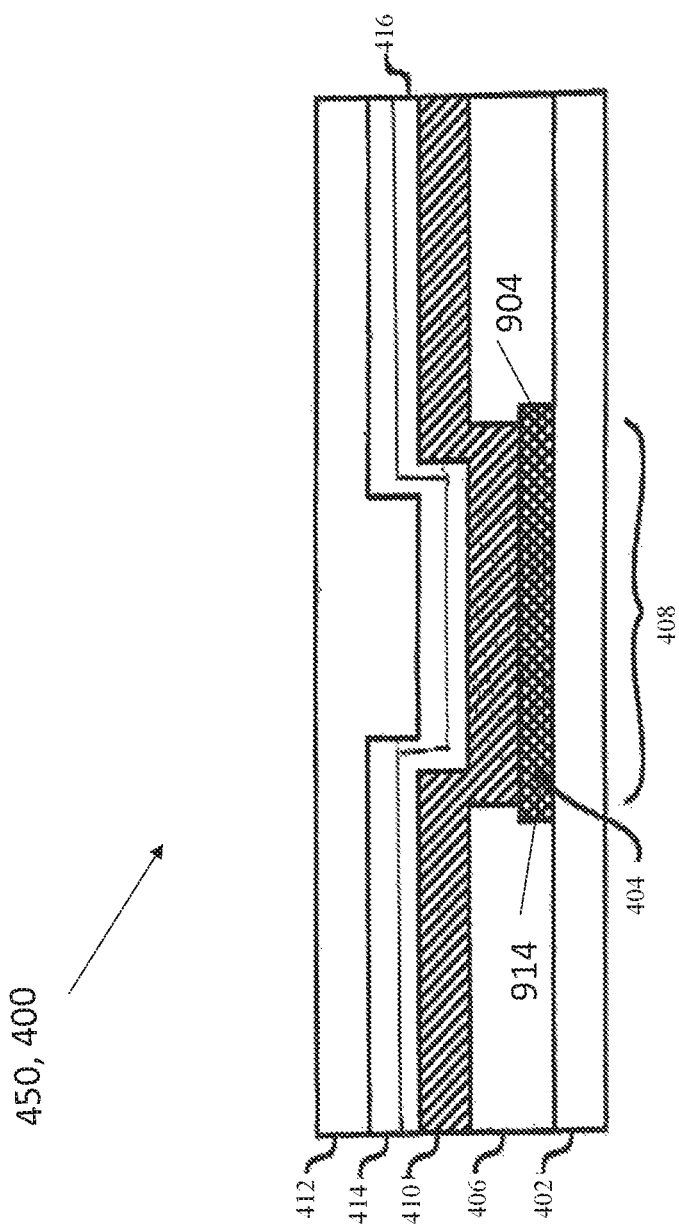
FIG. 2 shows illustrations of amperometric analyte sensors formed from a plurality of planar layered elements.

Sensors of the invention typically include a base constituent (see, e.g. element 402 in FIG. 2). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

Conductive Constituent

The electrochemical sensors of the invention typically include a conductive constituent disposed upon the base constituent that includes at least one electrode comprising the pillar architecture (as described herein) for contacting an analyte or its byproduct (e.g. oxygen and/or hydrogen peroxide) to be assayed (see, e.g. element 404 in FIG. 2). The term "conductive constituent" is used herein according to art accepted terminology and refers to electrically conductive sensor elements such as electrodes, contact pads, traces and the like. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 410 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One or more of the working, counter, reference and counter/reference electrodes comprise the pillar structures described herein. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure. In certain embodiments of the invention, the reactive surfaces of the electrodes are of different relative areas/sizes, for example a 1× reference electrode, a 3.2× working electrode and a 6.3× counter electrode.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetra-fluoroethylenes, the perfluoronated ionomer Nafion™, polyphenylenediamine, epoxy and the like.

Analyte Sensing Constituent

The electrochemical sensors of the invention include an analyte sensing constituent disposed on the pillar structures of the electrodes of the sensor (see, e.g. element 410 in FIG. 2). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard, the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

As noted above, in some embodiments of the invention, the analyte sensing constituent includes an agent (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Protein Constituent

The electrochemical sensors of the invention optionally include a protein constituent disposed between the analyte sensing constituent and the analyte modulating constituent (see, e.g. element 416 in FIG. 2). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 414 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as 3-aminopropyltrimethoxysilane.

Analyte Modulating Constituent

The electrochemical sensors of the invention include an analyte modulating constituent disposed on the sensor (see, e.g. element 412 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally, such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The analyte modulating sensor membrane assembly serves several functions, including selectively allowing the passage of glucose therethrough (see, e.g. U.S. Patent Application No. 2011-0152654).

Cover Constituent

The electrochemical sensors of the invention include one or more cover constituents, which are typically electrically insulating protective constituents (see, e.g. element 406 in FIG. 2). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imagable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Illustrative Sensor Stacks

An embodiment of the invention having a layered stack of constituents is shown in FIG. 2. FIG. 2 illustrates a cross-section of a typical sensor embodiment 400 of the present invention that includes constituents discussed above. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2 includes a base substrate layer 402 to support the sensor 400. The base substrate layer 402 can be made of a material such as a metal and/or a ceramic and/or a polymeric substrate, which may be self-supporting or further supported by another material as is known in the art. Embodiments of the invention include a conductive layer 404 which is disposed on and/or combined with the base substrate layer 402. Typically, the conductive layer 404 comprises one or more electrically conductive elements that function as electrodes. An operating sensor 400 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 402 and/or conductive layer 404 can be generated using many known techniques and materials. In certain embodiments of the invention, the electrical circuit of the sensor is defined by etching the disposed conductive layer 404 into a desired pattern of conductive paths. A typical electrical circuit for the sensor 400 comprises two or more adjacent conductive paths with regions at a proximal end to form contact pads and regions at a distal end to form sensor electrodes. An electrically insulating cover layer 406 such as a polymer coating can be disposed on portions of the sensor 400. Acceptable polymer coatings for use as the insulating protective cover layer 406 can include, but are not limited to, non-toxic biocompatible polymers such as silicone compounds, polyimides, biocompatible solder masks, epoxy acrylate copolymers, or the like. In the sensors of the present invention, one or more exposed regions or apertures 408 can be made through the cover layer 406 to open the conductive layer 404 to the external environment and to, for example, allow an analyte such as glucose to permeate the layers of the sensor and be sensed by the sensing elements. Apertures 408 can be formed by a number of techniques, including laser ablation, tape masking, chemical milling or etching or photolithographic development or the like. In certain embodiments of the invention, during manufacture, a secondary photoresist can also be applied to the protective layer 406 to define the regions of the protective layer to be removed to form the aperture(s) 408. The exposed electrodes and/or contact pads can also undergo secondary processing (e.g. through the apertures 408), such as additional plating processing, to prepare the surfaces and/or strengthen the conductive regions.

In the sensor configuration shown in FIG. 2, an analyte sensing layer 410 is disposed on one or more of the exposed electrodes of the conductive layer 404. Typically, the analyte sensing layer 410 is an enzyme layer. Most typically, the analyte sensing layer 410 comprises an enzyme capable of producing and/or utilizing oxygen and/or hydrogen peroxide, for example the enzyme glucose oxidase. Optionally, the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 410 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can be monitored by any one of a variety of sensor detector apparatuses such as a universal sensor amperometric biosensor detector or one of the variety of similar devices known in the art such as glucose monitoring devices produced by Medtronic Diabetes.

In embodiments of the invention, the analyte sensing layer 410 can be applied over portions of the conductive layer or over the entire region of the conductive layer. Typically the analyte sensing layer 410 is disposed on the working electrode which can be the anode or the cathode. Optionally, the analyte sensing layer 410 is also disposed on a counter and/or reference electrode. Methods for generating a thin analyte sensing layer 410 include brushing the layer onto a substrate (e.g. the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by a sputtering process).

Typically, the analyte sensing layer 410 is coated and or disposed next to one or more additional layers. Optionally, the one or more additional layers includes a protein layer 416 disposed upon the analyte sensing layer 410. Typically, the protein layer 416 comprises a protein such as human serum albumin, bovine serum albumin or the like. Typically, the protein layer 416 comprises human serum albumin. In some embodiments of the invention, an additional layer includes an analyte modulating layer 412 that is disposed above the analyte sensing layer 410 to regulate analyte contact with the analyte sensing layer 410. For example, the analyte modulating membrane layer 412 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In certain embodiments of the invention, an adhesion promoter layer 414 is disposed between the analyte modulating layer 412 and the analyte sensing layer 410 as shown in FIG. 12 in order to facilitate their contact and/or adhesion. In a specific embodiment of the invention, an adhesion promoter layer 414 is disposed between the analyte modulating layer 412 and the protein layer 416 as shown in FIG. 2 in order to facilitate their contact and/or adhesion. The adhesion promoter layer 414 can be made from any one of a wide variety of materials known in the art to facilitate the bonding between such layers. Typically, the adhesion promoter layer 414 comprises a silane compound. In alternative embodiments, protein or like molecules in the analyte sensing layer 410 can be sufficiently crosslinked or otherwise prepared to allow the analyte modulating membrane layer 412 to be disposed in direct contact with the analyte sensing layer 410 in the absence of an adhesion promoter layer 414.

C. Typical System Embodiments of the Invention

A specific illustrative system embodiment consists of a glucose sensor comprising a sputtered platinum electrode composition as disclosed herein, a transmitter and receiver and a glucose meter. In this system, radio signals from the transmitter can be sent to the pump receiver at regular time periods (e.g. every 5 minutes) to provide real-time sensor glucose (SG) values. Values/graphs can be displayed on a monitor of the pump receiver so that a user can self monitor blood glucose and deliver insulin using their own insulin pump. Typically the sensor systems disclosed herein can communicate with other medical devices/systems via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

Figure 3:
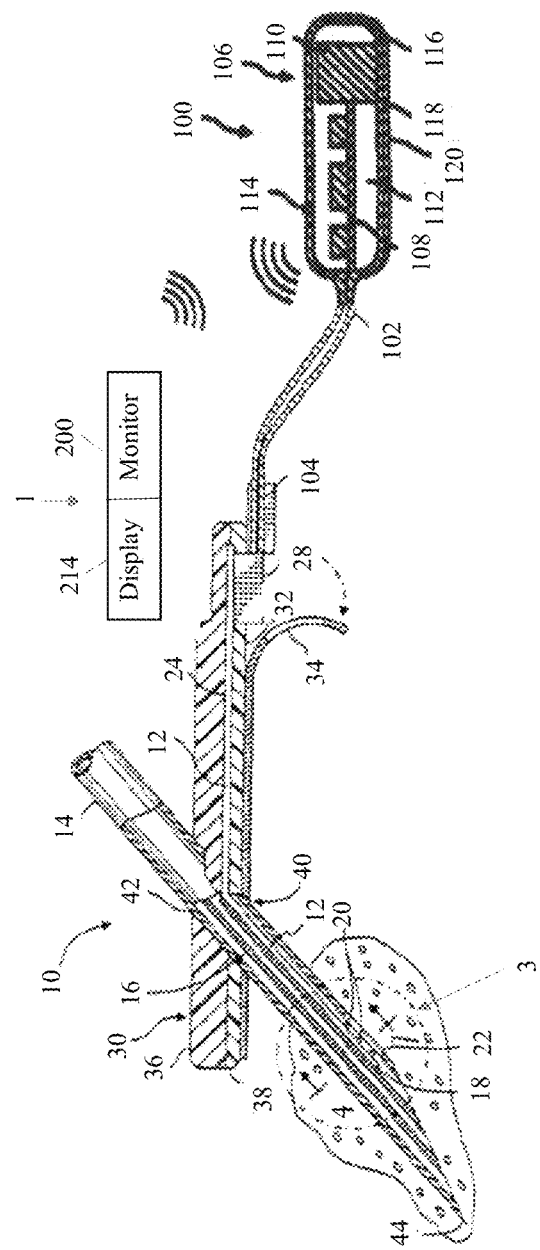
FIG. 3 provides a perspective view illustrating one type of subcutaneous sensor insertion set, a telemetered characteristic monitor transmitter device, and a data receiving device, elements that can be adapted for use with embodiments of the invention.

FIG. 3 provides a perspective view of one generalized embodiment of subcutaneous sensor insertion system that can be adapted for use with the sensor electrodes disclosed herein and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 3 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The base is designed so that the sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 200 by a connector block 28 (or the like) as shown and described in U.S. Pat. No. 5,482,473, entitled FLEX CIRCUIT CONNECTOR, which is incorporated by reference.

As shown in FIG. 3, in accordance with embodiments of the present invention, subcutaneous sensor set 10 may be configured or formed to work with either a wired or wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 200 is coupled to a sensor set 10 by a cable 102 through a connector 104 that is electrically coupled to the connector block 28 of the connector portion 24 of the sensor set 10.

In the embodiment shown in FIG. 3, the telemetered characteristic monitor 200 includes a housing 106 that supports a printed circuit board 108, batteries 110, antenna 112, and the cable 102 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 200 is ready for use.

In the illustrative embodiment shown in FIG. 3, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. Nos. 4,562,751; 4,678,408; 4,685,903 or 4,573,994, to control delivery of insulin to a diabetic patient.

In the illustrative embodiment shown in FIG. 3, the sensor electrodes 10 may be used in a variety of sensing applications and may be configured in a variety of positions on a base structure and further be formed to include materials that allow a wide variety of functions. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 3, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 402 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

As noted above, embodiments of the sensor elements and sensors can be operatively coupled to a variety of other system elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Figure 4:
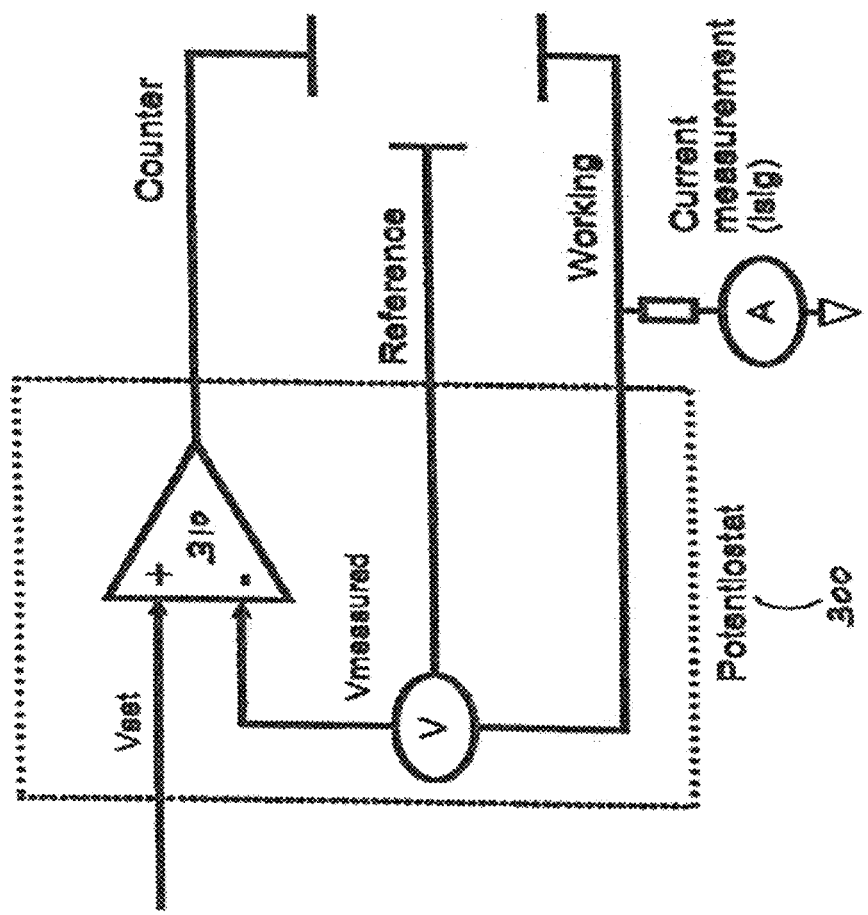
FIG. 4 shows a schematic of a potentiostat that may be used to measure current in embodiments of the present invention.

FIG. 4 shows a schematic of a potentiostat that may be used to measure current in embodiments of the present invention. As shown in FIG. 4, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (Isig) that is output from the potentiostat.

Embodiments of the invention include devices which process display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

EXAMPLES

The surface area ratio (SAR) is the ratio between real surface area and geometric area of the electrode. The active (or real) surface area determines the catalytic activity of sputtered electrodes. The active surface area of the platinum-working electrodes can be measured using the cyclic voltammetry method combined with hydrogen adsorption. In this context, various determinations of Pt surface area are well known in the art, see, e.g. Rodriguez et al., J. Chem. Educ., 2000, 77 (9), p 1195.

Common acronyms used in the examples include: WE Working Electrode; GOx Glucose Oxidase; HSA Human Serum Albumin; SITS Sensor In-vitro Test System; GLM Glucose Limiting Membrane (an embodiment of an analyte modulating layer); OQ Operational Qualification; SAR Surface Area Ratio; BTS Bicarbonate Test System; and EIS Electrochemical Impedance Spectroscopy. The BTS and SITS tests discussed in the example are tests used to evaluate aspects of sensor performance. SITS measures sensor signal in glucose solutions over 5-7 days, as wells as sensor oxygen response, temperature response, background current, linearity, stability, acetaminophen interference and response time. Dog tests are used to evaluate glucose sensor performance in vivo (Isig and calculated blood glucose level) in diabetic and non-diabetic dogs for up to 3 days and compares glucose level measured by continuous glucose sensors to that measured by a glucose meter.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

Example 1: Sputtering Conditions

Figure 5A:
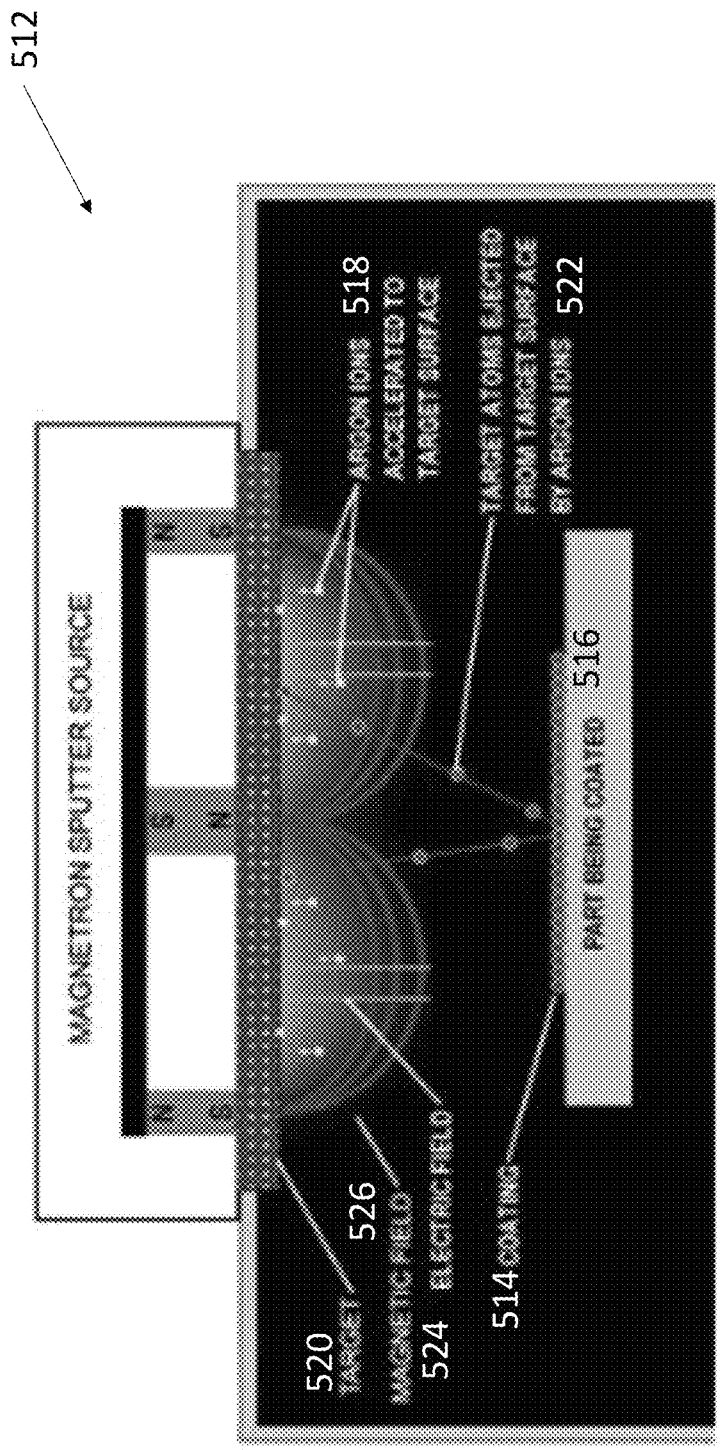
FIG. 5A illustrates a sputtering apparatus.

FIG. 5A illustrates a sputtering apparatus 512 for depositing a film 514 comprising a metal composition on a base substrate 516 of an electrode. A plasma comprising ionized gas particles 518 bombards target material 520 comprising the metal composition. Collision of the particles 518 with the target material 520 knocks off material 522 comprising the metal composition and accelerates the material to the target surface on the base substrate. The ionized gas particles 518 are accelerated towards target using electric and/or magnetic fields 524, 526. The particle collision is controlled by process power (i.e., power of the electric and/or magnetic fields until arrival of the ionized gas particles on the target material) and ionized gas particle composition and pressure. Key factors for controlling the morphology (e.g., porosity) of the deposited film include the ionized gas particle type (e.g., argon, helium), pressure of the ionized gas, and temperature in the reactor. Increased particle collisions on the target and range of incident angles are achieved with increased pressure, resulting in increased porosity and roughness of the deposited film.

Example Process Flows

Figure 5B:
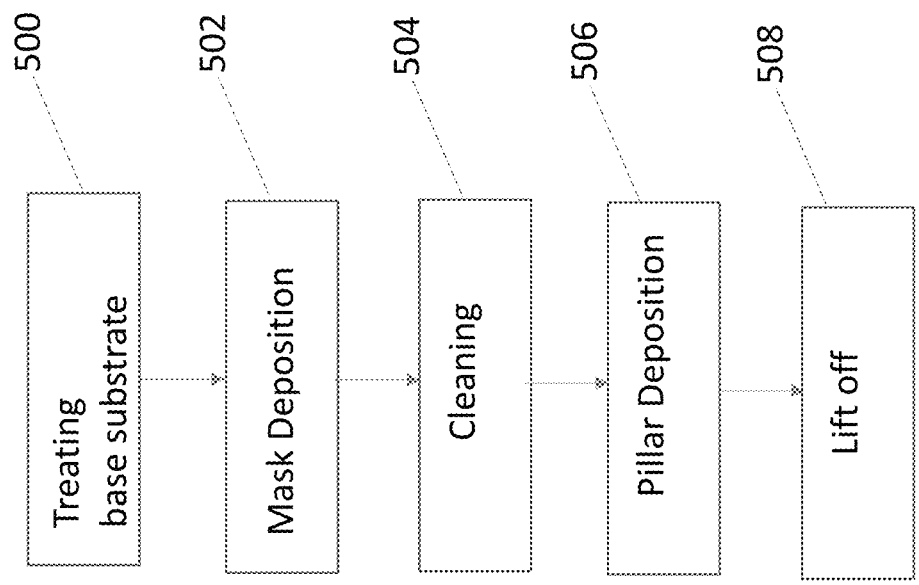
FIG. 5B illustrates a sputtering method.

FIG. 5B is a flowchart illustrating a metal pillar lift off patterning manufacturing process.

Block 500 represents the optional step of treating the substrate with O₂ plasma. However, any other plasma gas or treatment in general that makes surface hydrophillic and/or helps with adhesion for the subsequent photoresist lift-off mask layer may be used. In alternative embodiment, the starting material does not require this step.

Block 502 represents depositing a mask/stencil onto the substrate. In one embodiment, the step comprises patterning a photoresist lift-off mask onto the substrate using conventional methods such as photolithography. In an alternative embodiment, a physical mask/stencil is placed onto the substrate.

Block 504 represents an optional descum step using 02 plasma to ensure the exposed metal surfaces (electrodes in one embodiment) are clean and ready for metal pillar deposition in the sputterer. However, any other plasma gas or treatment in general that clears off surfaces from contamination, makes surfaces hydrophillic and/or helps with adhesion may be used. An alternative embodiment could use a starting material that doesn't require this step.

Block 506 represents metal (e.g., Pt) pillar deposition. In one embodiment, the step comprises sputter depositing metal under high pressure (in this case 200 mTorr) for the requisite amount of time to achieve required film/pillar heights, surface area, impedance and/or other electrical, mechanical, chemical and biological properties. Any metal that is sputter or e-beam deposited could be used to create metal pillars. At a minimum (and for example purposes) this includes, but is not limited to, gold, silver, copper, titanium, chromium, iridium, platinum, etc. Combinations of these metals (and others) could also be used along with ceramics and/or other materials (Ex. Titanium Nitride).

Block 508 represents removal/lift-off the underlying photoresist mask leaving behind metal pillars only in desired areas. The general patterning method details here revolve around lift-off patterning. However, the method can be extended to use other common patterning approaches such as wet-etching, dry-etching, masking, hard mask lift-off, etc.

Figure 6:
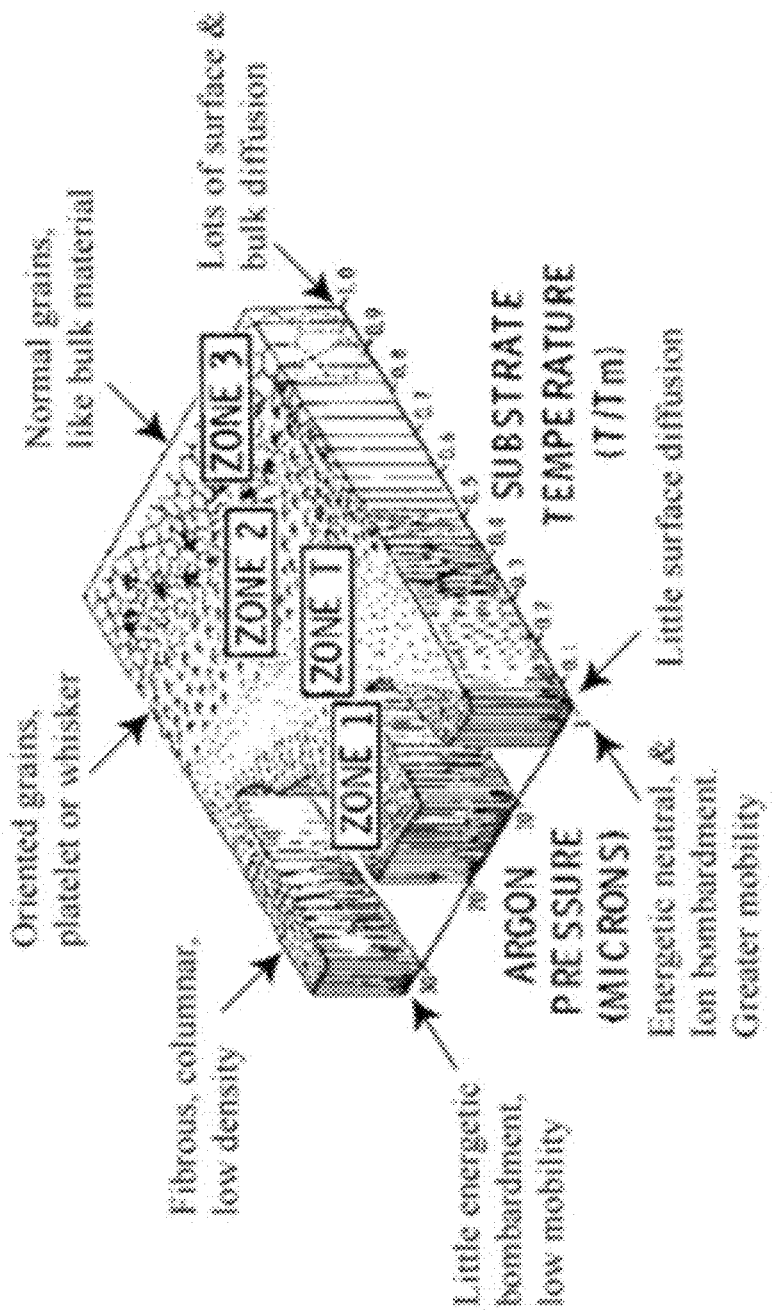
FIG. 6 illustrates the effect of sputtering conditions on the deposited material.

FIG. 6 illustrates how morphology of a Pt film deposited by sputtering varies as a function of process parameters (pressure and temperature).

In one or more embodiments, the ionized gas particles bombard the target material with high power in order to achieve practical deposition rates. However, the effect of power on SAR is non-linear.

Figure 7A:
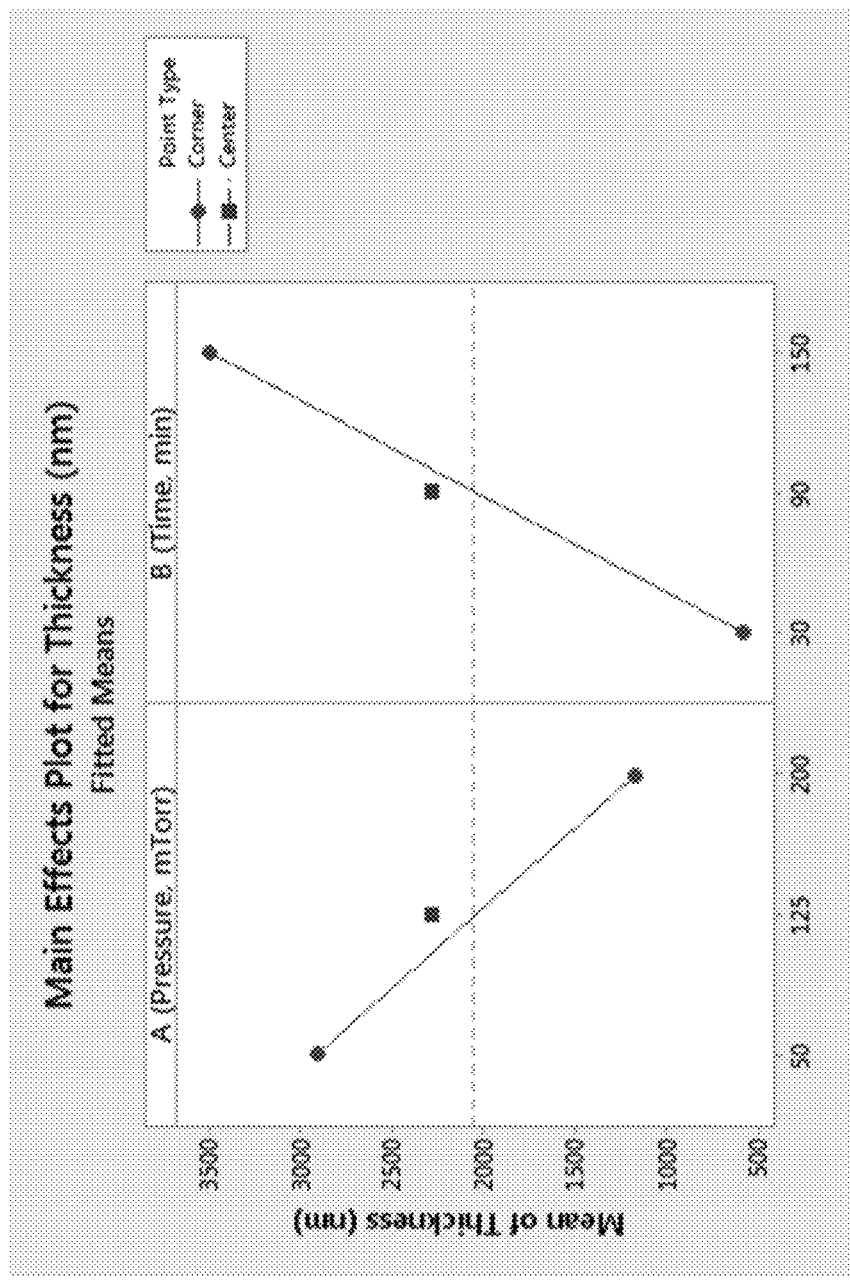
FIGS. 7A-7C illustrate deposited film thickness (FIG. 7A), SAR (FIG. 7B), and patterning yield (FIG. 7C) as a function of pressure over a range of 50 to 200 mTorr and deposition time in a range of 30 to 150 minutes.
Figure 7B:
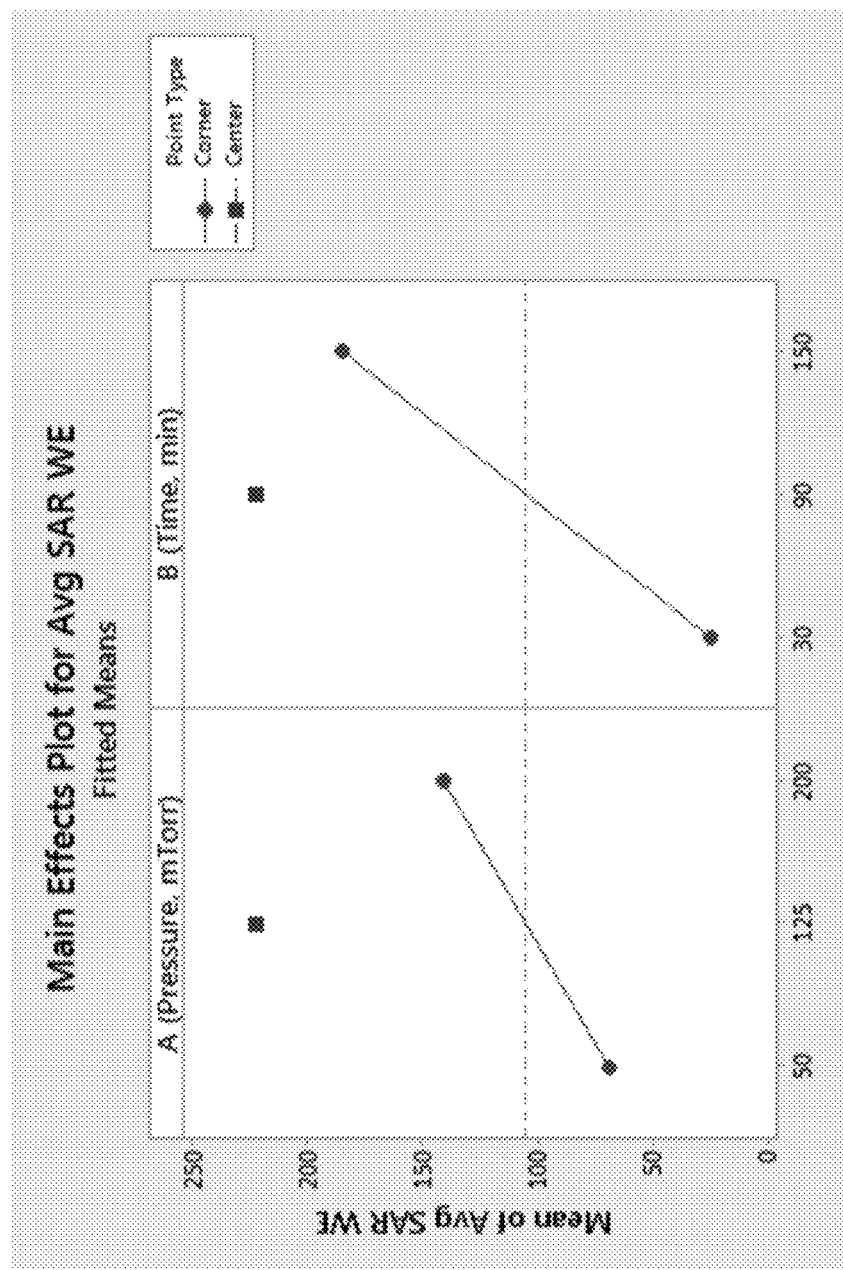
Figure 7C:
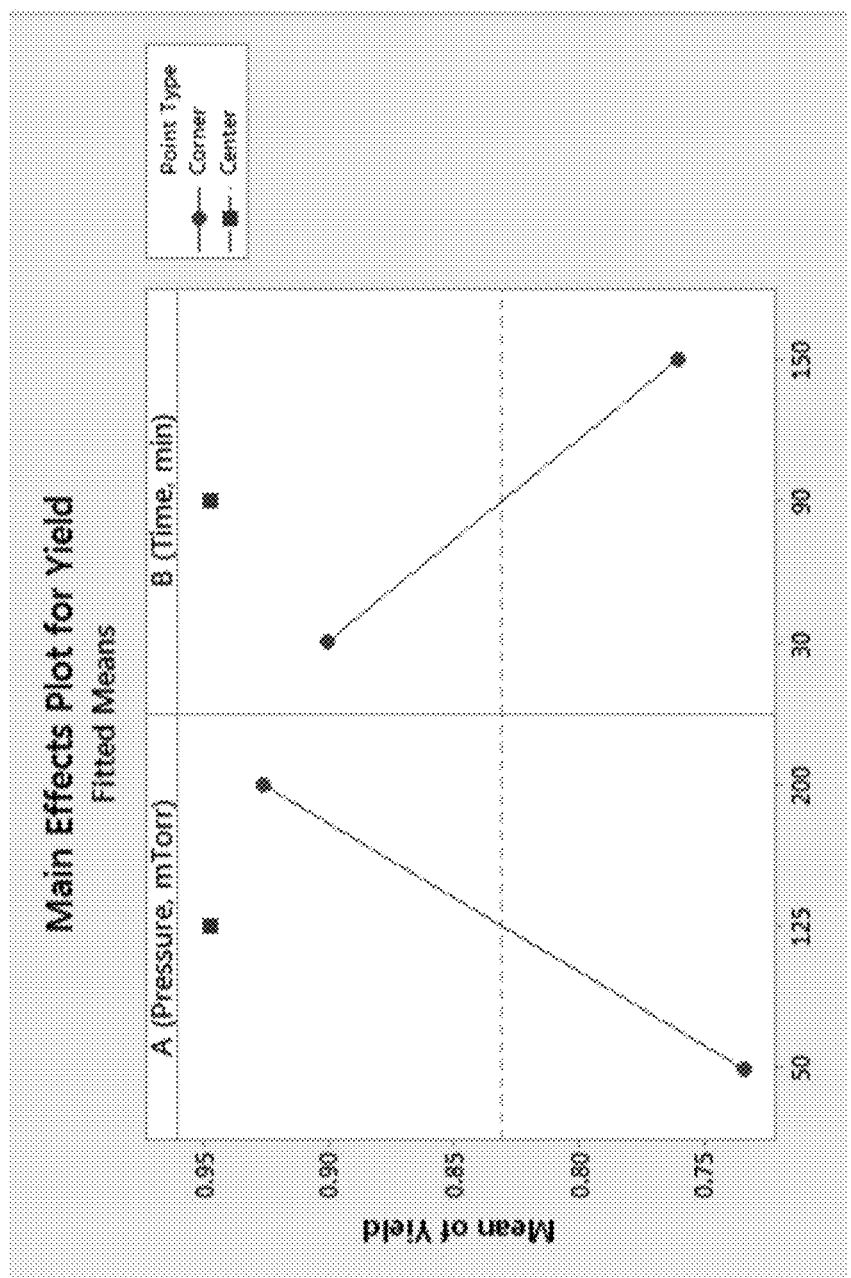

In one or more embodiments, the efficiency of pillar processing is improved by tuning process pressure and deposition time. FIGS. 7A-7C illustrate deposited film thickness, SAR, and patterning yield as a function of pressure over a range of 50 to 200 mTorr and deposition time in a range of 30 to 150 minutes. The data show that low pressure and longer deposition time result in higher deposited film thickness.

Figure 8B:
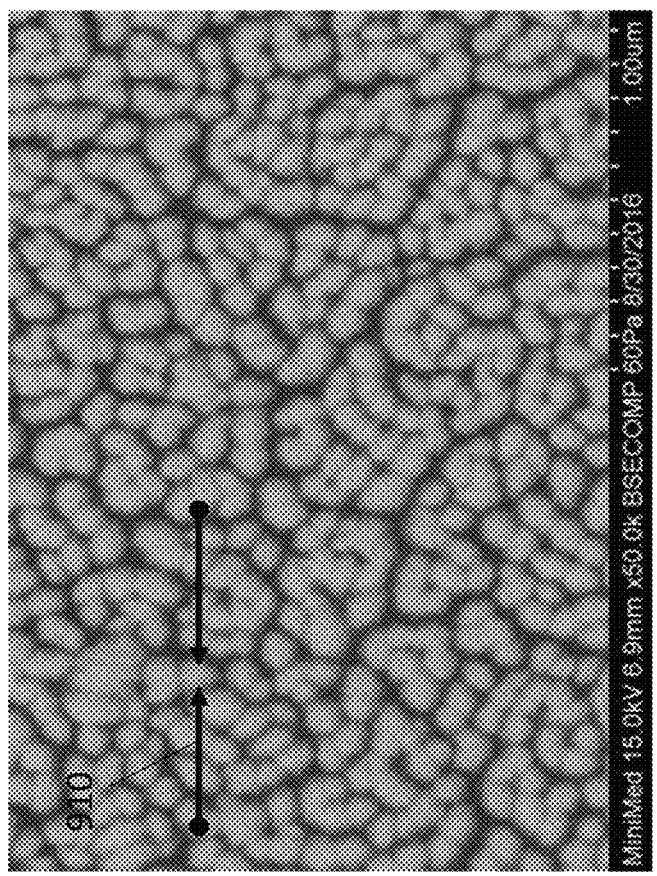
FIG. 8B illustrates the top view of Pt pillars achieved using a pressure of 125 mTorr after a deposition time of 90 minutes.
Figure 8A:
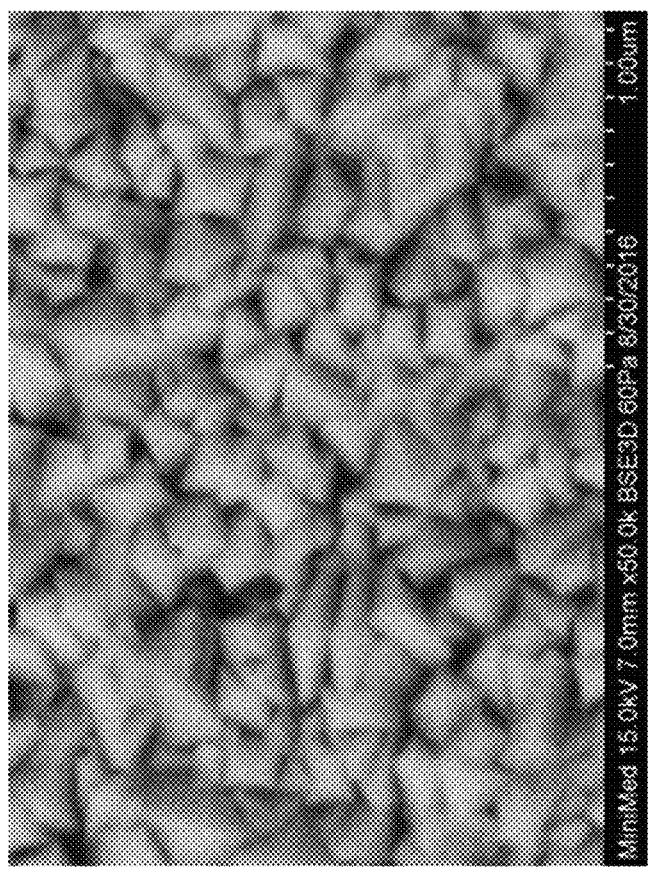
FIG. 8A shows is a top view of the film deposited using a pressure of 50 mTorr and a deposition time of 150 minutes.

FIG. 8A shows the film deposited using a pressure of 50 mTorr and a deposition time of 150 minutes, showing that the pressure of 50 mTorr lies below the threshold pressure for achieving Pt pillars (even after a deposition time of 150 minutes). While the deposition pressure of 50 mTorr yields a roughened surface with large grains (SAR>1), the resulting morphology does not comprise pillars.

FIG. 8B illustrates Pt pillars were achieved using a pressure of 125 mTorr after a deposition time of 90 minutes. Thus, a carefully selected process pressure enables shorter deposition times.

Figure 9A:
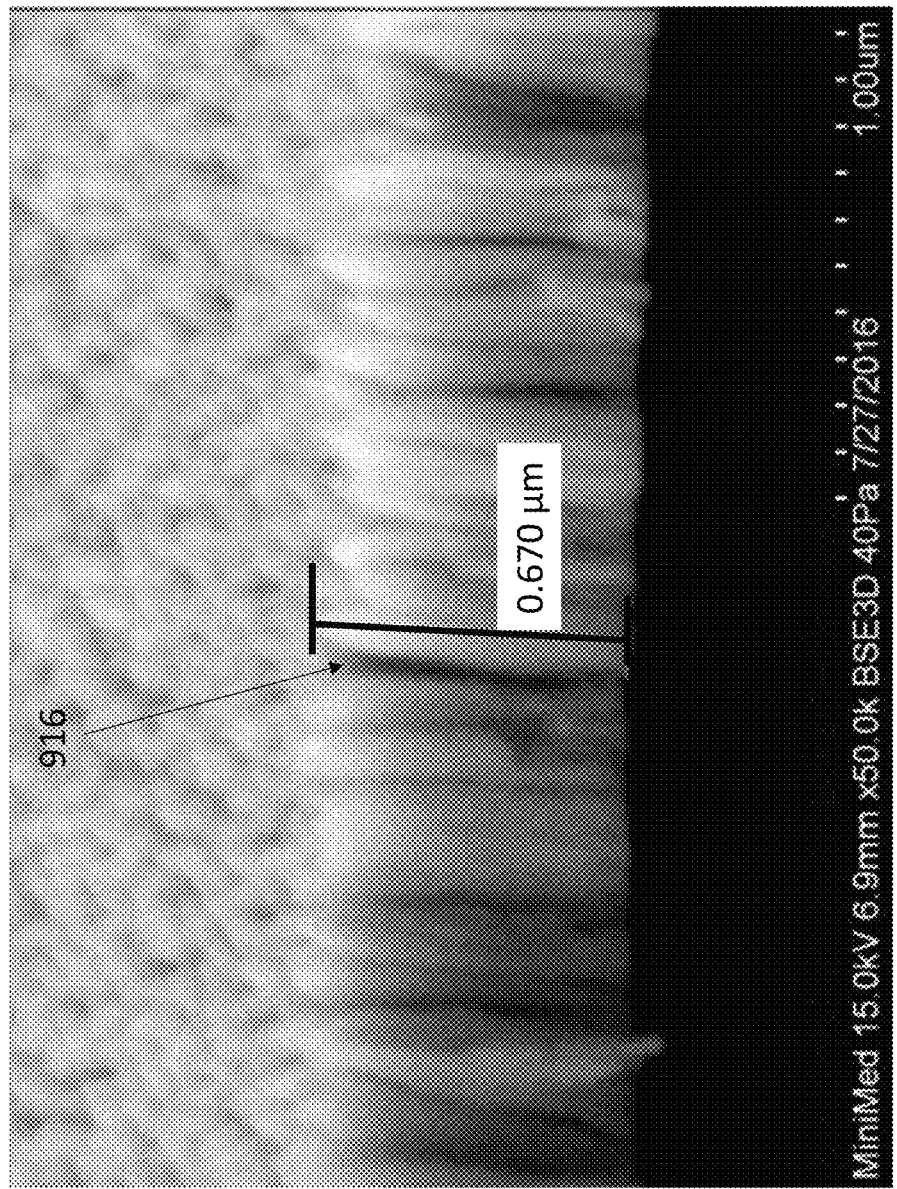
FIG. 9A illustrates a sputtering embodiment producing Pt pillars having a grain size of approximately 10-100 nm.
Figure 9B:
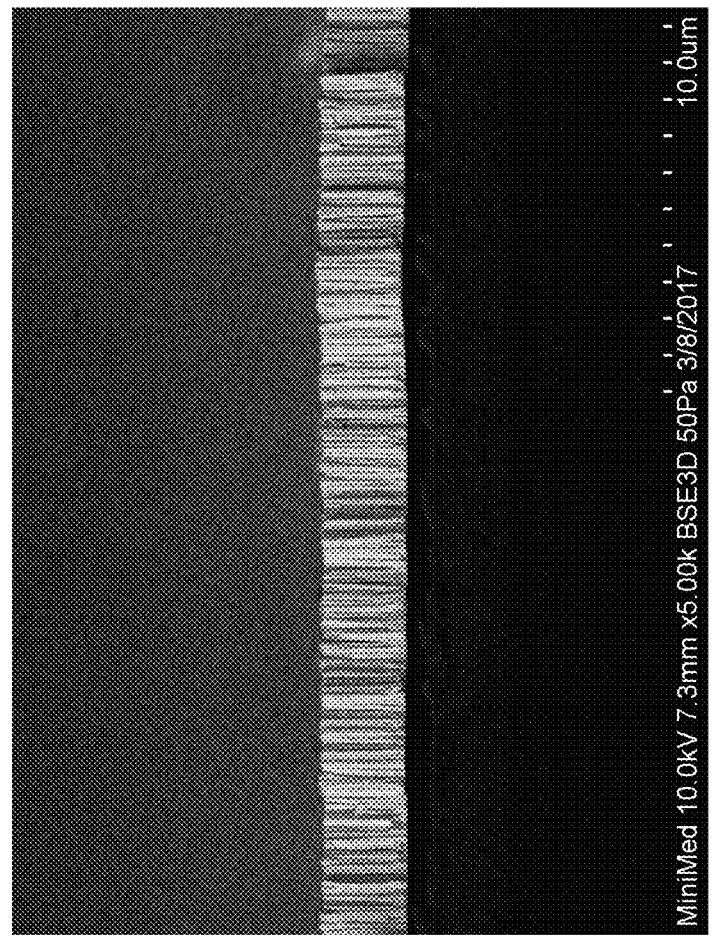
FIG. 9B-9G illustrate cross-sections of pillar architectures deposited using different sputter deposition times so the height of the pillars are different (in FIG. 9C, a pillar height is 2.49 micrometers, in FIG. 9E a pillar is 3.5 micrometers, and in FIG. 9G a pillar height is 3.73 micrometers).
Figure 9C:
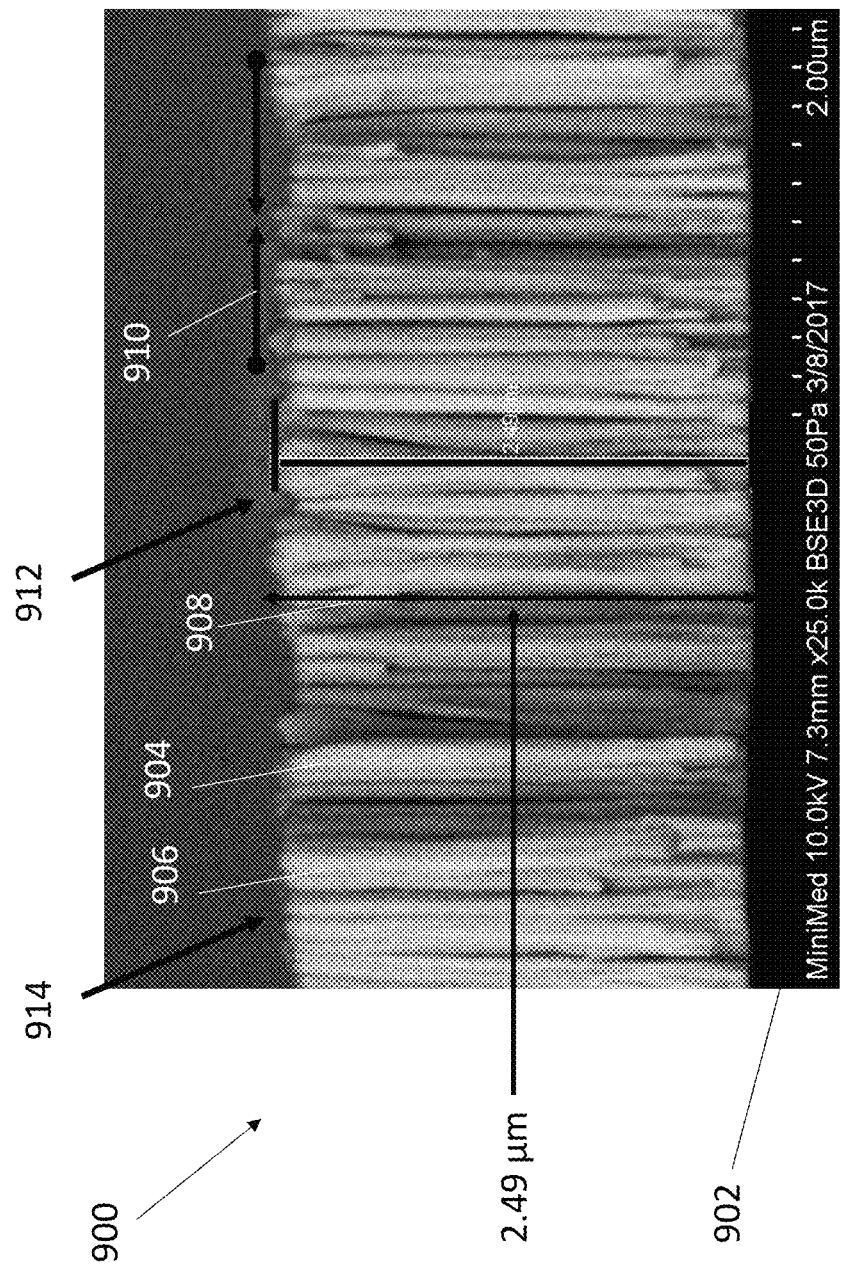
Figure 9D:
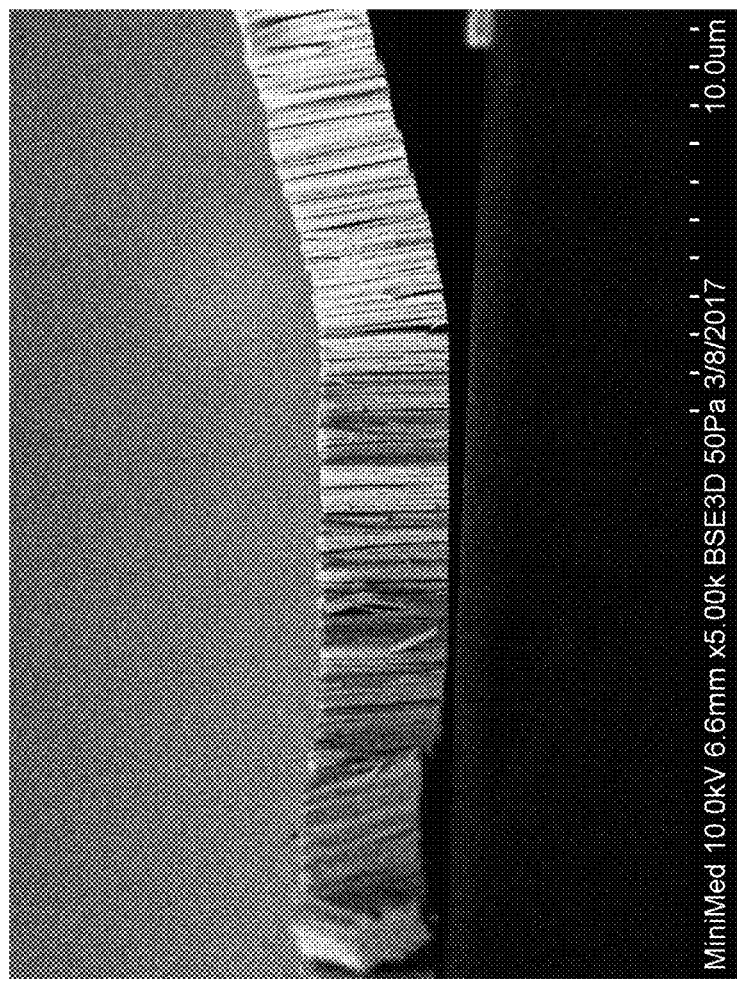
Figure 9E:
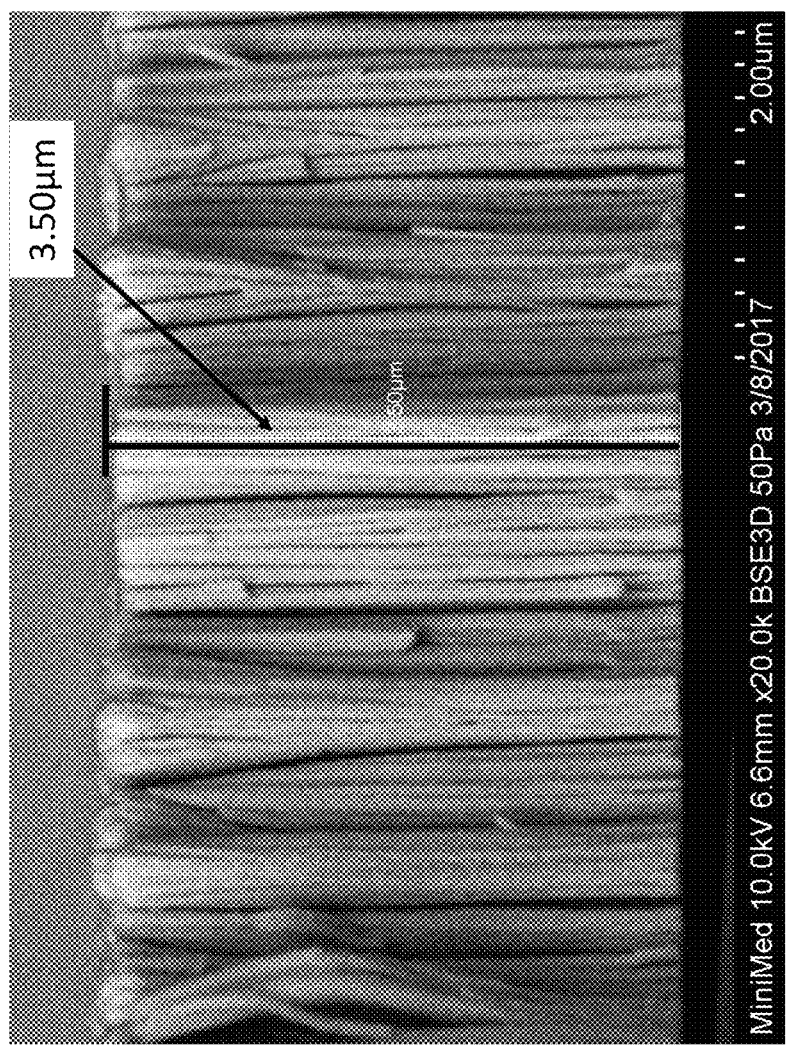
Figure 9F:
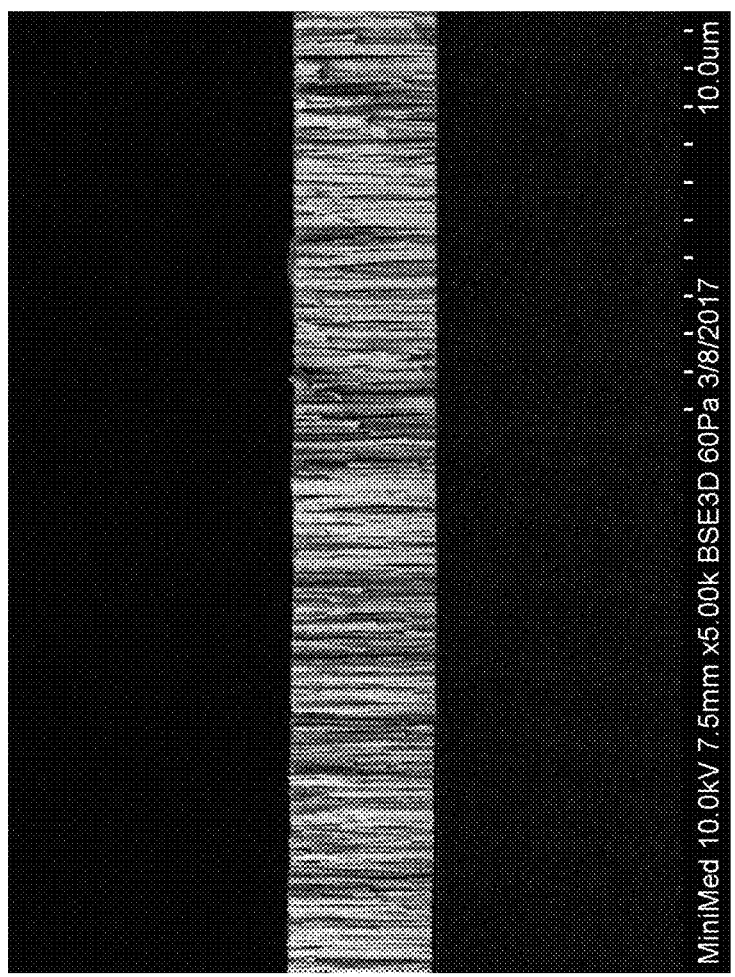
Figure 9G:
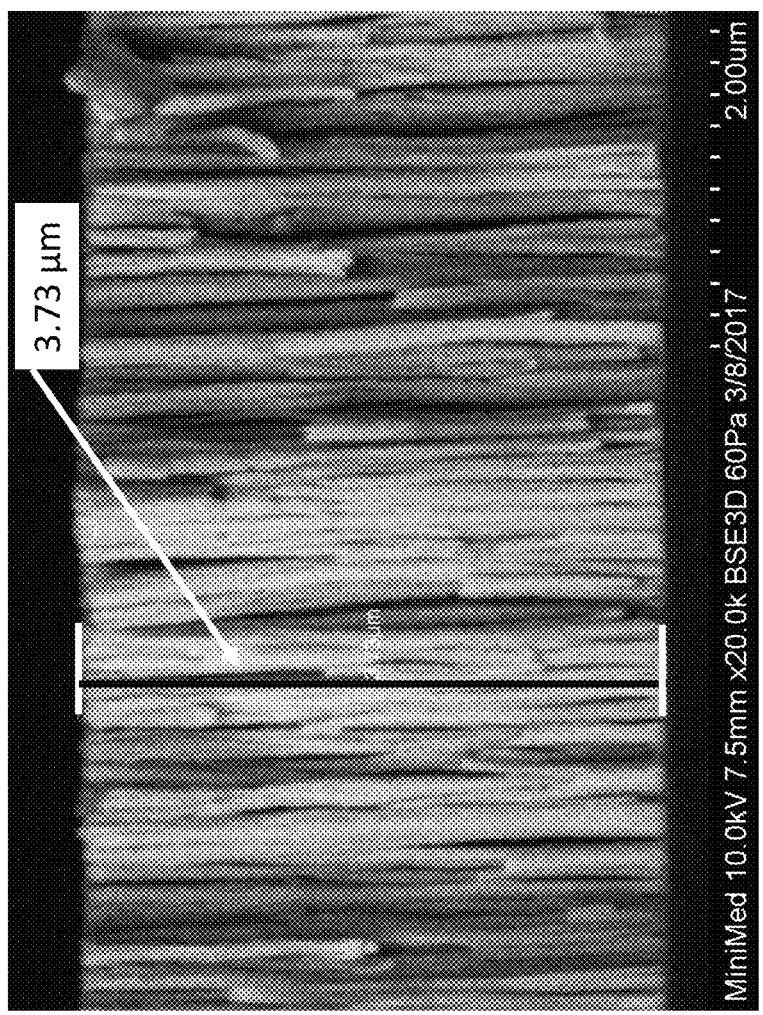

FIG. 9A illustrates a sputtering embodiment producing Pt pillars having a grain size of approximately 10-100 nm with fissures separating grain clusters (a fibrous film structure with open porosity). The SAR is higher than mirror-finish, and the sputtered Pt is characterized by 0.15 SAR/nm.

FIG. 9B-9G illustrate pillar architectures using different sputter deposition times so the height of the pillars are different (pillar height/film thickness increases linearly with deposition time). FIGS. 9A-9G illustrate A composition of matter 900, comprising a base substrate 902; and pillars 904 disposed on the base substrate 902, wherein the pillars 904 each comprise a sputtered metal composition 906, have a height 908 up to 10 micrometers, and have a diameter 910 (see also FIG. 8B) in a range of 1 nanometer-1000 nanometers.

Figure 10:
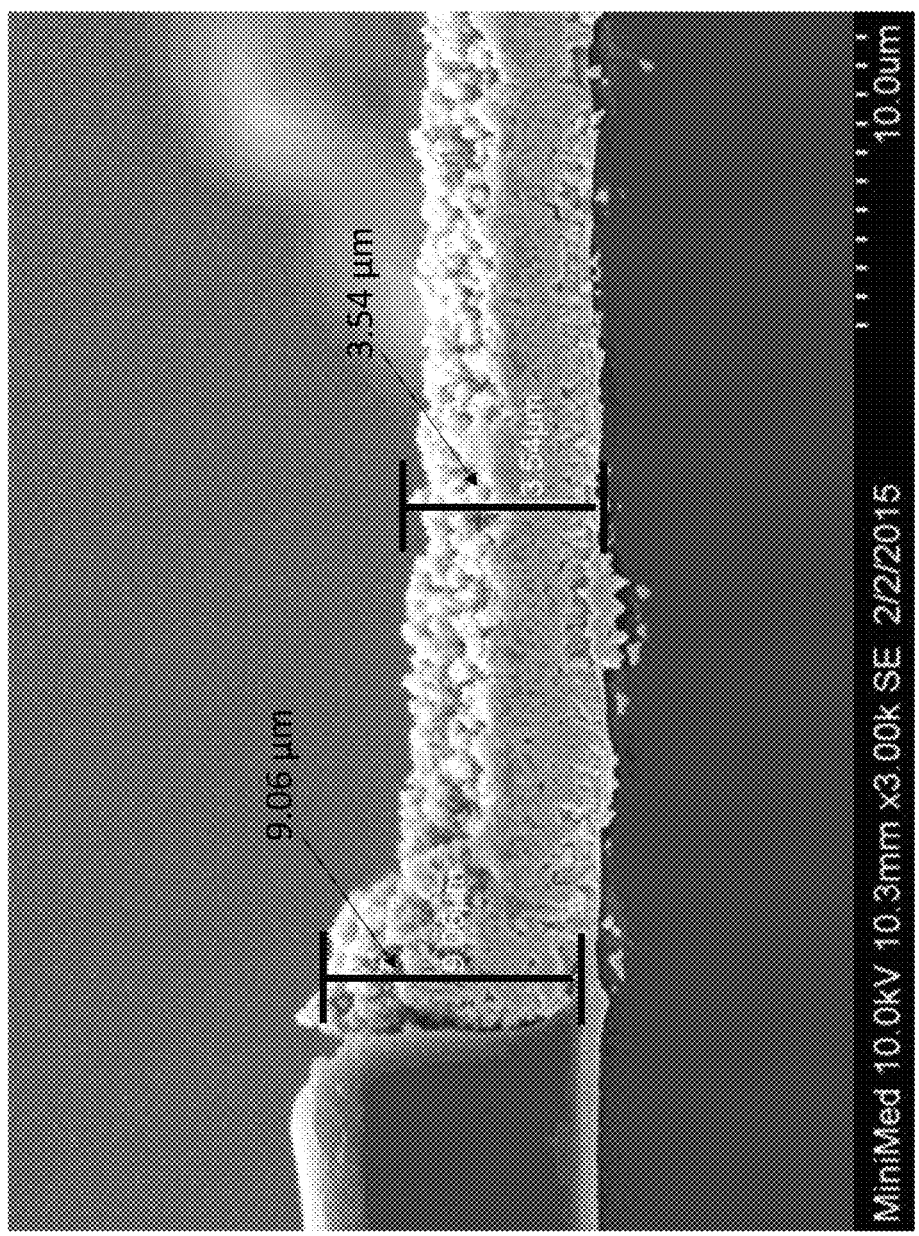
FIG. 10 is a scanning electron microscope (SEM) image of electroplated Pt for comparison.

FIG. 10 is an SEM image of electroplated Pt for comparison.

TABLE 1

SAR as a function of deposition time, evidencing a linear relationship between SAR and film thickness.

| Time (minutes) | SAR (Avg) | SAR (SEM) |
| --- | --- | --- |
| 0 | 76.9 | 3.0 |
| 3 | 74.5 | 1.8 |
| 9 | 74.3 | 1.9 |

Figure 11:
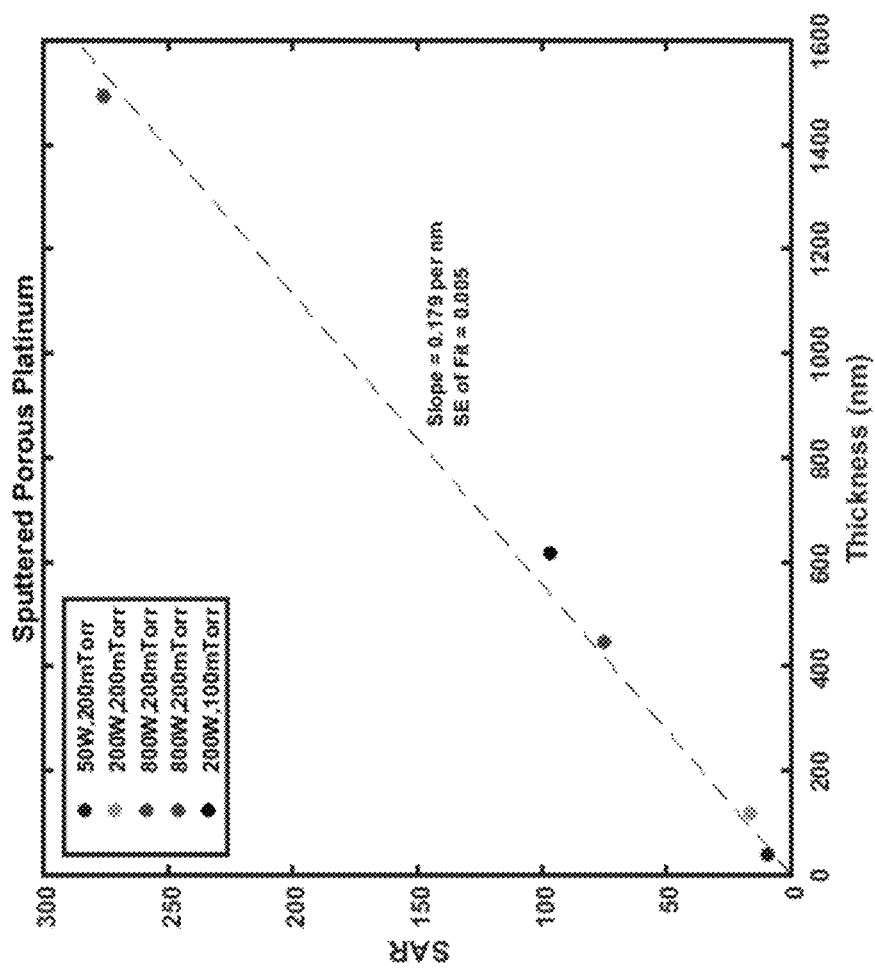
FIG. 11 plots SAR as a function of film thickness for various sputtering parameters.

FIG. 11 illustrates SAR is linear with film thickness, showing that sputtering provides excellent design control of the active surface area. In one or more embodiments, the pillars form a structure having a Surface Area Ratio (SAR) in a range of 0-500.

TABLE 2

| Deposition parameters | | |
| --- | --- | --- |
| Power (W) | Rate A/s | Avg SAR/nm |
| 50 | 0.037 | 0.250 |
| 200 | 0.44 | 0.142 |
| 800 | 2.77 | 0.184 |

Embodiments of the present invention have achieved pillars having diameters/widths in a range from 1 nm-1000 nm and heights in a range of 0-10 micrometers (e.g., in range of 2-4 micrometers). Although the pillar architectures may be uniform and ordered (e.g., variation of pillar heights <25% assuming a flat surface that the pillars have been deposited on), rough or non-uniform pillar architectures may also be fabricated. If the surface the pillars are deposited on is non-uniform or has a shape (see e.g., FIG. 9D), then the pillars will mimic that shape.

Example 2: Electrical Characterization of Pillar Morphology

Figure 12A:
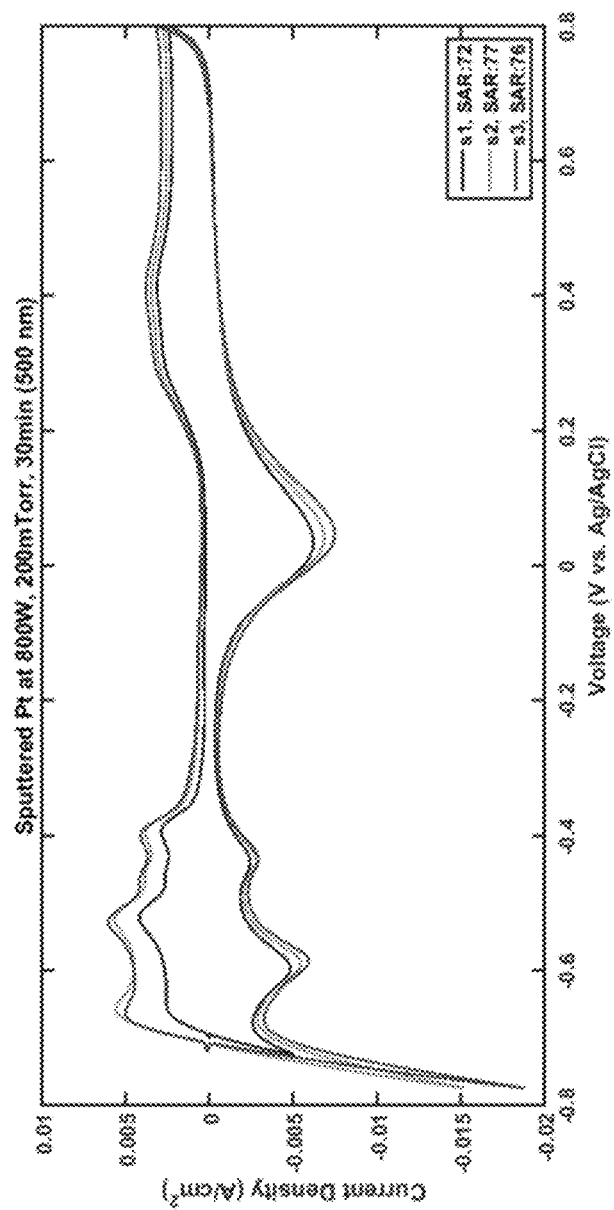
FIG. 12A plot current density as a function of voltage for Pt pillars sputtered using a power of 800 W, a pressure of 200 mTorr, and for a duration of 30 minutes (achieving a film thickness of 500 nm).
Figure 12B:
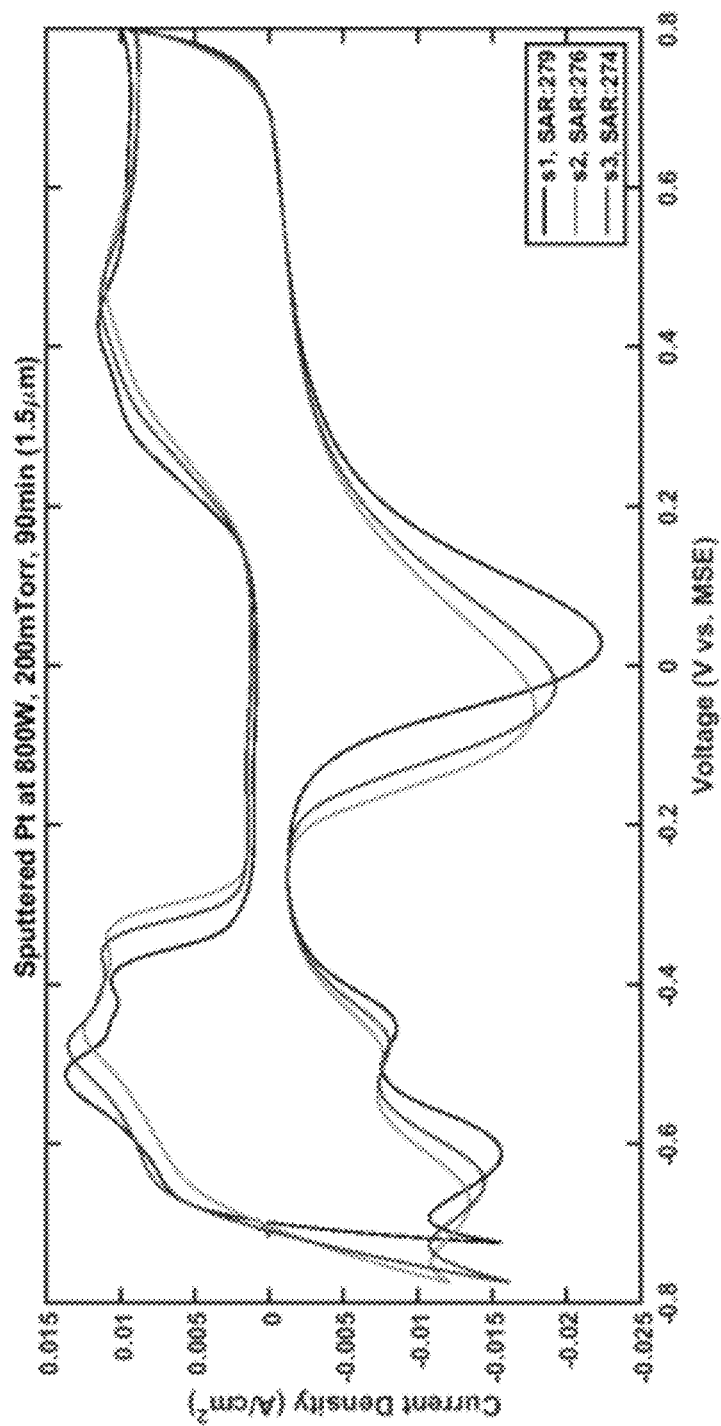
FIG. 12B plots current density as a function of voltage for Pt pillars sputtered using a power of 800 W, a pressure of 200 mTorr, and for a duration of 90 minutes (achieving a film thickness of 1.5 microns).

FIG. 12A and FIG. 12B illustrate capacitance-voltage measurements for sputtered Pt pillar structures having various SAR. In one or more embodiments, the sputtered Pt pillars are characterized by CV similar to that of Pt black formed by an electrodeposition method.

Figure 12C:
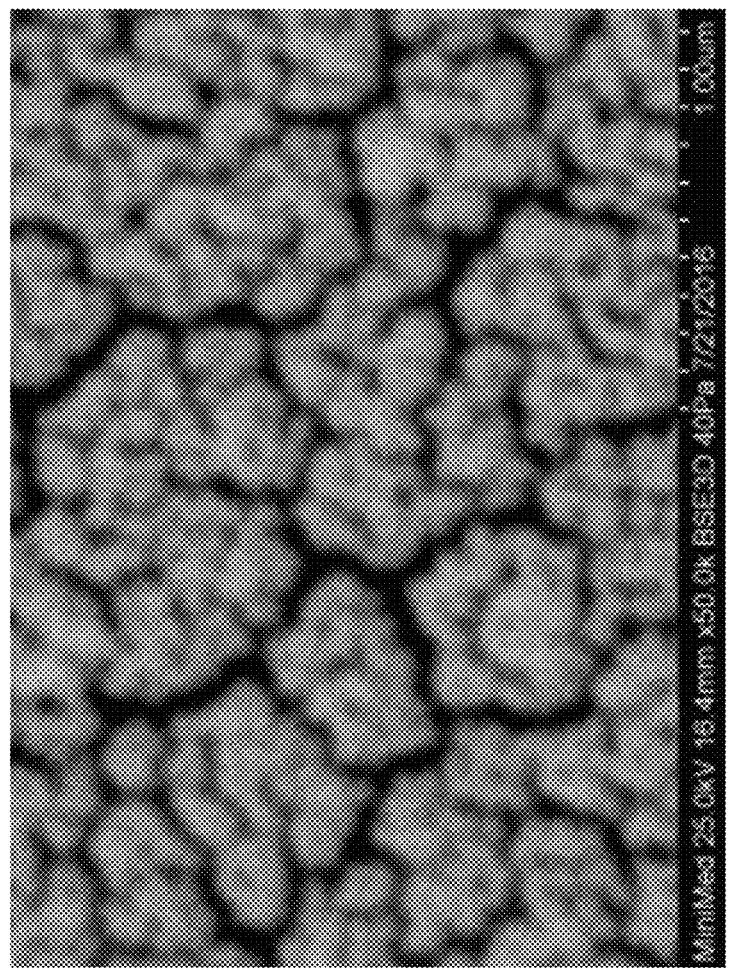
Figure 13A:
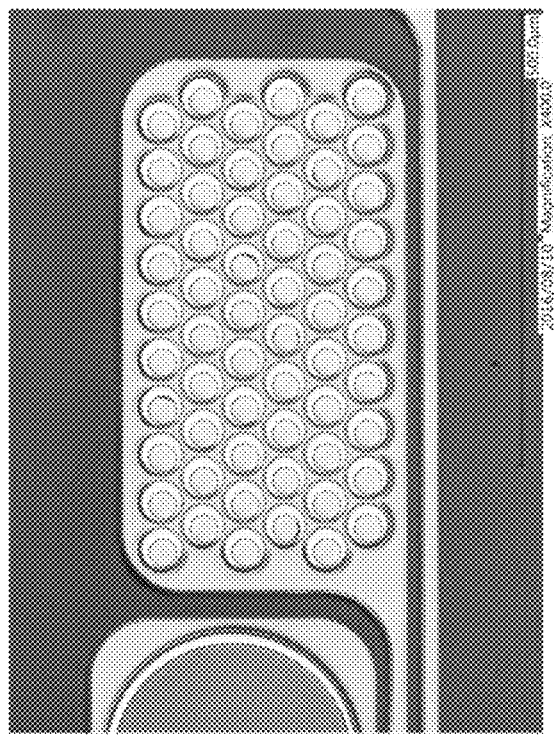
FIGS. 13A-13D illustrate micropatterning of Pt pillars by liftoff, wherein FIG. 13A has an offset of 10 micrometers, FIG. 13B has an offset of 2.5 micrometers, FIG. 13C has a 0 micron offset.
Figure 13B:
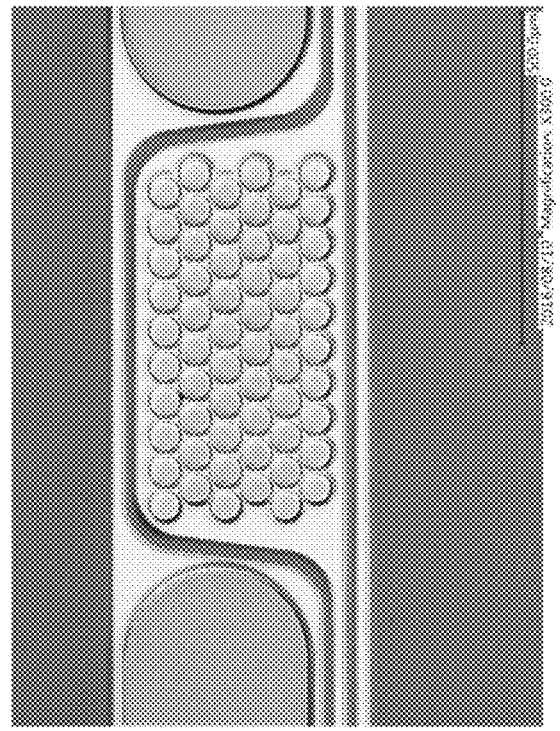
Figure 13D:
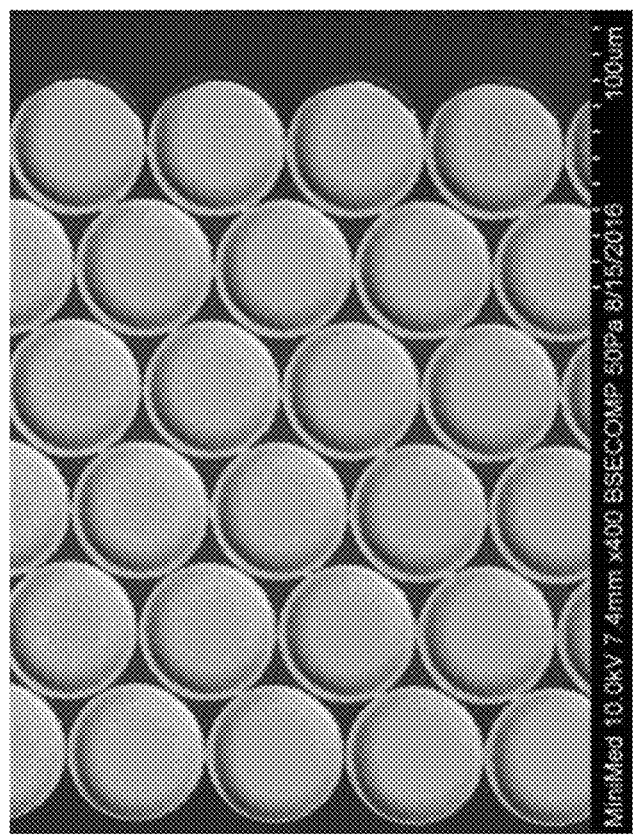
Figure 13C:
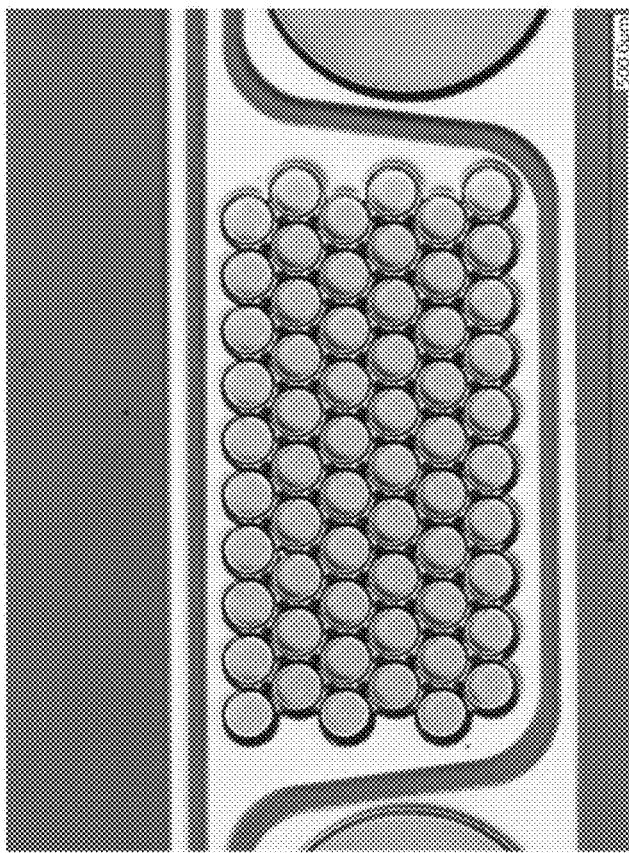

FIG. 12C illustrates the surface morphology measured for the structure measured in FIG. 12B (average SAR=275).

Example 3: Micropatterning

Micropatterned Pt pillars were achieved by lithographically patterning a 15 micrometer thickness of AZ6420 photoresist on a substrate, forming a dark field mask. Pt metal was sputtered onto the mask and substrate using sputtering conditions including 800 W power and 200 mTorr pressure, resulting in a 1.5 micron thickness of Pt deposited on the mask and the substrate. Liftoff of the mask was achieved using sonication in acetone, resulting in the micropatterned Pt shown in FIGS. 13A-13D. In one or more embodiments, sputtering and liftoff does not require additional tools or materials.

FIGS. 13A-13D illustrate micropatterning of Pt pillars by liftoff even for micron-thick films, wherein the 2.5 μm offset offers the best pattern in terms of microarray coverage versus misalignment tolerance.

Example 4: Downstream Compatibility

TABLE 3

SAR after immersion in solution for various materials.

| Solution | Time (min) | SAR (AVG) | SAR (SEM) |
|---|---|---|---|
| Pt black | 60 | 78.6 | 2.8 |
| Silver | 90 | 74.6 | 1.1 |
| Neg. Ctrl | 0 | 76.9 | 3.0 |

Figure 14:
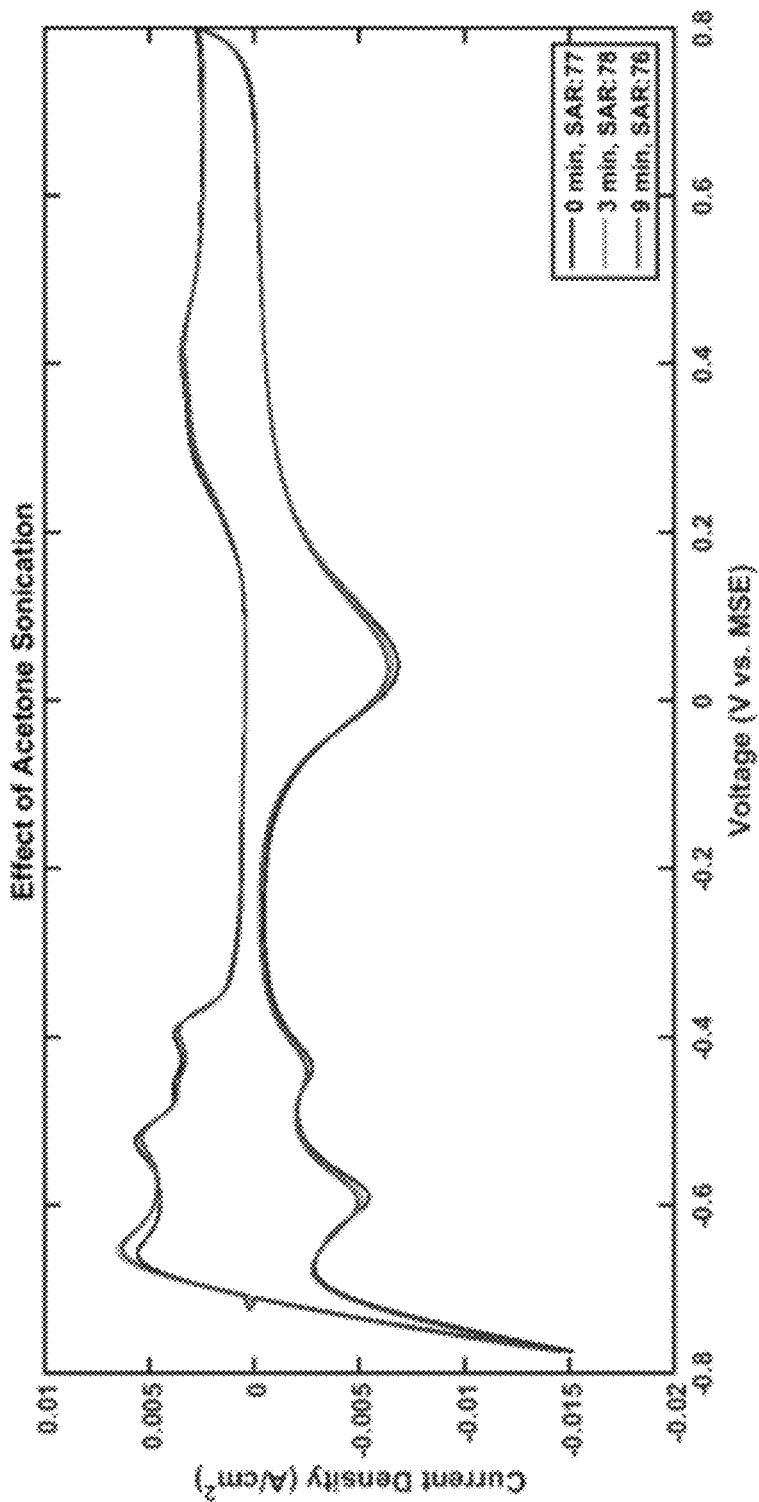
FIG. 14 plots current density as a function of voltage for sputtered Pt pillars after acetone sonication.

FIG. 14 shows no appreciable change to SAR after sonication in acetone.

Figure 15:
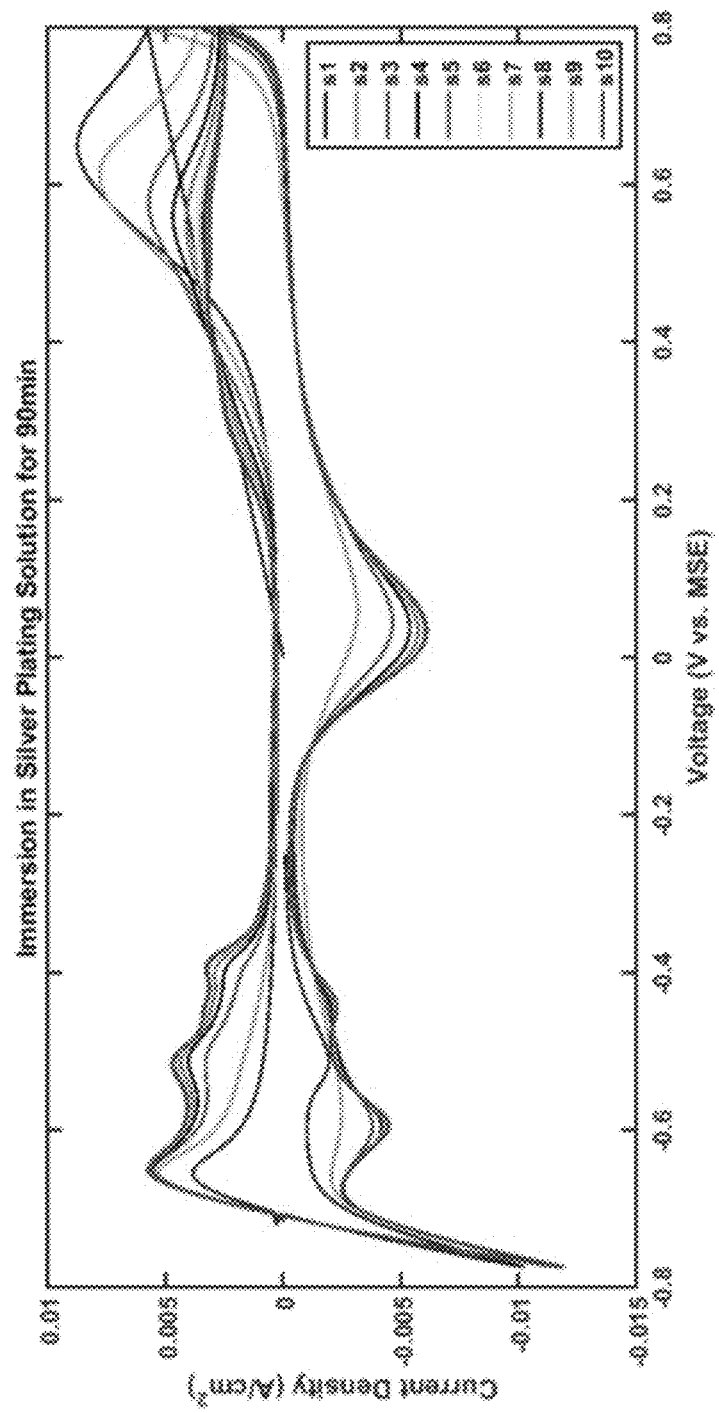
FIG. 15 plots current density as a function of voltage for sputtered Pt pillars after immersion in silver plating solution for 90 minutes.

FIG. 15 shows CV resumed typical Pt behavior after 2-3 cycles of conditioning comprising immersion in silver plating solution for 90 minutes (RE plating).

Figure 16:
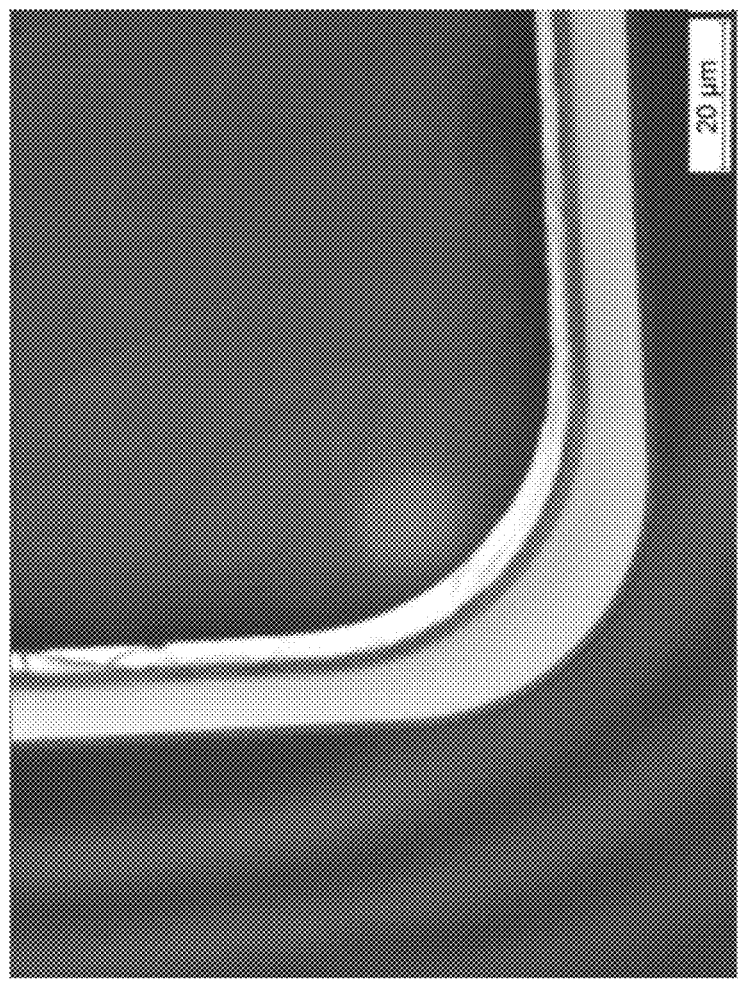
FIG. 16 shows no observable loss of adhesion or cracking even at the corners.

FIG. 16 shows no observable loss of adhesion or cracking even at the corners, maintaining sharp edges after RE plating.

Example 5: WE and CE Electrode Fabrication

Figures 17A, 17B:
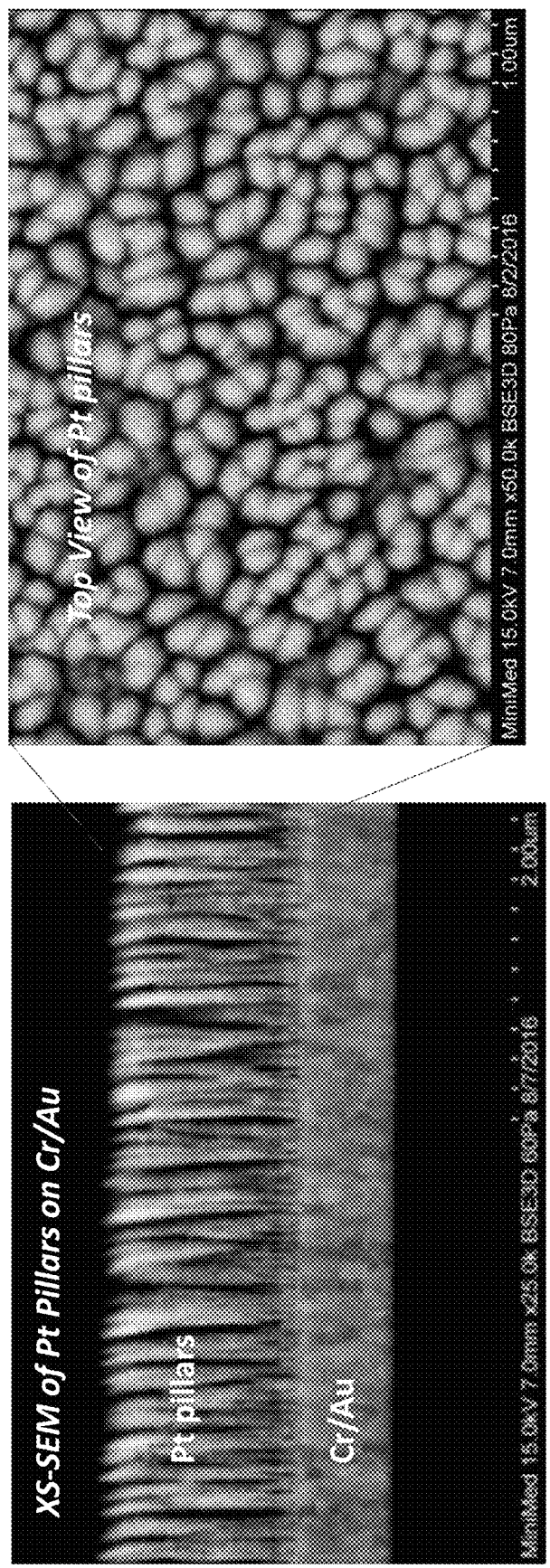

FIG. 17A-17B illustrates uniform film thickness was achieved using the sputtering technique on the CE electrode, wherein the Pt pillar morphology and good adhesion on Cr/Au layer are maintained throughout processing. Moreover, the Pt pillars do not cover sidewalls or extend beyond insulation layer, providing more uniformity to subsequent chemistry.

Figure 17C:
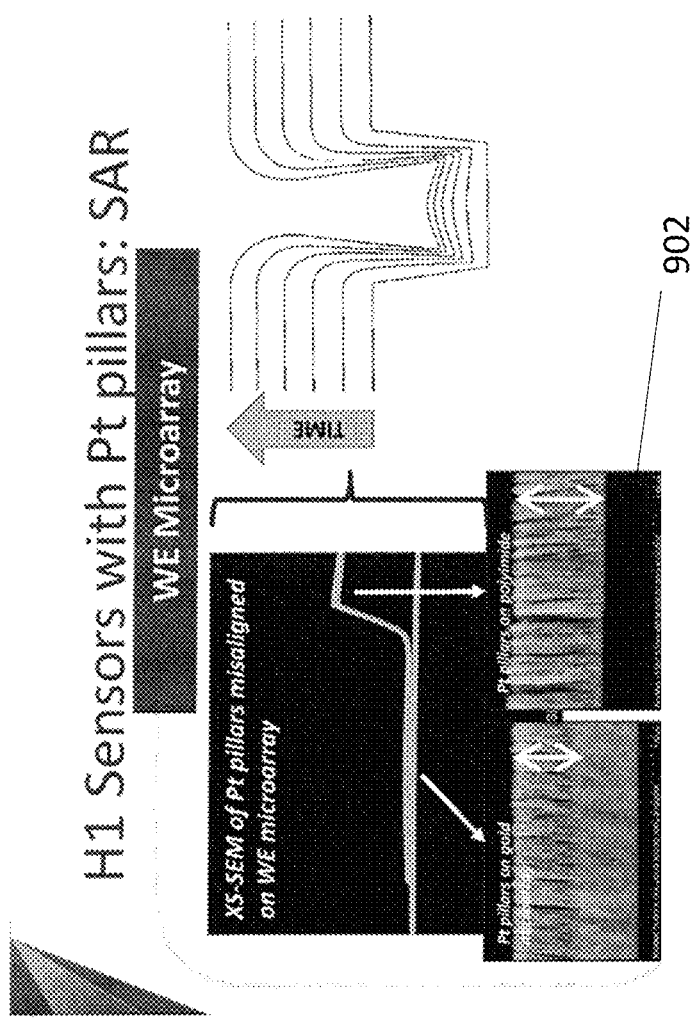
FIG. 17C shows Pt pillar morphology on the WE microarray.

FIG. 17C illustrates Pt pillar morphology on the WE microarray.

Figure 18A:
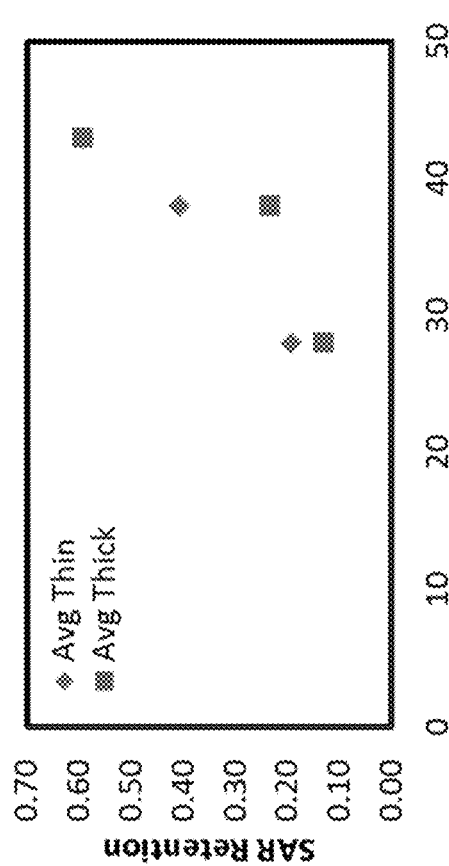
FIG. 18A plots SAR retention as a function of microarray diameter.
Figure 18B:
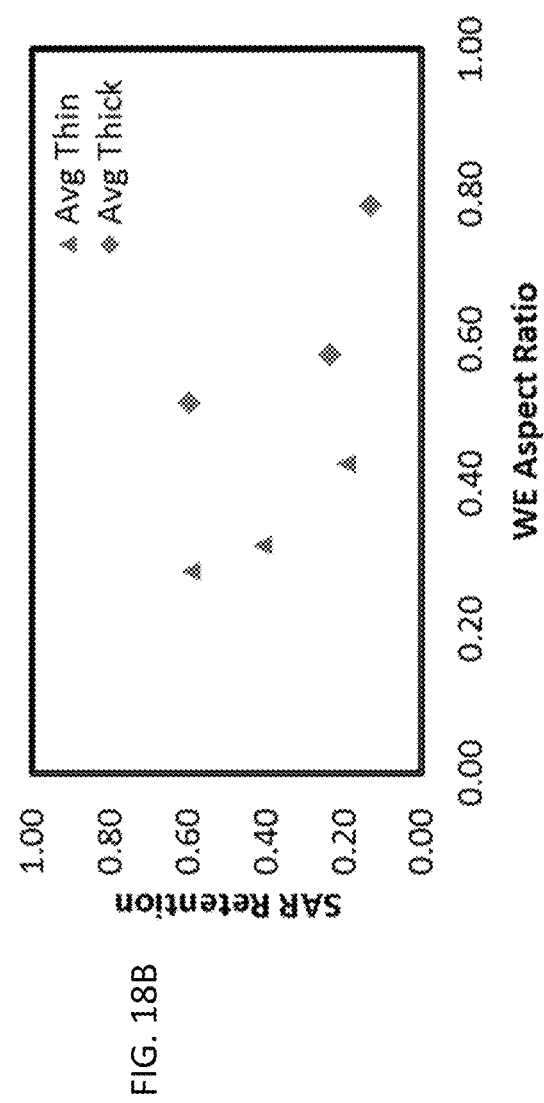
FIG. 18B plots SAR retention as a function of WE aspect ratio.

The SAR on the WE and CE differ due to shadowing effects. FIG. 18A and FIG. 18B shows the WE microarray features high aspect ratio and results in thinner films with lower SAR. However, equal or higher SAR is desired for the CE.

Example 5: Sensor Results for Low SAR (Plate 1)

TABLE 4

| Glucose (mg/dL) | Oxygen (%) | Duration (h:mm) |
|---|---|---|
| 100 | 5 | 2:00 |
| 200 | 5 | 1:00 |
| 400 | 5 | 1:00 |
| 400 | 1 | 1:00 |
| 0 | 5 | 1:00 |
| 100 | 5 | 1:00 |
| 400 | 5 | 15:50 |
| 400 | 0.1 | 2:00 |

Figure 19A:
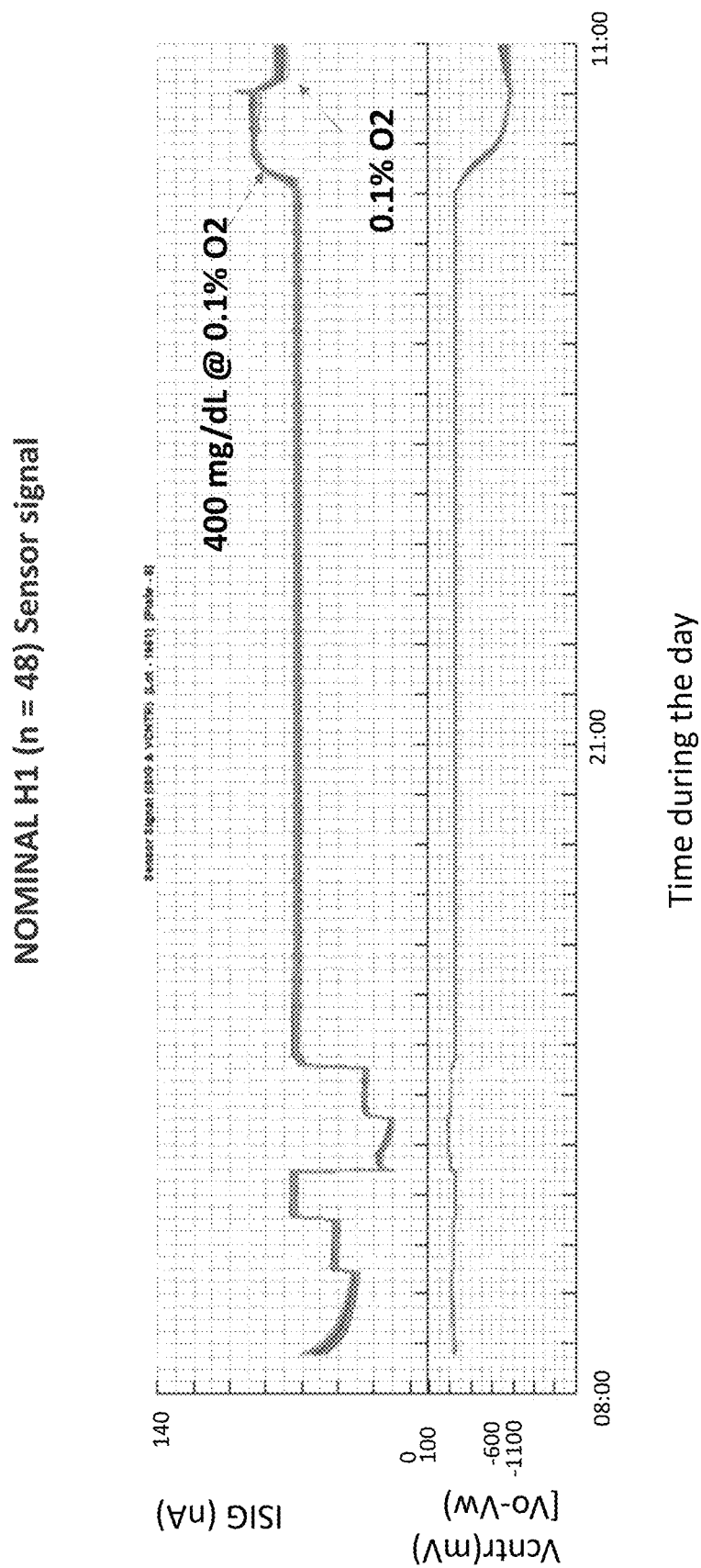
FIG. 19A plots fBTS data (plate 1) for a nominal electroplated electrode with low SAR.
Figure 19B:
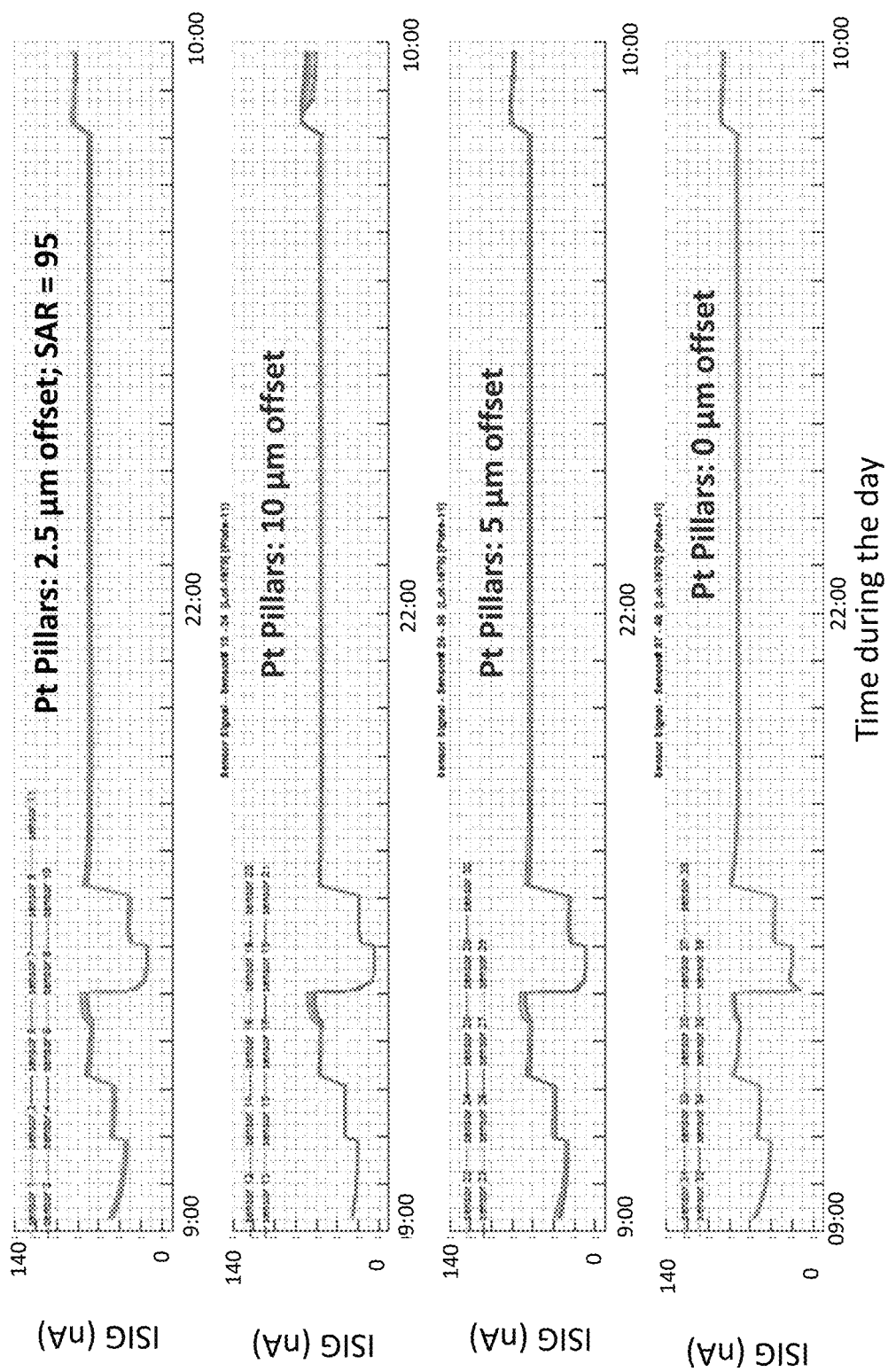
FIG. 19B plots fBTS data (plate 1) from Pt electrodes made using sputtering and with different offsets, wherein the sensor has the low SAR.

FIG. 19A-19B illustrate lower SAR shows similar Isig to nominal H1 and faster run-in time (nominal run taken separately). The 0.1% $O_2$ highlights when the sensor design has insufficient platinum for $G_{ox}$.

Figure 20:
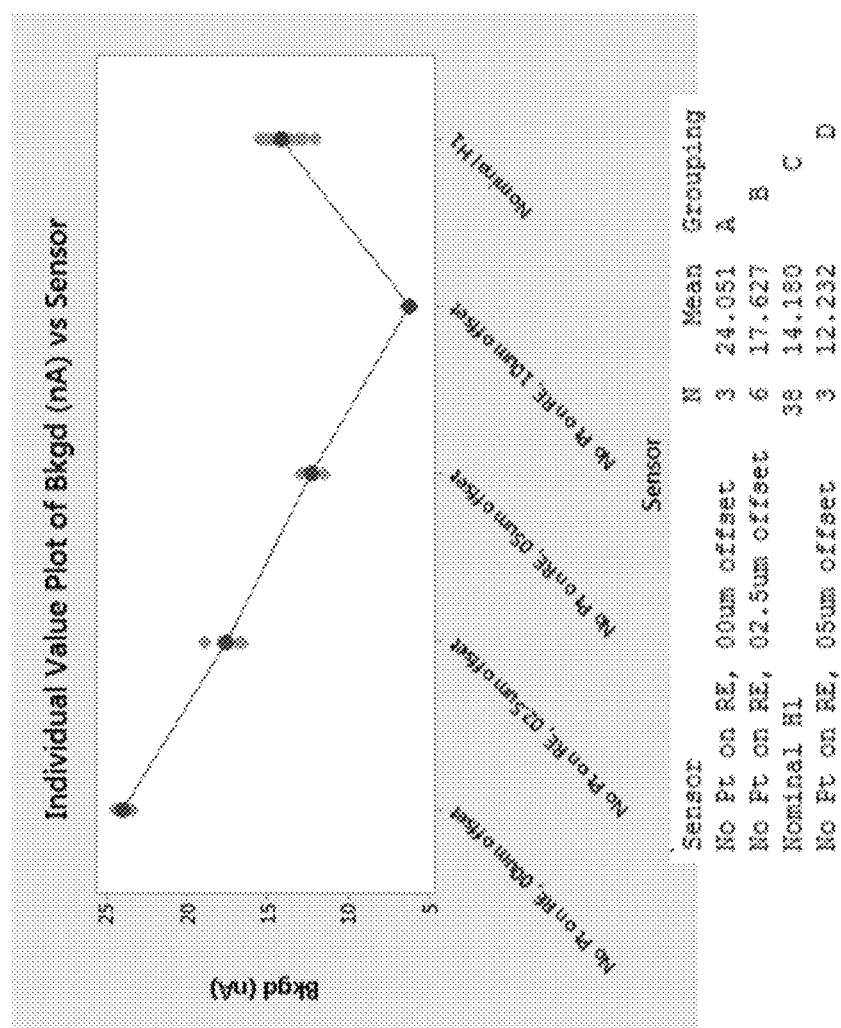
FIG. 20 plots background (bkgd, nA) for various sputtered sensors and a nominal (electroplated) sensor, for low SAR, where RE is reference electrode.

FIG. 20 illustrates the background is proportional to the size of Pt pillar microarrays, the background current is comparable to H1 for 5 μm offset sensors, and the greatest variability (but larger n) in background is for the sensor with nominal H1.

Figure 21:
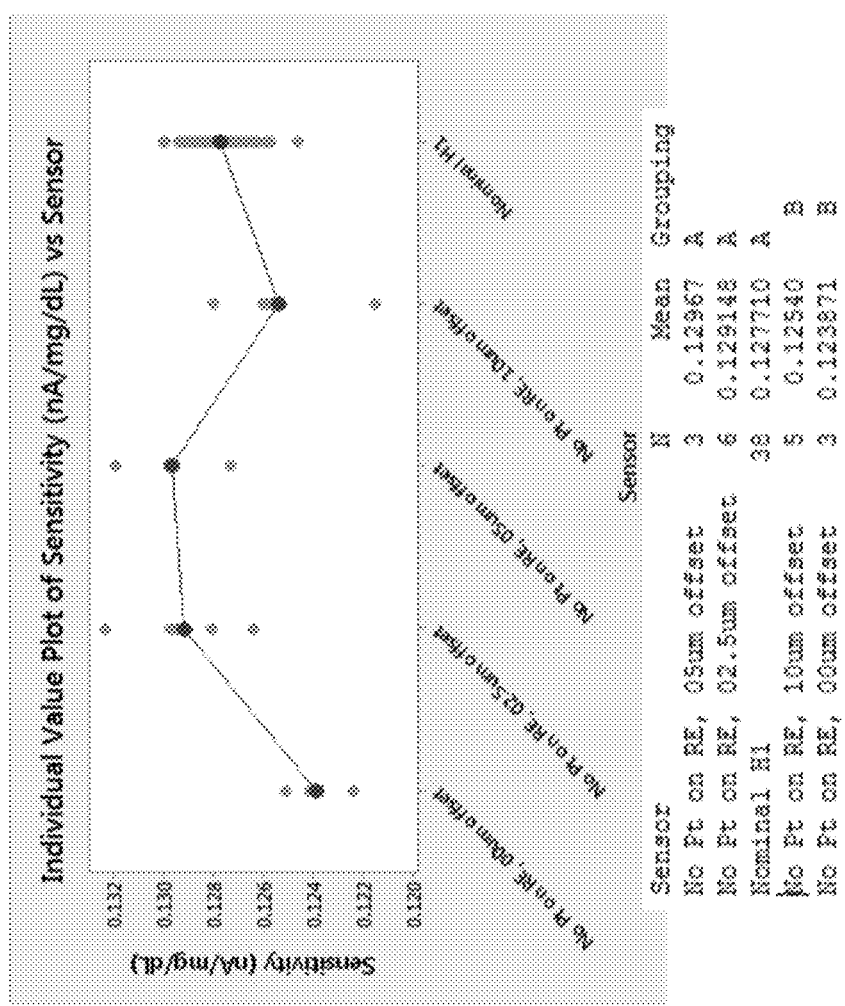
FIG. 21 plots sensitivity (nA/mg/dl) for various sputtered sensors and a nominal (electroplated) sensor, wherein the sensors have low SAR.

FIG. 21 illustrates similar sensitivity despite varying SAR (0.12 nA/mg/dL). The indicates that overshooting SAR does not provide benefits (high SAR is not necessary for operation in reaction-limited regime).

Figure 22:
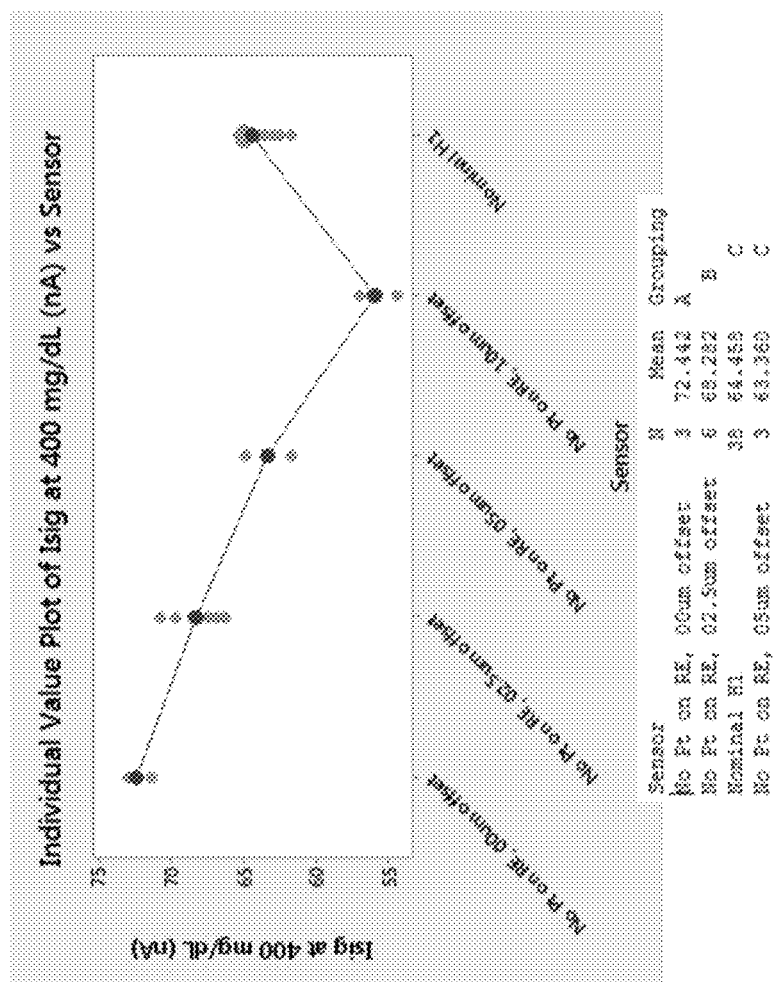
FIG. 22 plots Isig for various sputtered sensors and a nominal (electroplated) sensor, wherein the sensors have low SAR.

FIG. 22 plots Isig for various sputtered sensors and a nominal (electroplated) sensor, wherein the sensors have low SAR.

Figure 23:
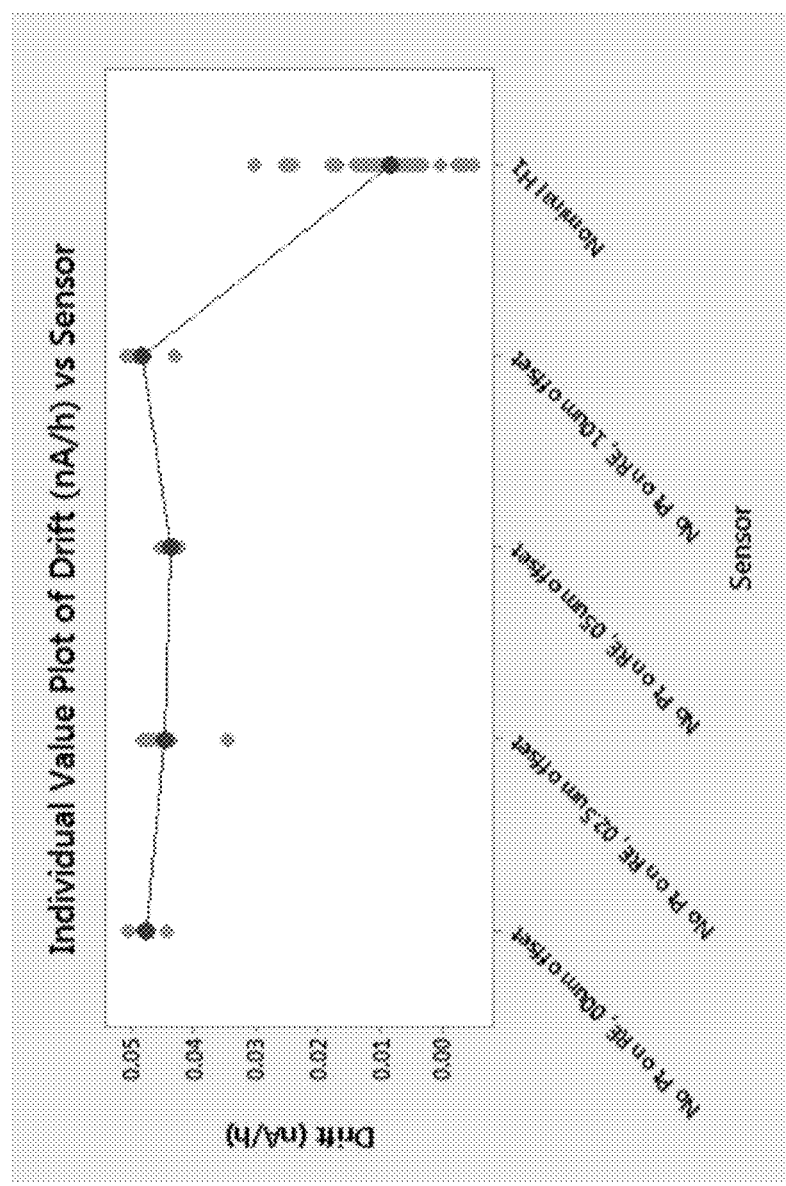
FIG. 23 plots drift for various sputtered sensors and a nominal (electroplated) sensor, wherein the sensors have low SAR.

FIG. 23 illustrates consistent drift is observed with all Pt pillar sensors. This is a statistically higher drift, but is practically insignificant (0.6 nA in 12 h) and may potentially be a testing artifact. The oxygen response is less than or equal to that of a nominal H1 sensor.

Figure 24:
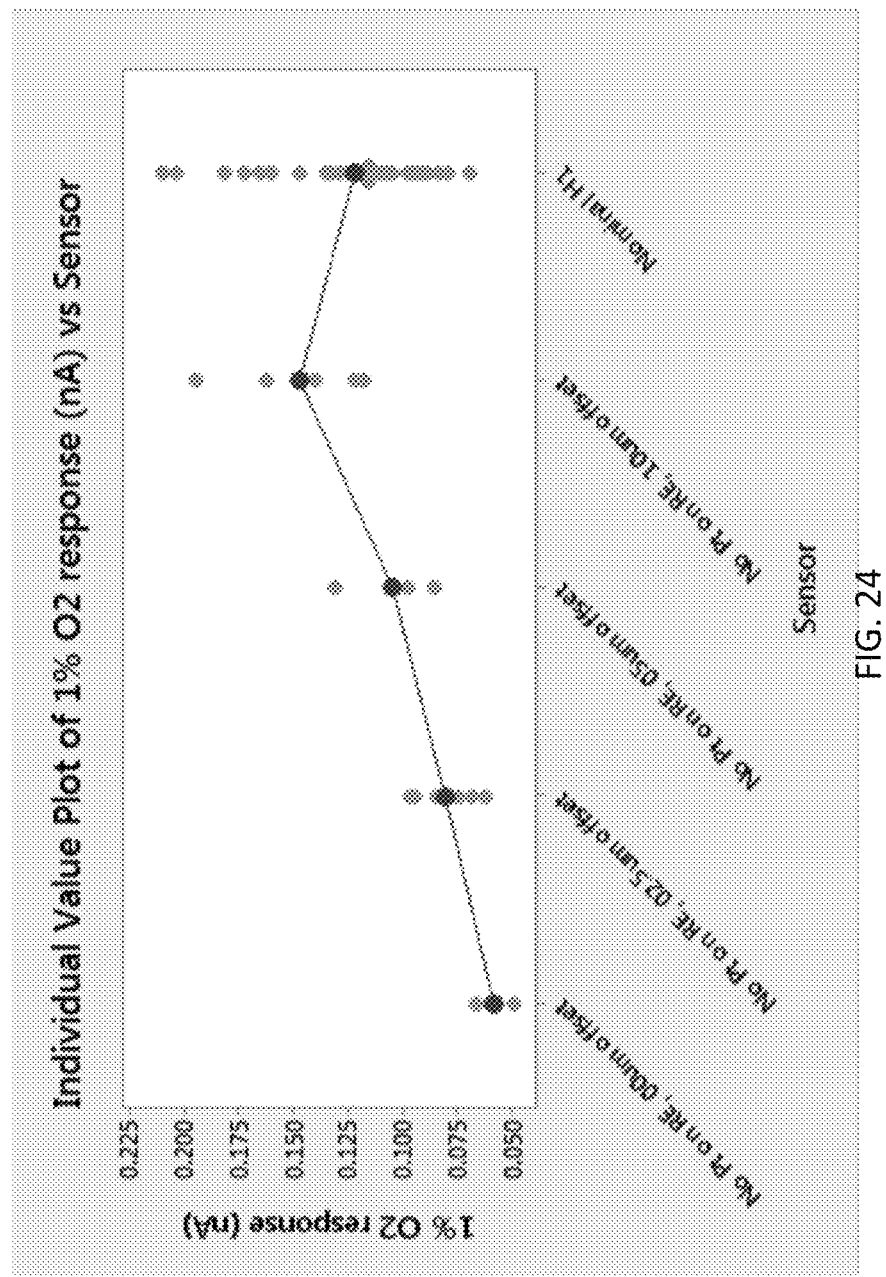
FIG. 24 plots 1% oxygen response for various sputtered sensors and a nominal (electroplated) sensor, wherein the sensors have low SAR.

FIG. 24 plots 1% oxygen response for various sputtered sensors and a nominal (electroplated) sensor, wherein the sensors have low SAR.

Figure 25:
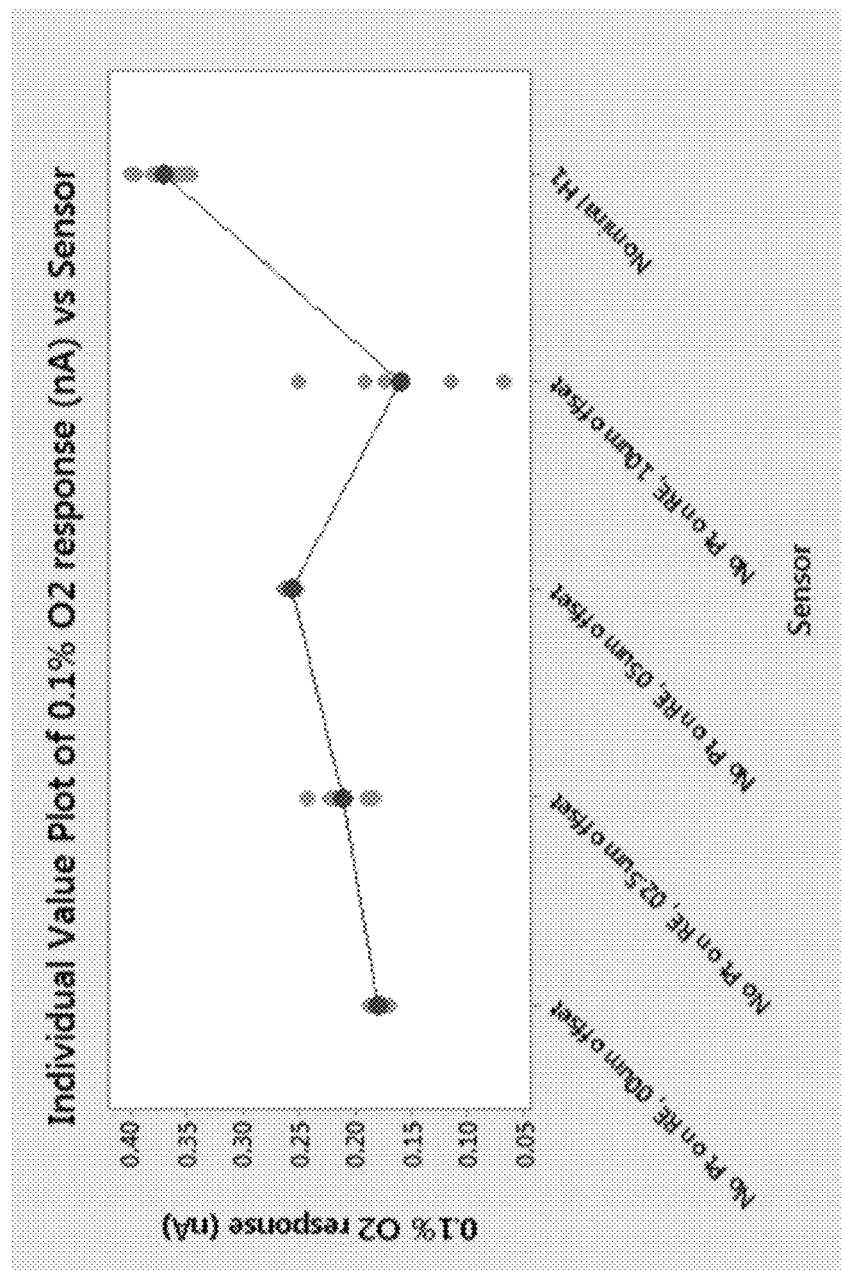
FIG. 25 plots 0.1% oxygen response for various sputtered sensors and a nominal (electroplated) sensor, wherein the sensors have low SAR.

FIG. 25 plots 0.1% oxygen response for various sputtered sensors and a nominal (electroplated) sensor, wherein the sensors have low SAR.

Example 5: Results for High SAR (Plate 2)

TABLE 5

| Glucose (mg/dL) | Oxygen (%) | Duration (h:mm) |
|---|---|---|
| 100 | 5 | 2:00 |
| 200 | 5 | 1:00 |
| 400 | 5 | 1:00 |
| 0 | 5 | 16:40 |
| 100 | 5 | 1:00 |
| 400 | 1.0 | 1:00 |
| 400 | 0.1 | 2:00 |

Figure 26A:
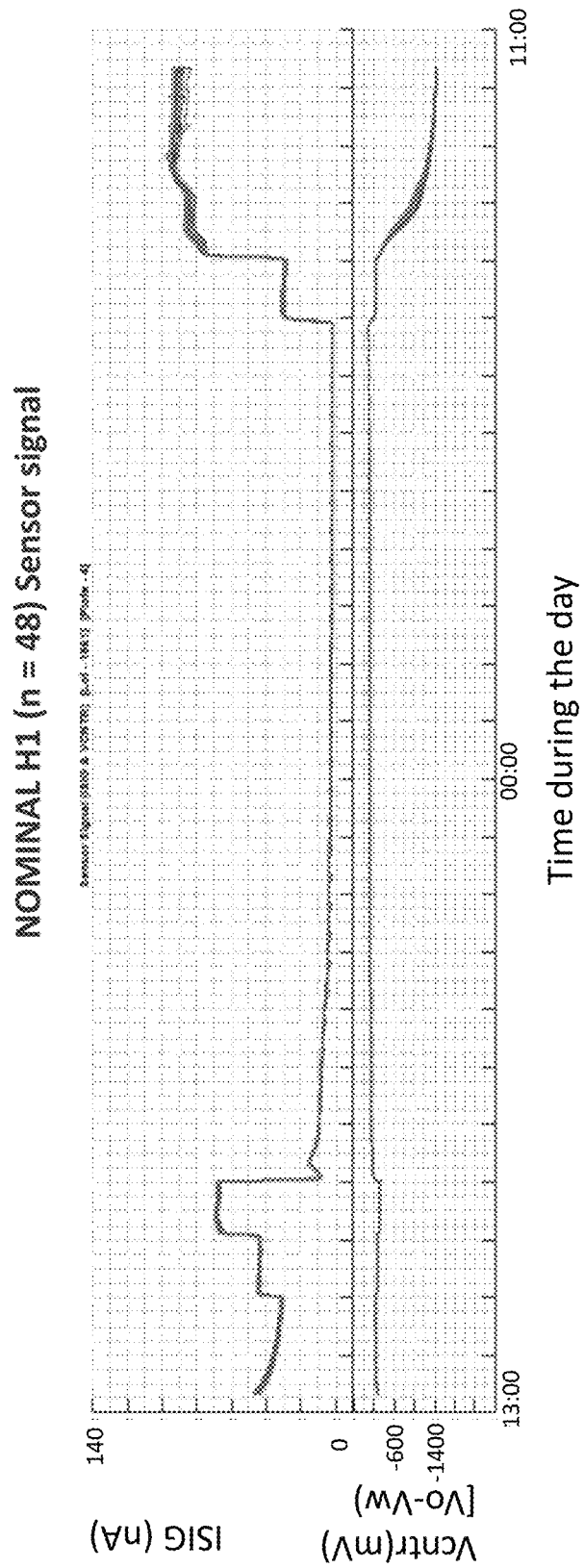
FIG. 26A plots fBTS data (plate 2) for a nominal electroplated electrode with high SAR.
Figure 26B:
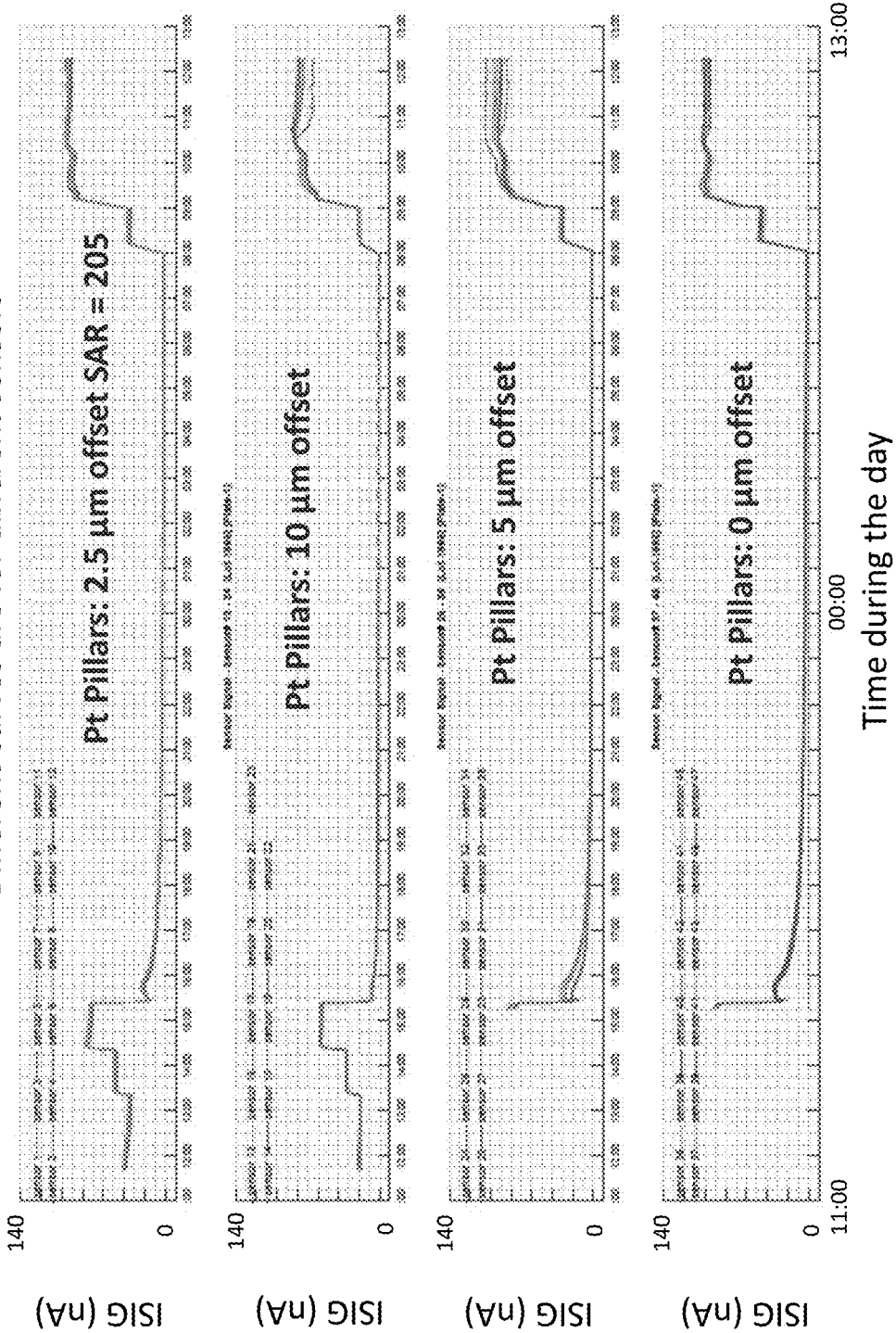
FIG. 26B plots fBTS data (plate 2) from Pt electrodes made using sputtering and with different offsets and for high SAR.

FIGS. 26A and 26B shows the run-in time for the sputtered device is shorter than for nominal H1 (approximately 1 hour for 2.5 μm offset). The data shows comparable oxygen response to nominal H1.

Figure 27:
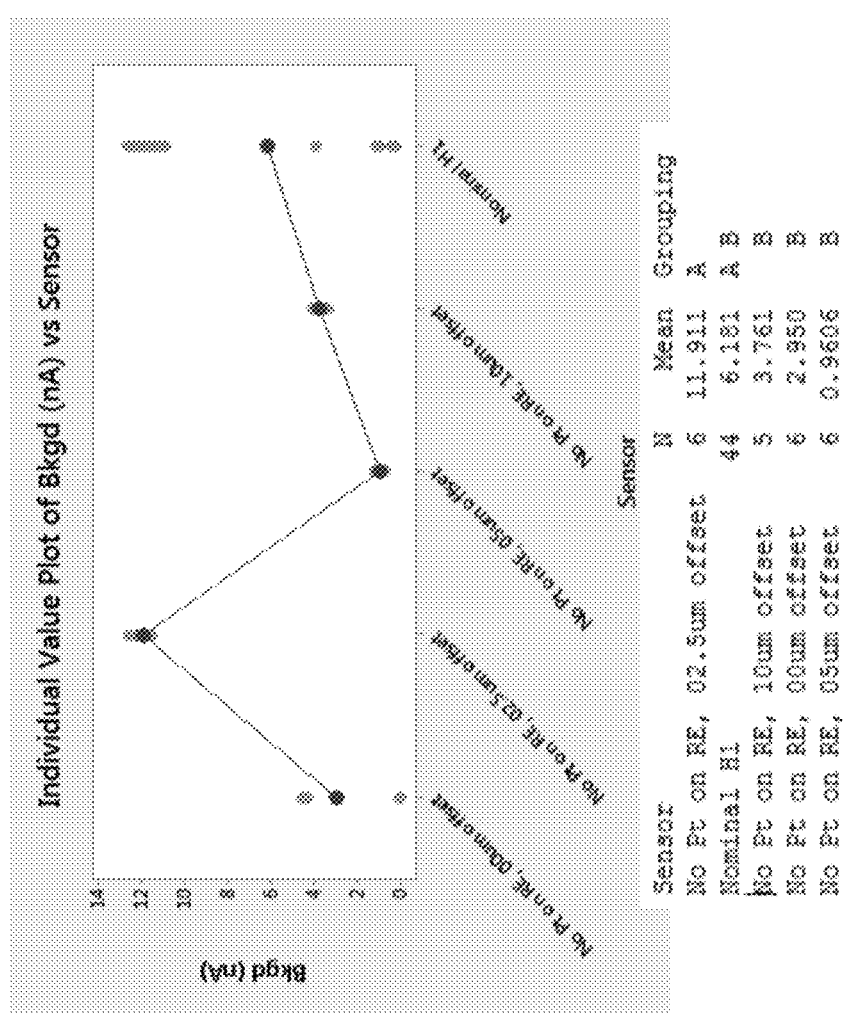
FIG. 27 plots background for various sputtered sensors and a nominal (electroplated) sensor, wherein the sensor has the high SAR.
Figure 28:
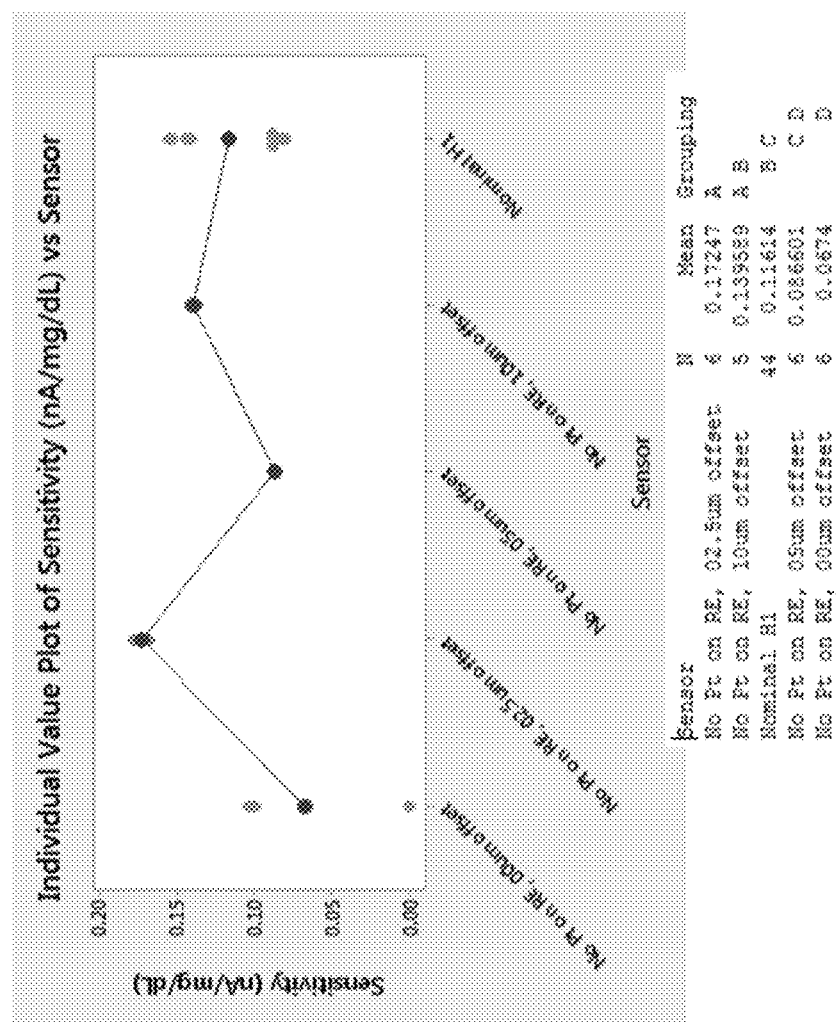
FIG. 28 plots sensitivity for various sputtered sensors and a nominal (electroplated) sensor, wherein the sensors have high SAR.

FIG. 27 and FIG. 28 illustrate the sputtered pillar devices have a background current and sensitivity that are comparable to the nominal H1 devices. Side A and side B delineations are not present with sputtered Pt pillars (all sensors are patterned in the same run). The highest sensitivity was achieved for the sensor having a 2.5-μm-offset (and was characterized by a similarly high background).

Figure 29:
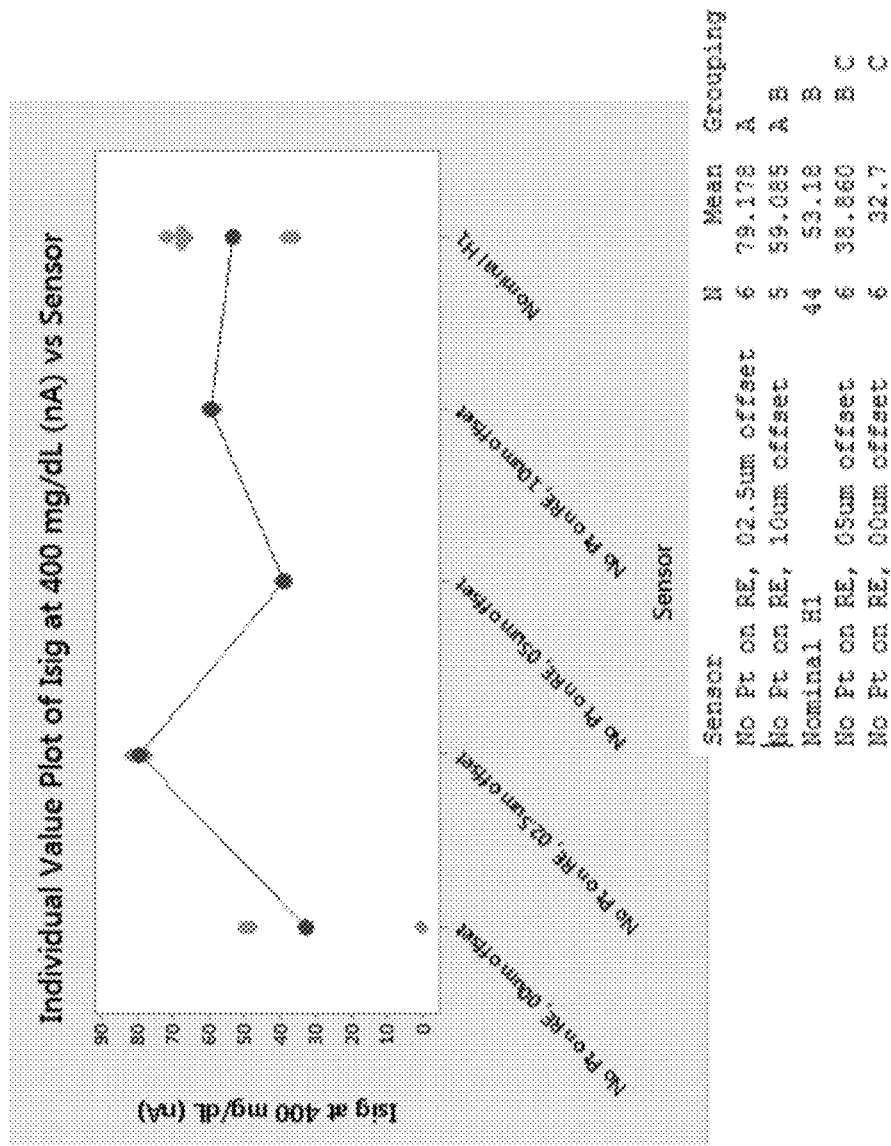
FIG. 29 plots Isig for various sputtered sensors and a nominal (electroplated) sensor, wherein the sensors have high SAR.

FIG. 29 plots Isig for various sputtered sensors and a nominal (electroplated) sensor, wherein the sensors have high SAR.

Figure 30:
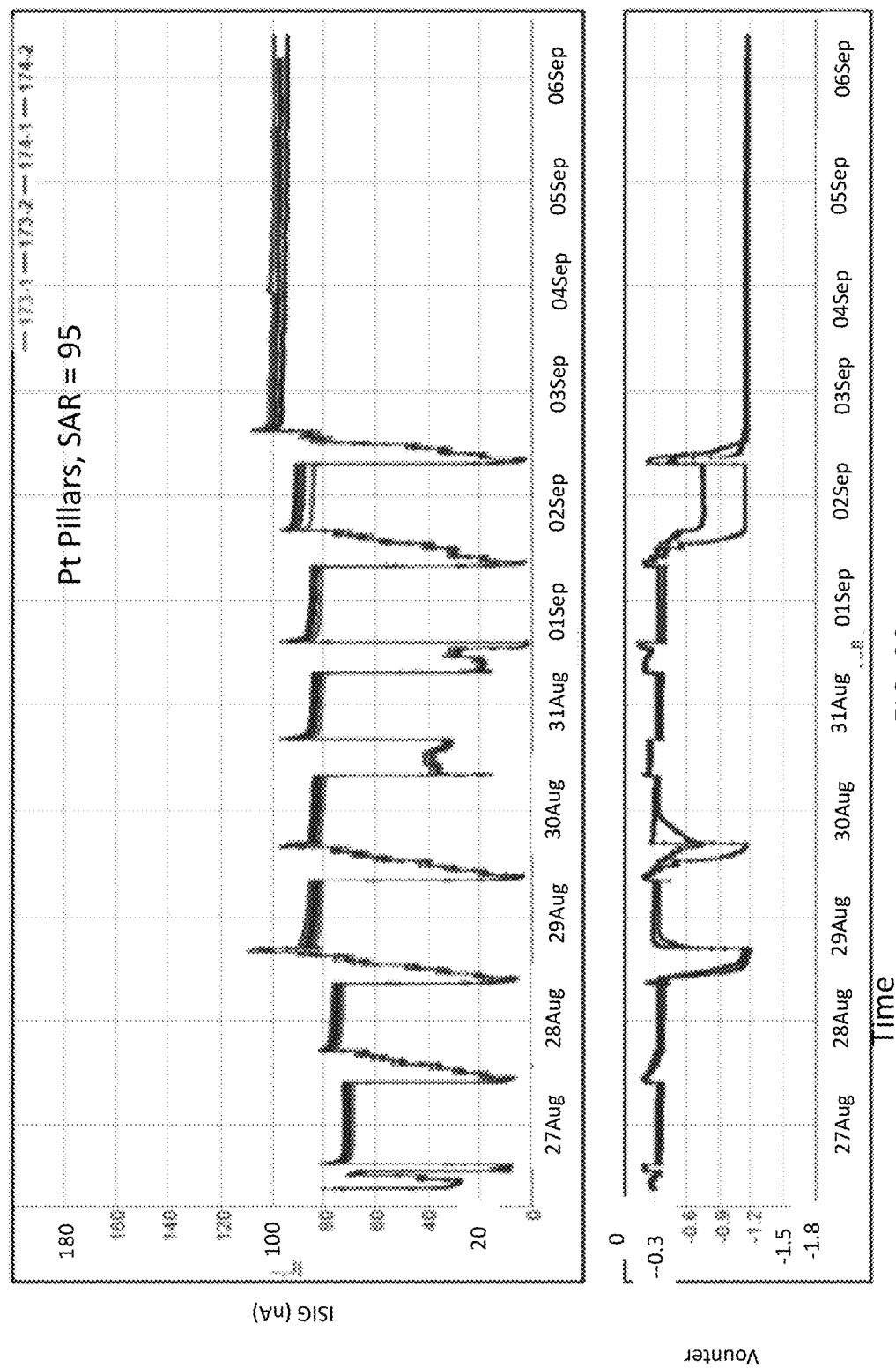
FIGS. 30 and 31 plot SITS data for electrodes comprising Pt pillars having SAR=95 and 250, respectively, as a function of time (date in August (xxAug) and date in September (xxSep) where xx is the day of the month).
Figure 31:
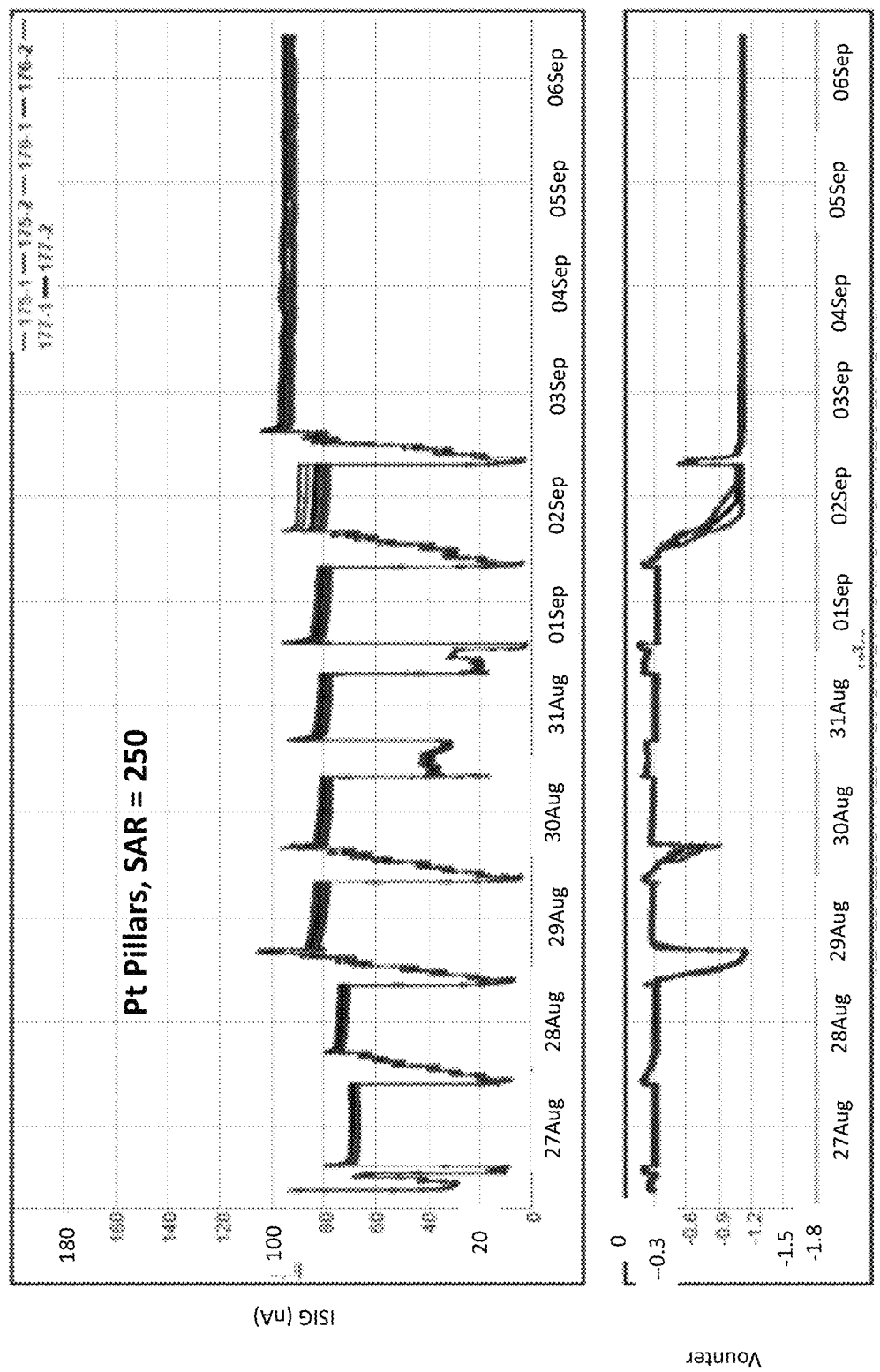

FIGS. 30 and 31 plot SITS data for electrodes comprising Pt pillars having SAR=95 and 250, respectively, as a function of time (date in August (xxAug) and date in September (xxSep) where xx is the day of the month).

Figure 32:
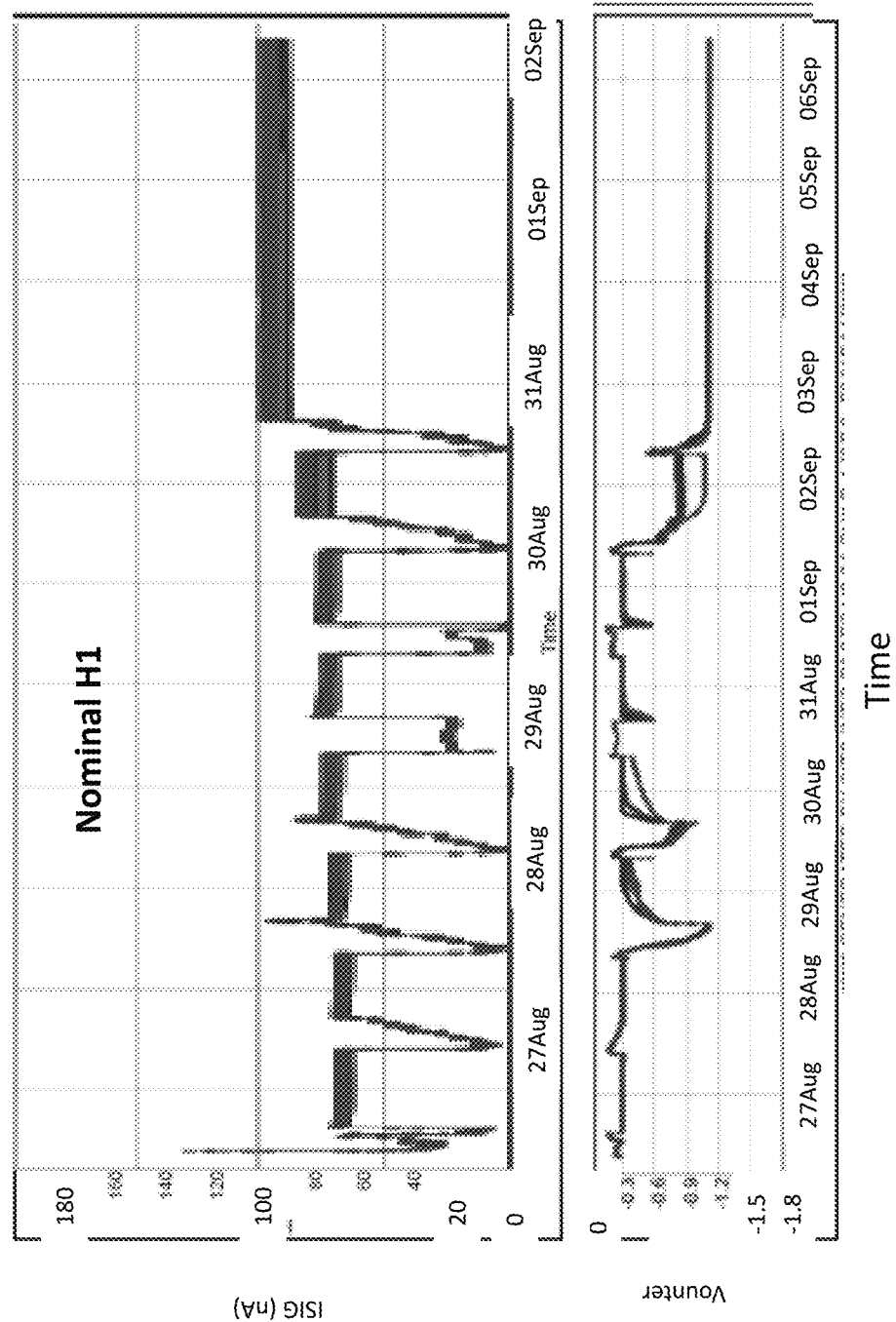
FIG. 32 plots SITS data for a nominal H1 (Harmony 1) electroplated electrode, as a function of time (date in August (xxAug) and date in September (xxSep) where xx is the day of the month).

FIG. 32 plots SITS data for a nominal H1 (Harmony 1) electroplated electrode, as a function of time (date in August (xxAug) and date in September (xxSep) where xx is the day of the month).

Example 6: Sits Results

TABLE 6

SITS data

| Metric | Unit | Mean | | | Tukey Pairwise Comparison | | |
|---|---|---|---|---|---|---|---|
| | | Nominal H1 | Pt Pillars | Pt Pillars SAR = 250 | Nominal H1 | Pt Pillars | Pt Pillars SAR = 250 |
| Linearity @ 5% O2, Day 1 | $R^2$ | 0.997 | 0.982 | 0.975 | A | B | C |
| Linearity @ 0.1% O2, Day 6 | $R^2$ | 0.995 | 0.979 | 0.976 | A | B | B |
| 1% O2 Response | %-Diff | 13.6 | 16.8 | 14.2 | A | A | A |
| 0.1% O2 Response | %-Diff | 34.6 | 33.8 | 33.3 | A | A | A |
| Temperature, 40 C. | %-Diff | −1.95 | −2.02 | −2.02 | A | A | A |
| Acetominophen, 0.1% | %-Diff | 15.0 | 6.4 | 5.1 | A | B | C |
| Acetominophen, 1.0% | %-Diff | 119 | 52.5 | 46.4 | A | B | B |
| Stability, Day 1 | %-Diff | 2.29 | 7.97 | 8.65 | A | B | C |
| Stability, Day 3 | %-Diff | 2.74 | 2.03 | 1.79 | A | B | B |
| Stability, Day 6 | %-Diff | 21.0 | 12.3 | 9.9 | A | B | B |

The data shows the Pt pillar sensors have linearity, oxygen response, and temperature response that is comparable to the nominal H1 devices. The data further shows the Pt pillar sensors have >50% lower response to acetaminophen as compared to the nominal H1 sensors. The data further shows the Pt pillar sensors have higher stability after later days (days 3 and 6).

Example 7: Diabetic Dog Testing

Figure 33:
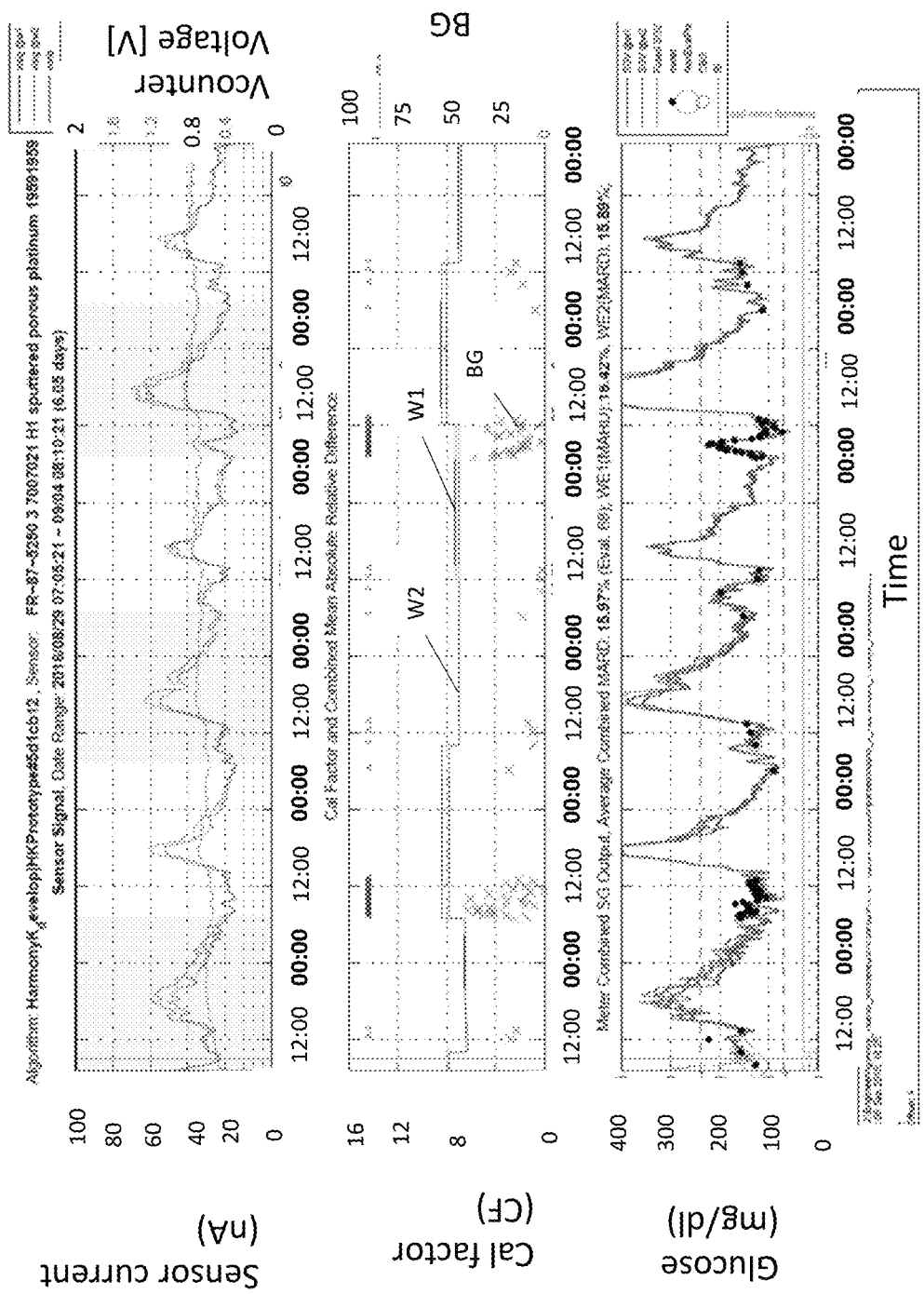
FIG. 33 shows sensor current, cal factor, and glucose as a function of time (24 hour clock) over a date range of 6.05 days for sensors comprising Pt pillars (Pt pillar SAR=250) and nominal H1 sensors implanted in a dog (W1=PT pillars sensor, W2=Nominal H1 sensor).

FIG. 33 shows sensor current, cal factor, and glucose as a function of time for sensors comprising Pt pillars (Pt pillar SAR=250) and nominal H1 sensors implanted in a dog. The data from measurements of 6 devices and using 2 dogs show similar performance in Isig, Cal Factor and MARD for the Pt pillar devices and the nominal H1 sensors. The Pt pillar devices exhibit stable CF and VCTR over time. This data evidences that Pt pillar sensors are a viable replacement to electroplated Pt in CGM sensors.

Figure 34:
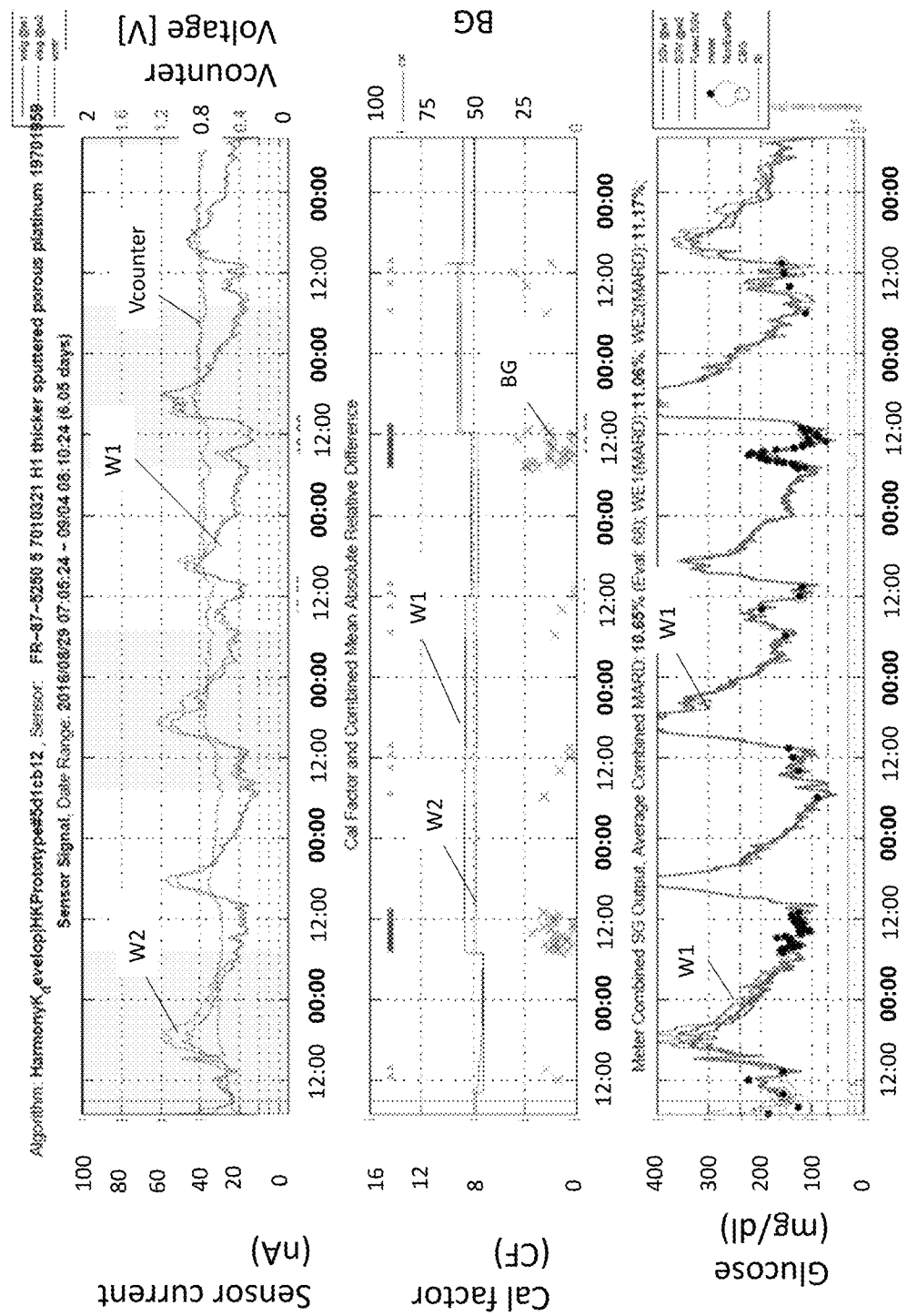
FIG. 34 shows sensor current, cal factor, and glucose as a function of time (24 hour clock) over a date range of 6.05 days for sensors comprising Pt pillars (Pt pillar SAR=95) and nominal H1 sensors implanted in a dog (W1=PT pillars, W2=Nominal H1).
Figure 35:
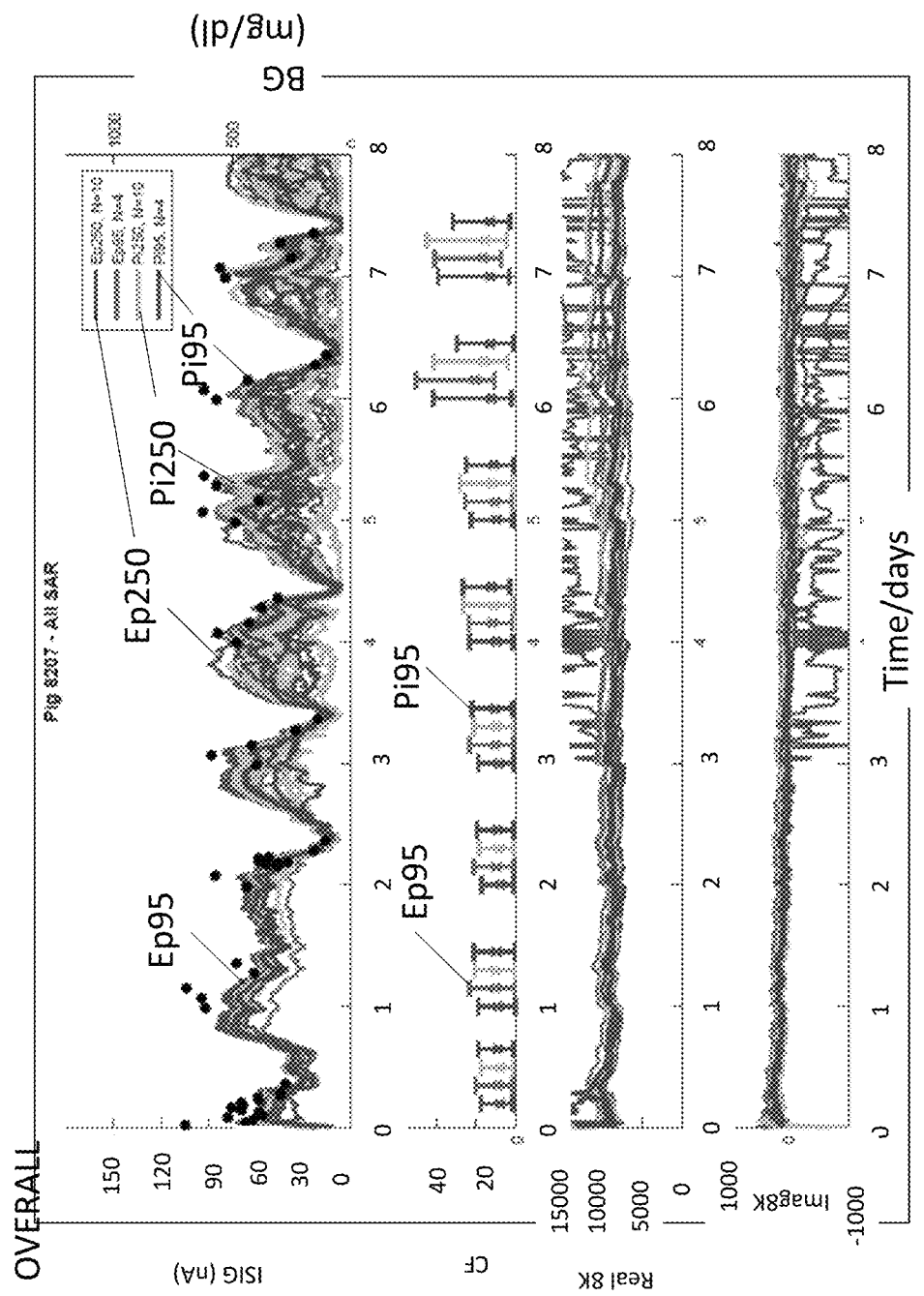
Figure 36:
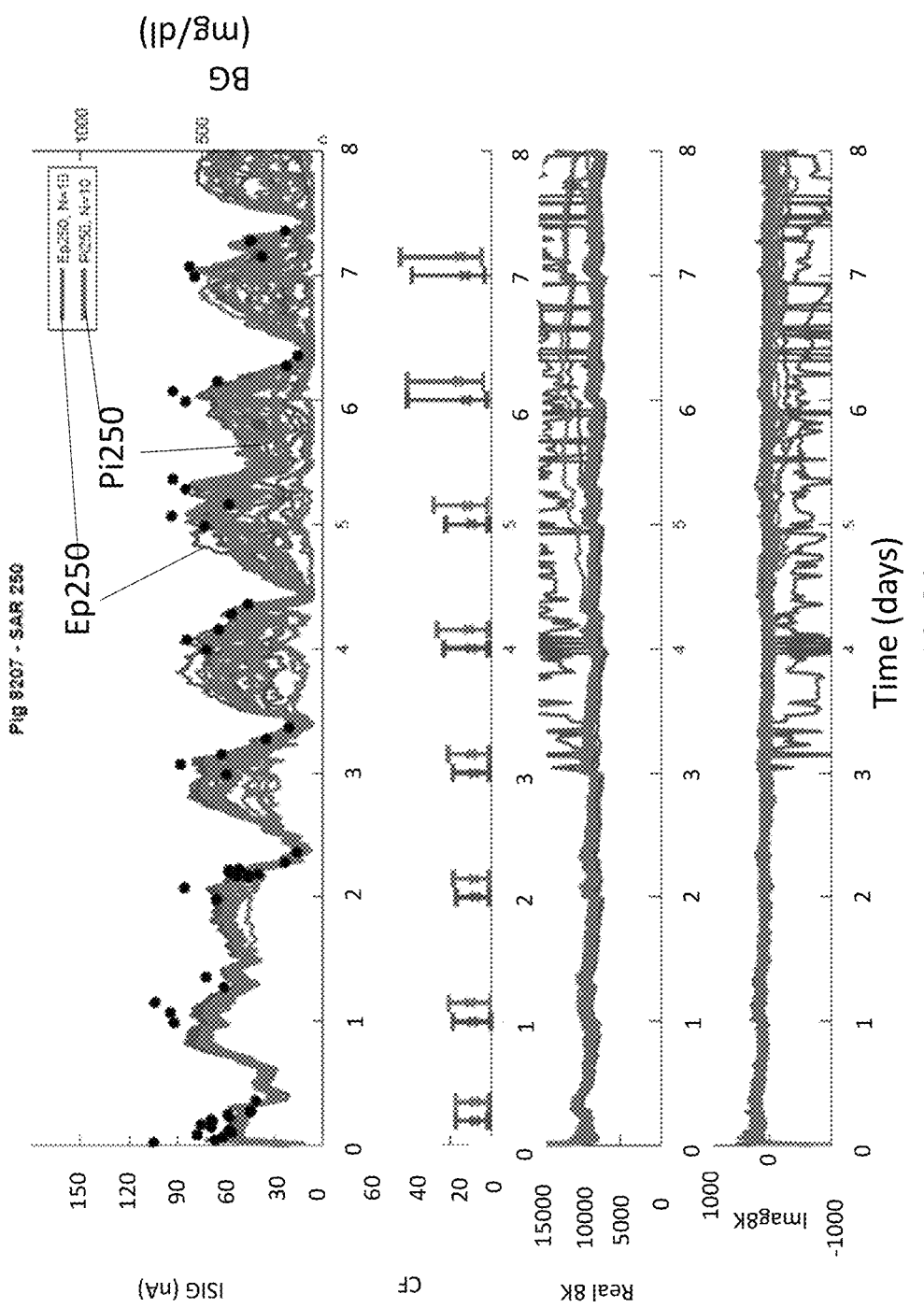
Figure 37:
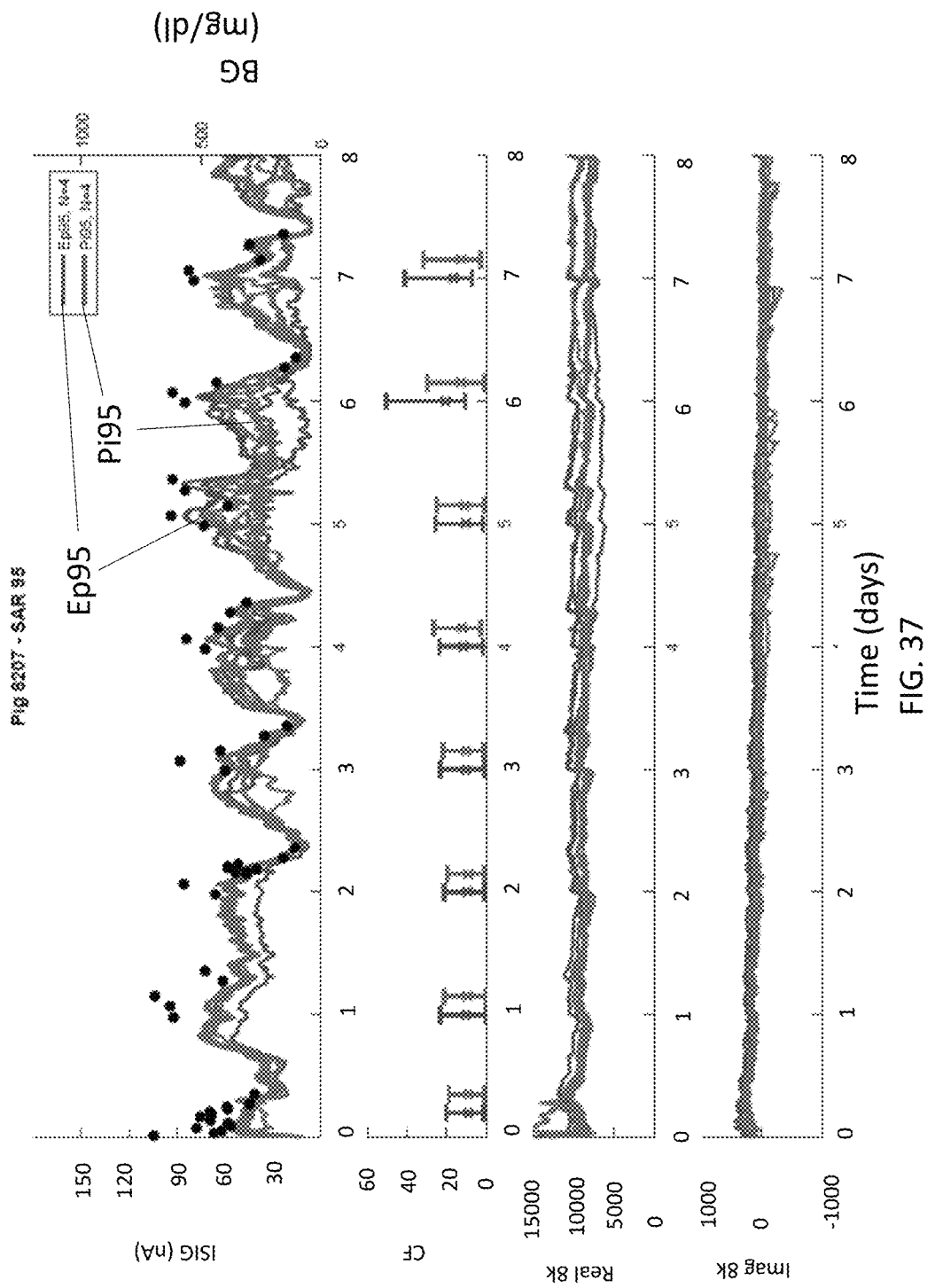
Figure 38:
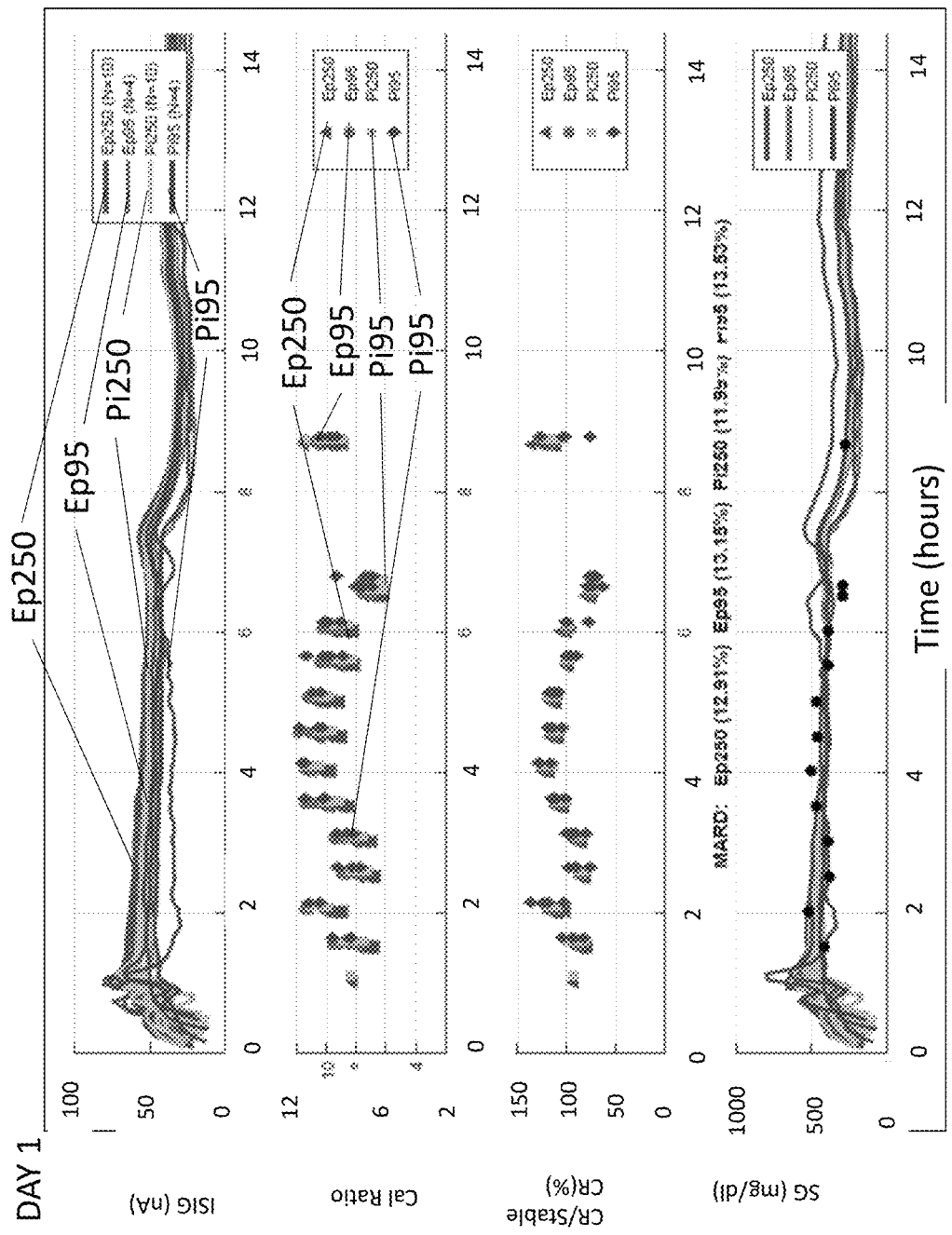
Figure 39:
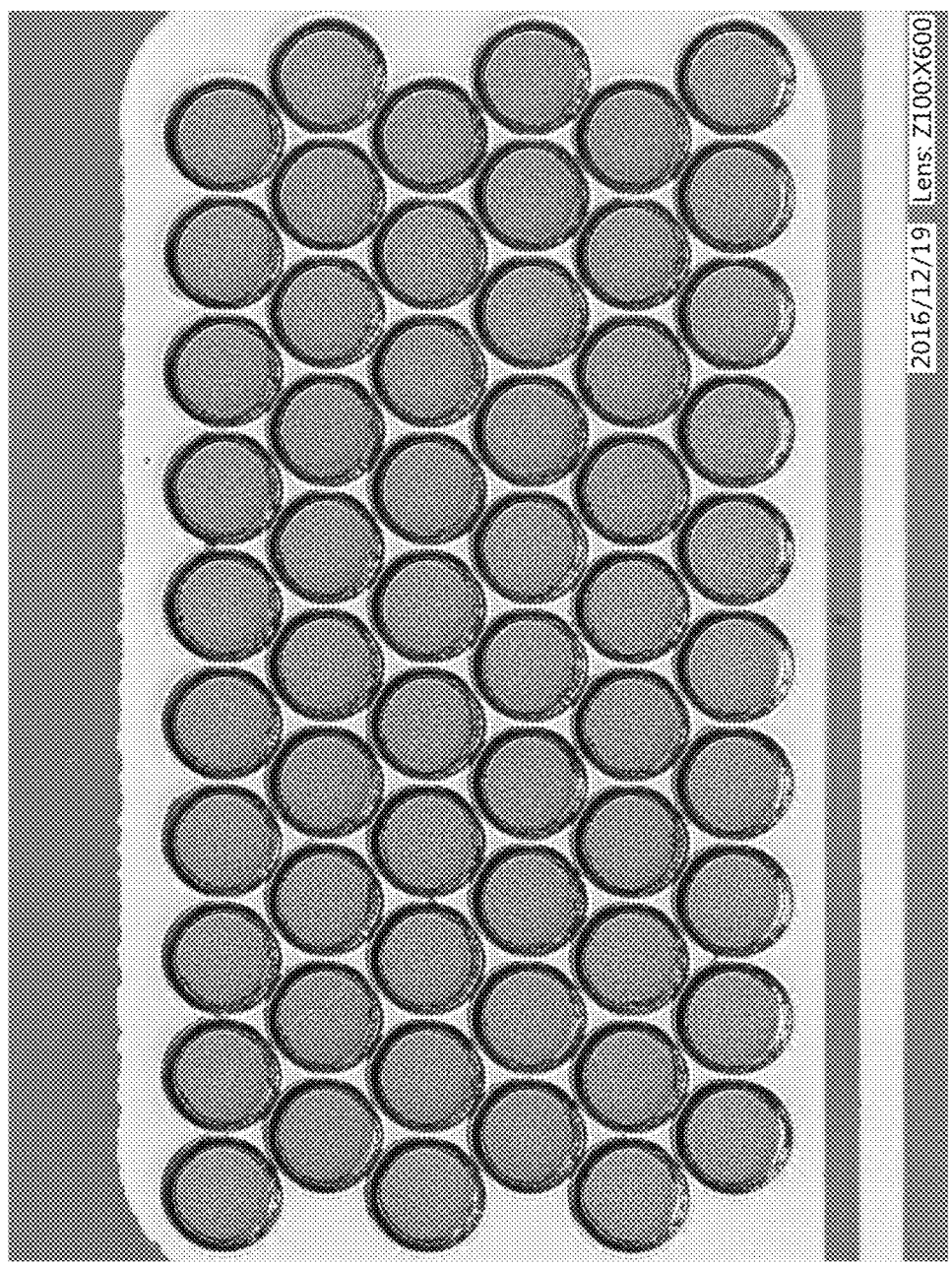
Figure 40:
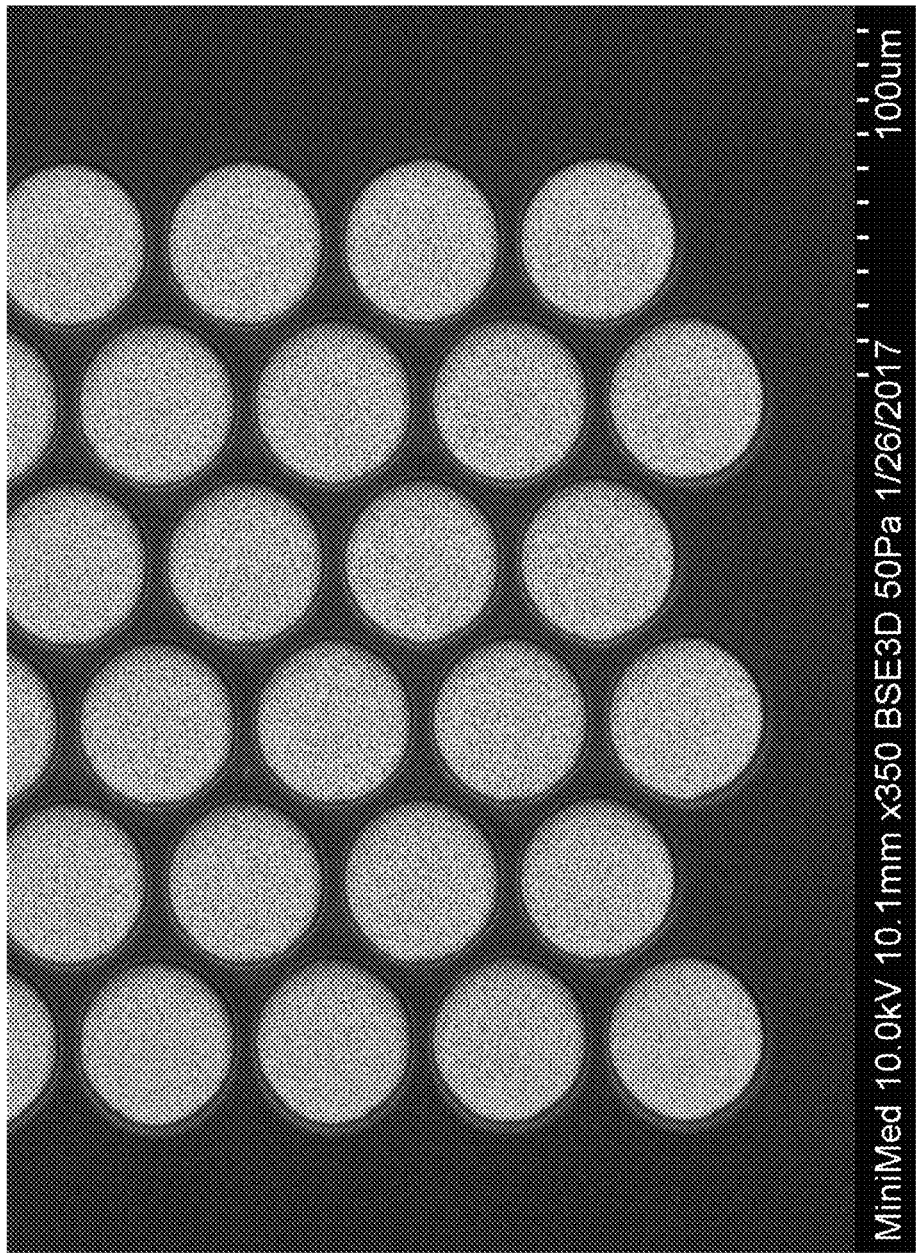
Figure 41:
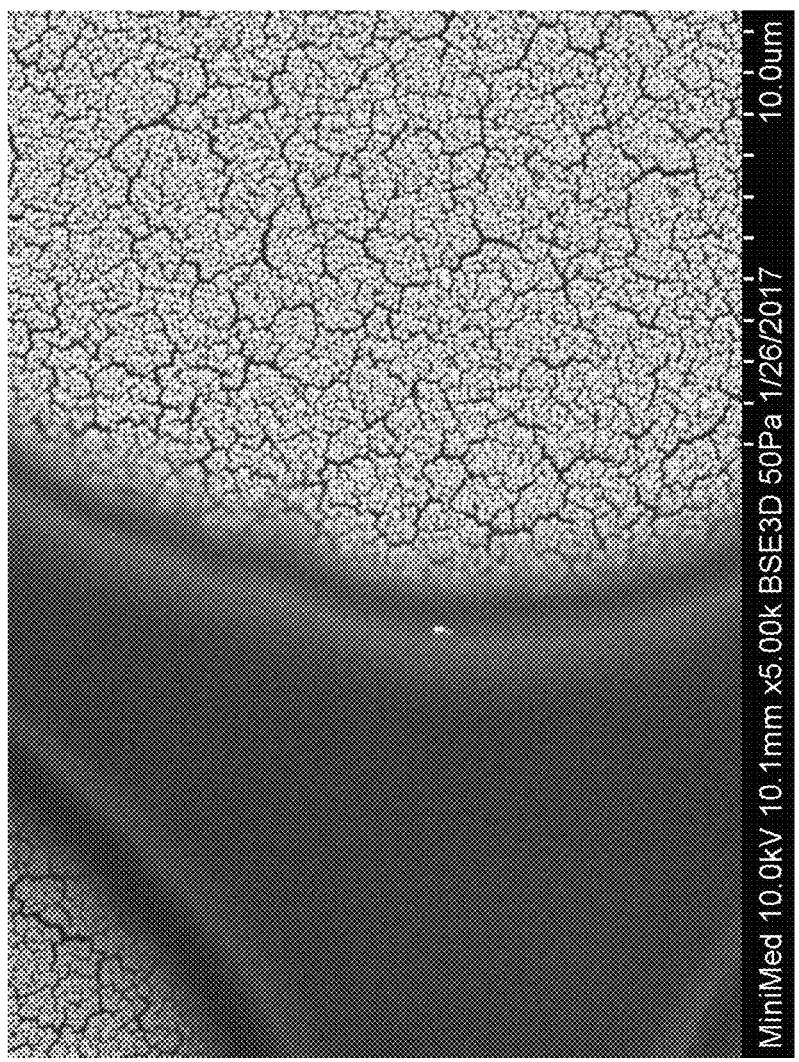
Figure 42:
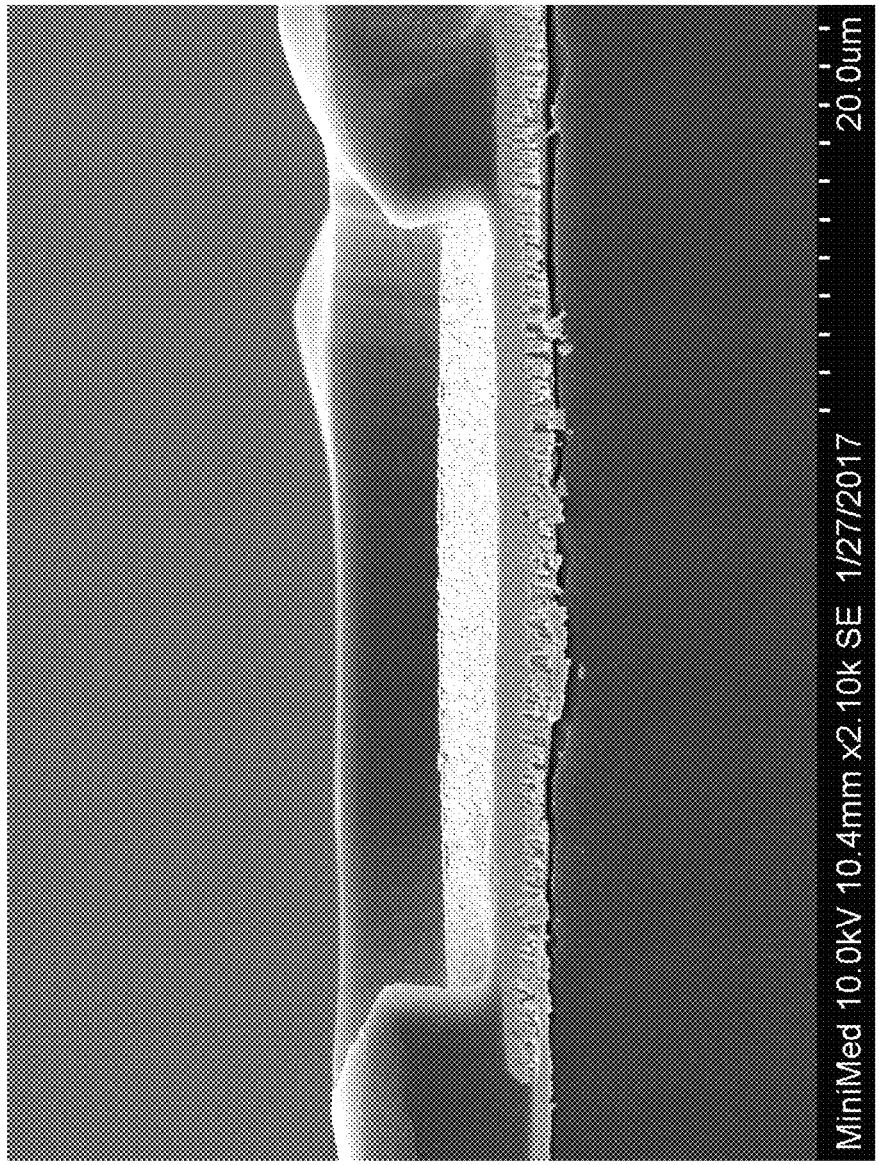
Figure 43:
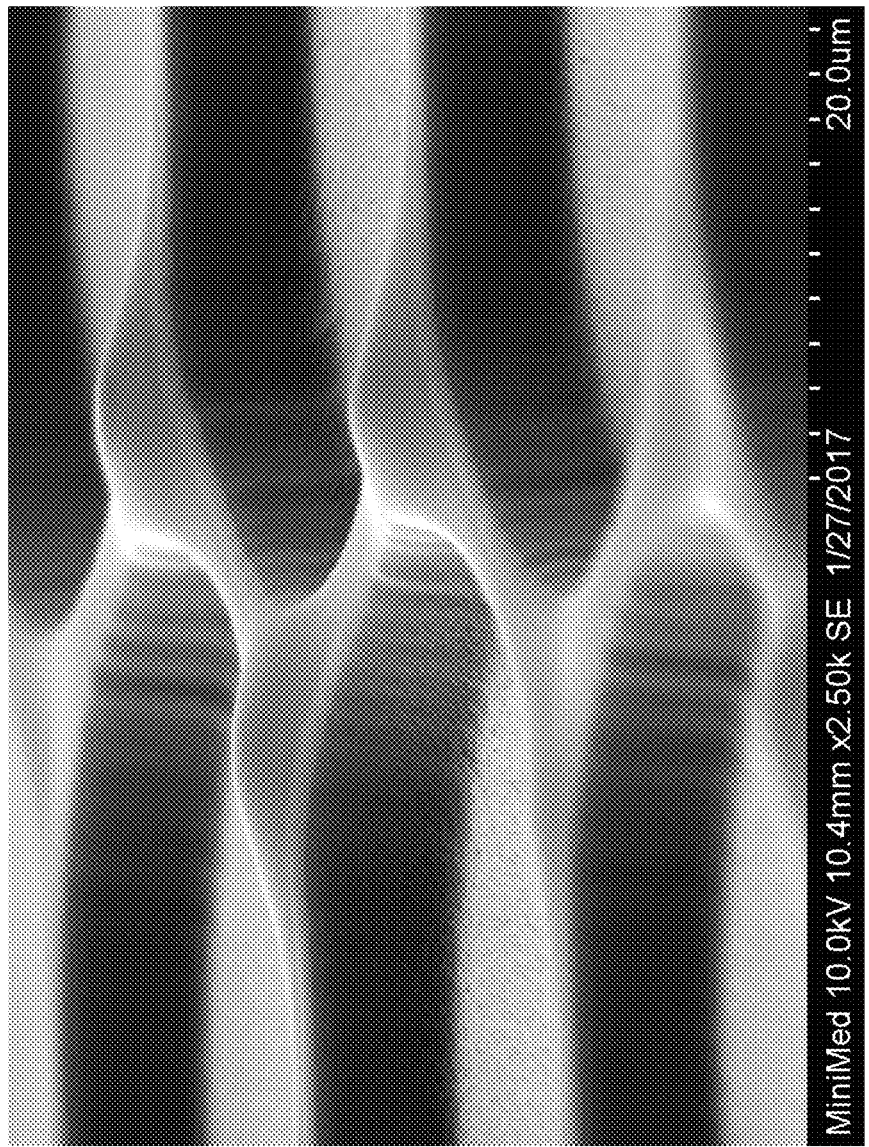
Figure 44:
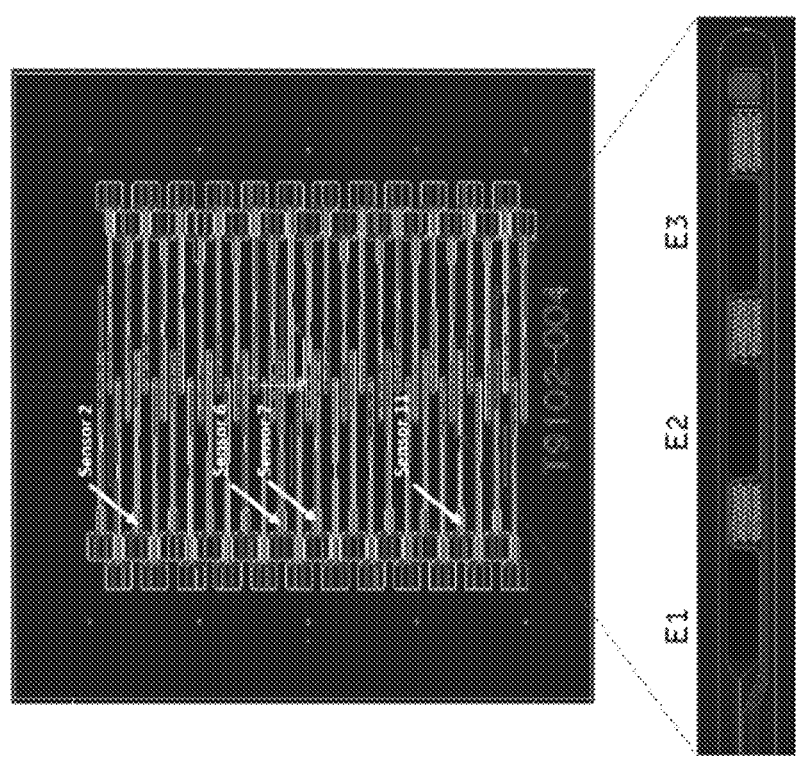
Figure 46A:
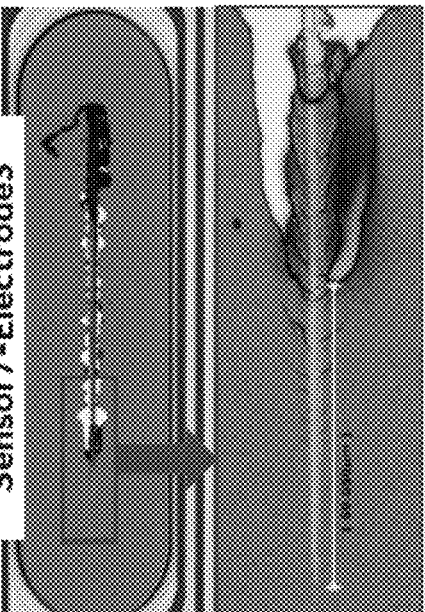
Figure 46B:
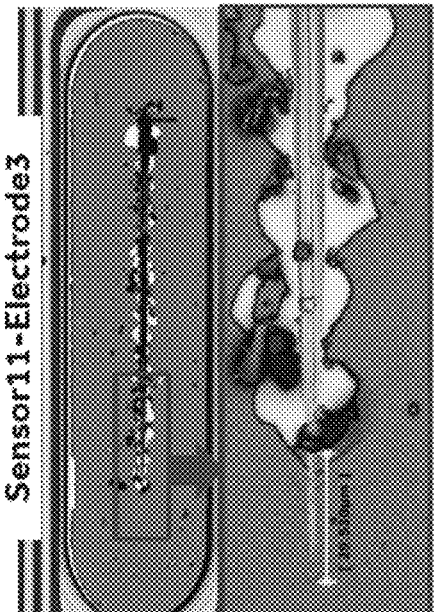
Figure 46C:
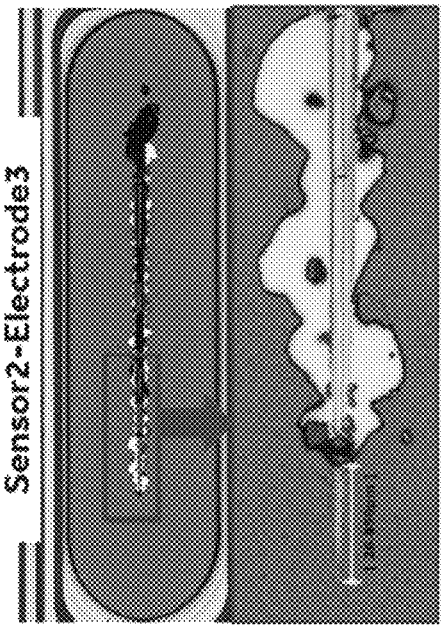
Figure 46D:
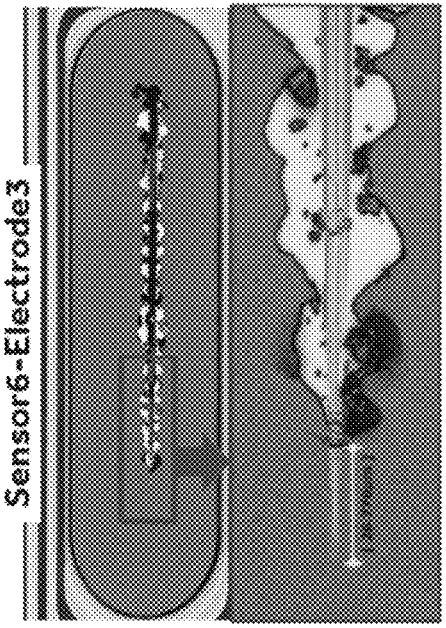
Figure 47A:
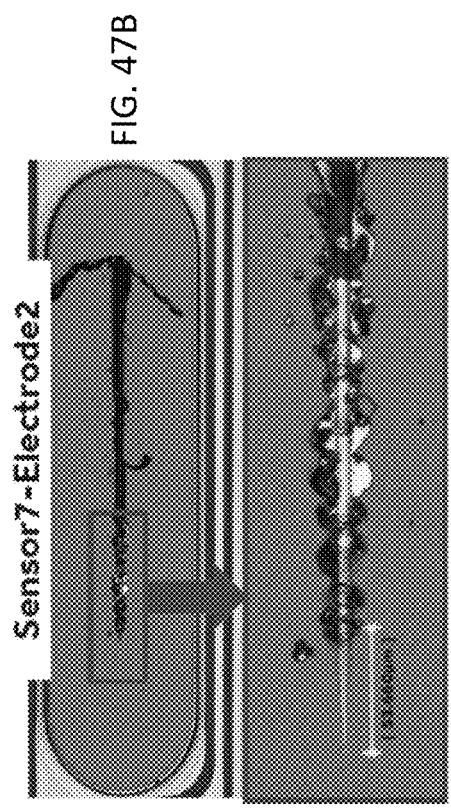
Figure 47B:
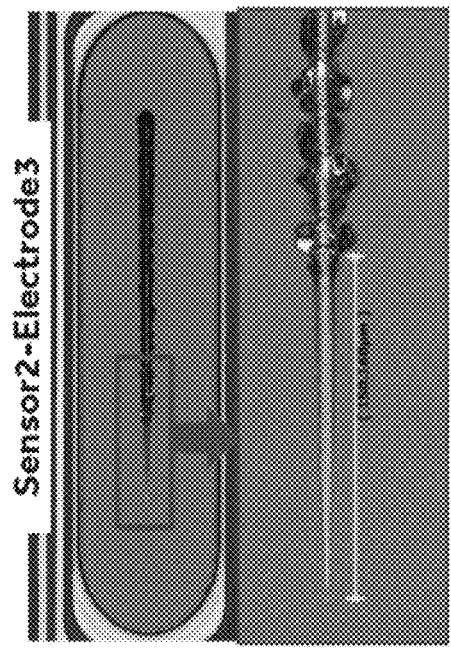
Figure 47C:
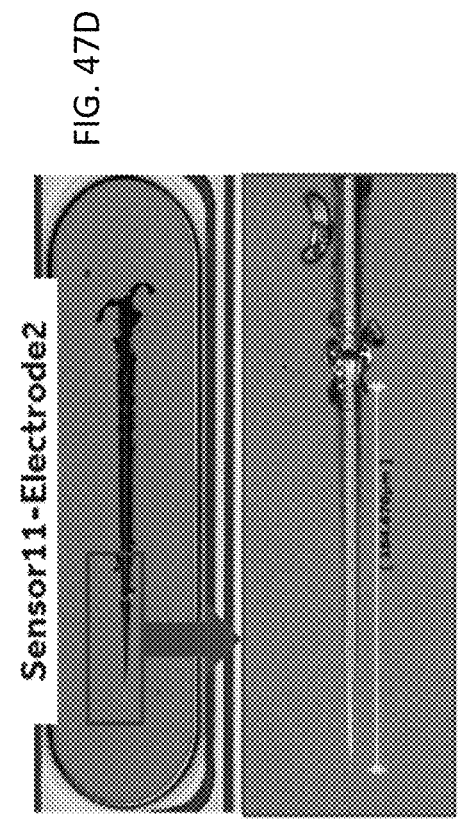
Figure 47D:
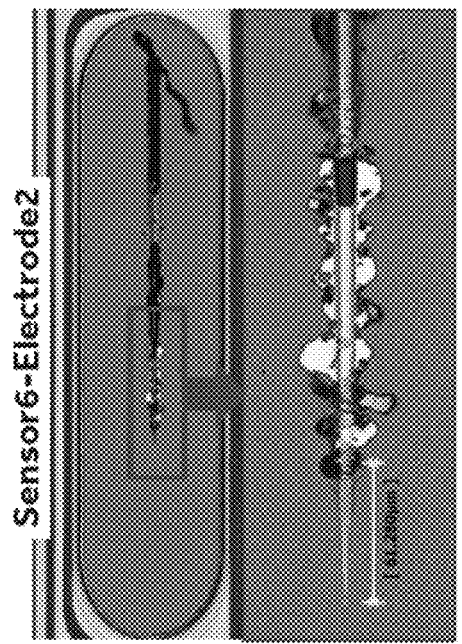
Figure 48A:
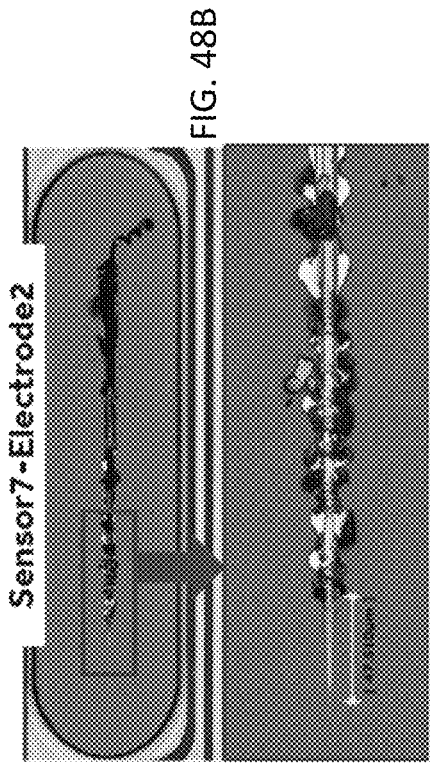
Figure 48B:
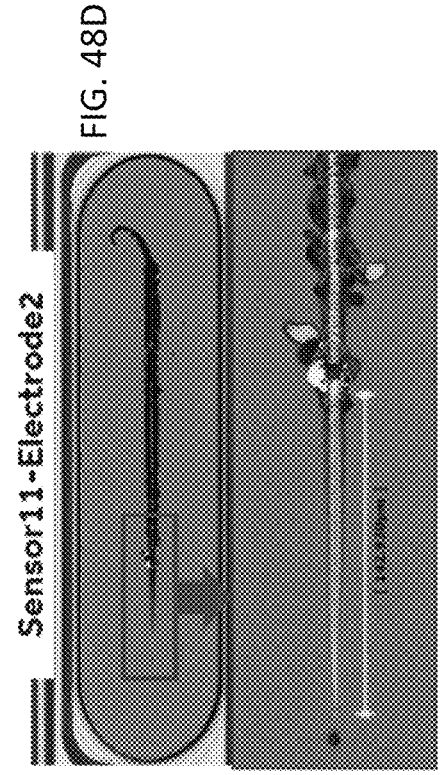
Figure 48C:
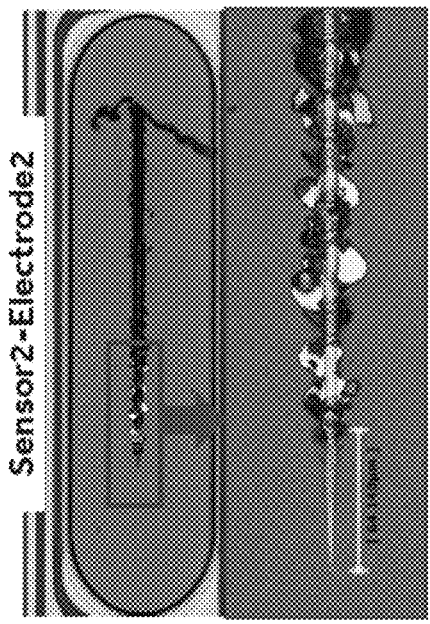
Figure 48D:
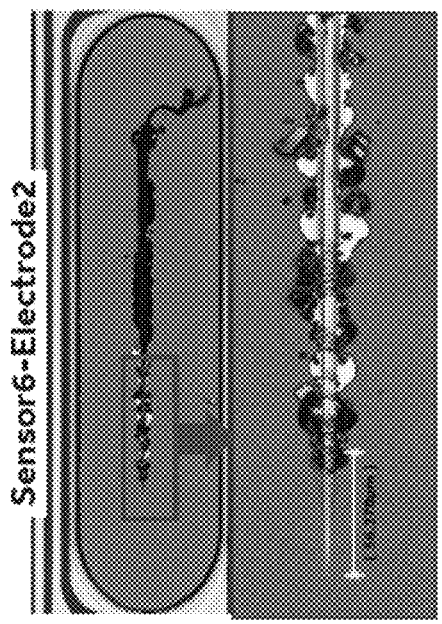
Figure 49B:
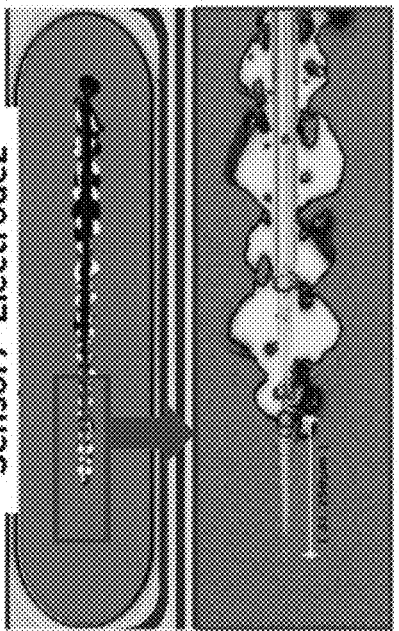
Figure 49D:
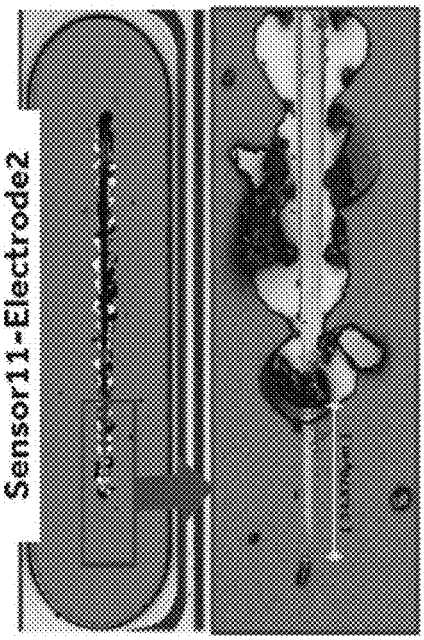
Figure 49A:
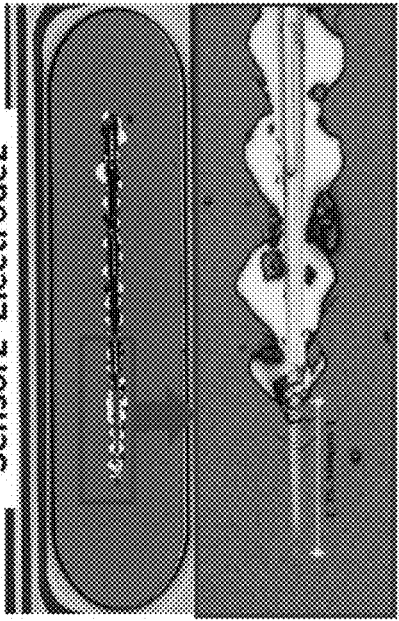
Figure 49C:
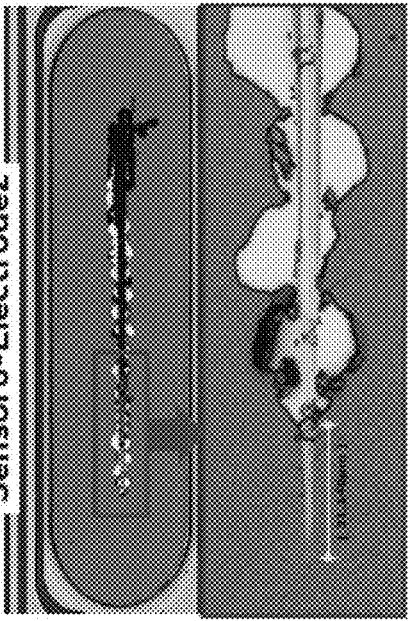
Figure 50A:
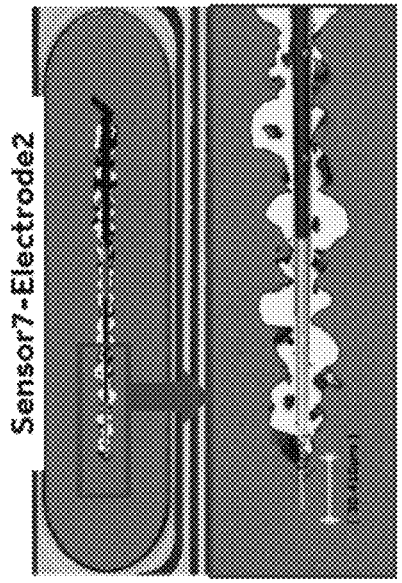
Figure 50B:
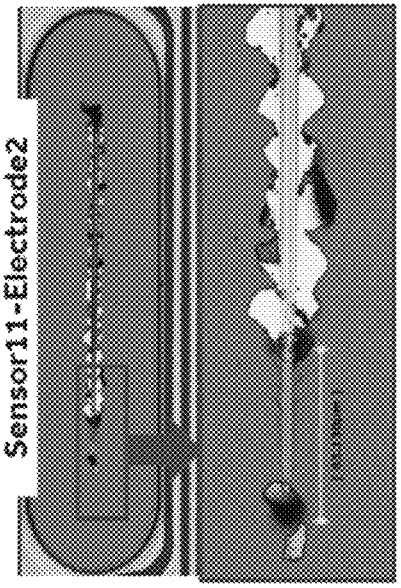
Figure 50C:
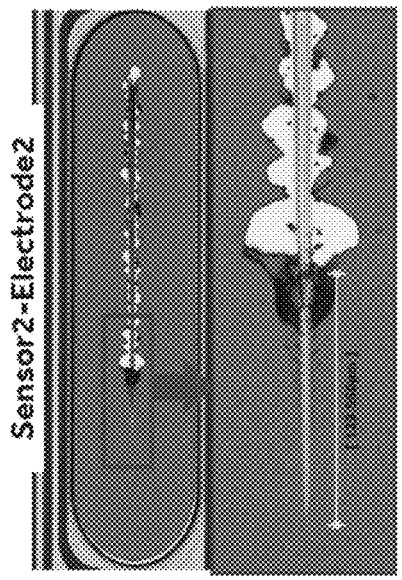
Figure 50D:
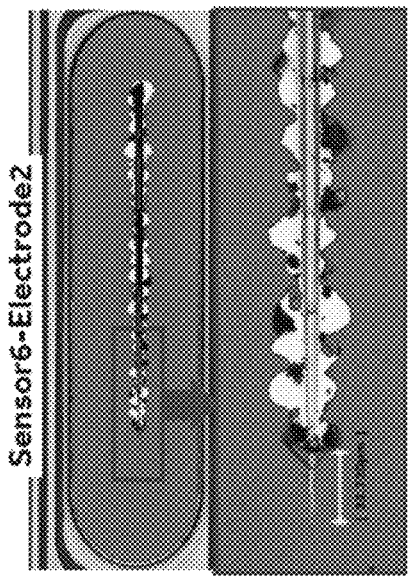
Figure 51A:
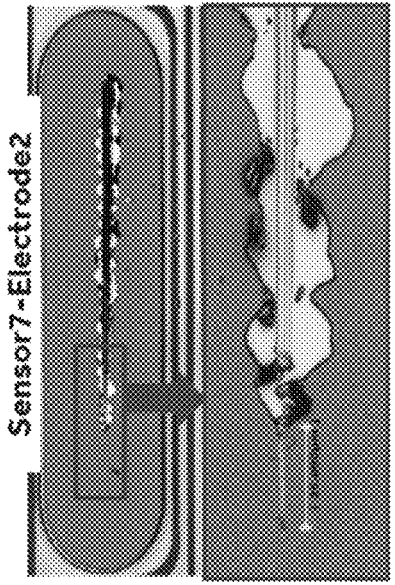
Figure 51C:
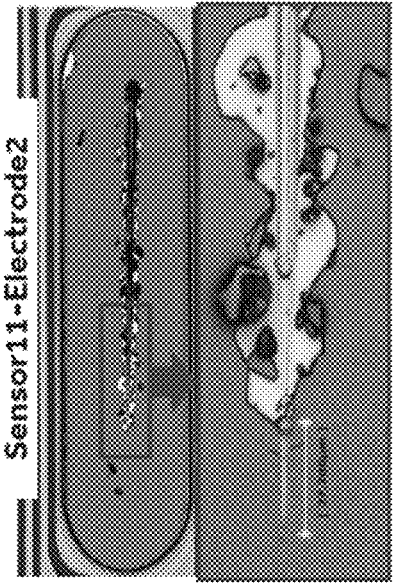
Figure 51B:
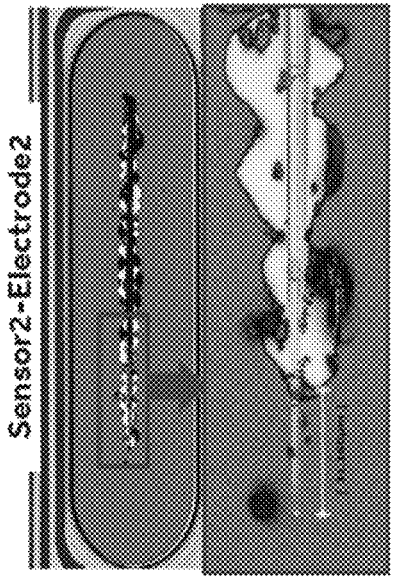
Figure 51D:
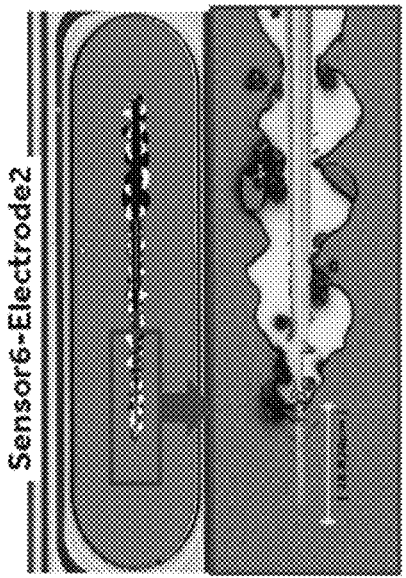
Figure 54:
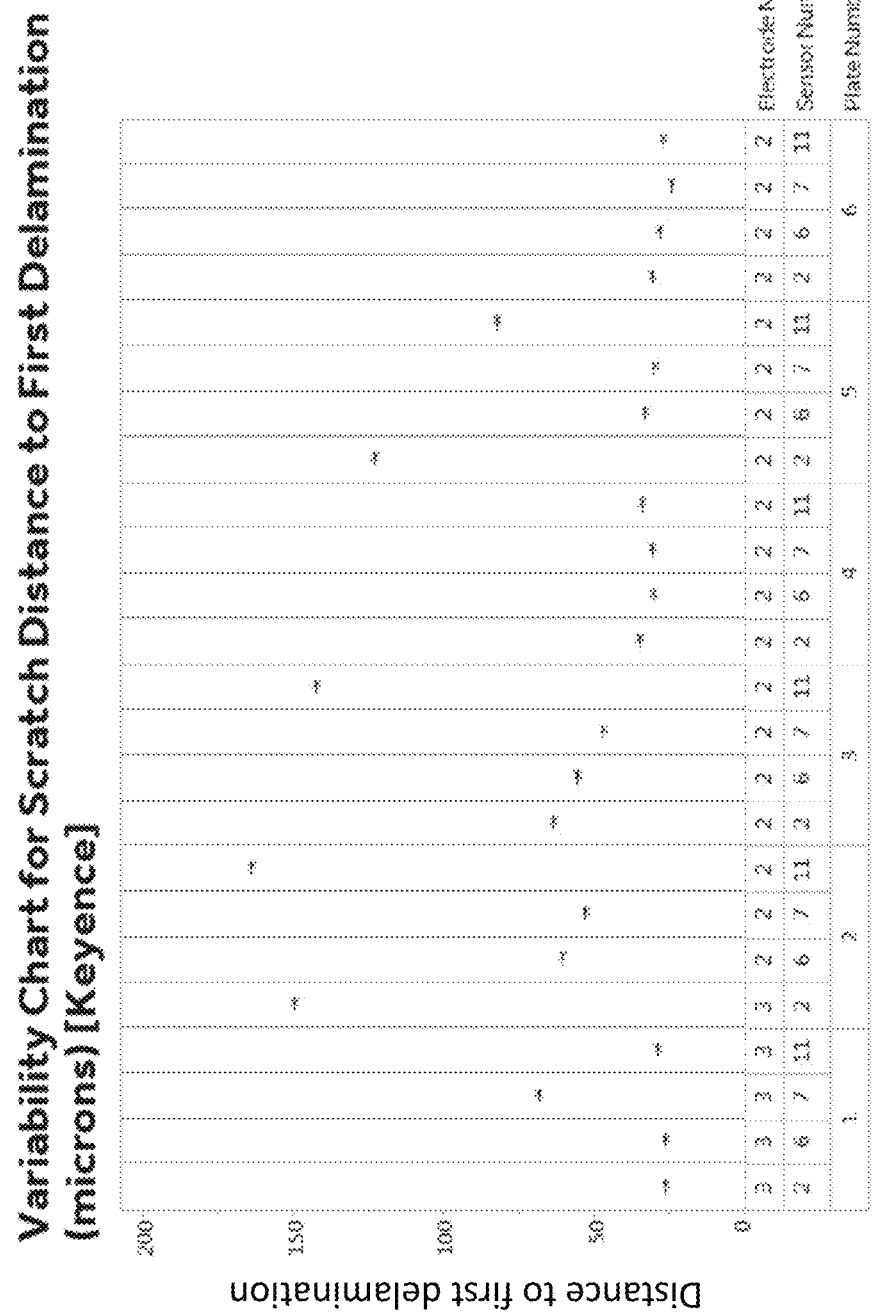
Figure 55:
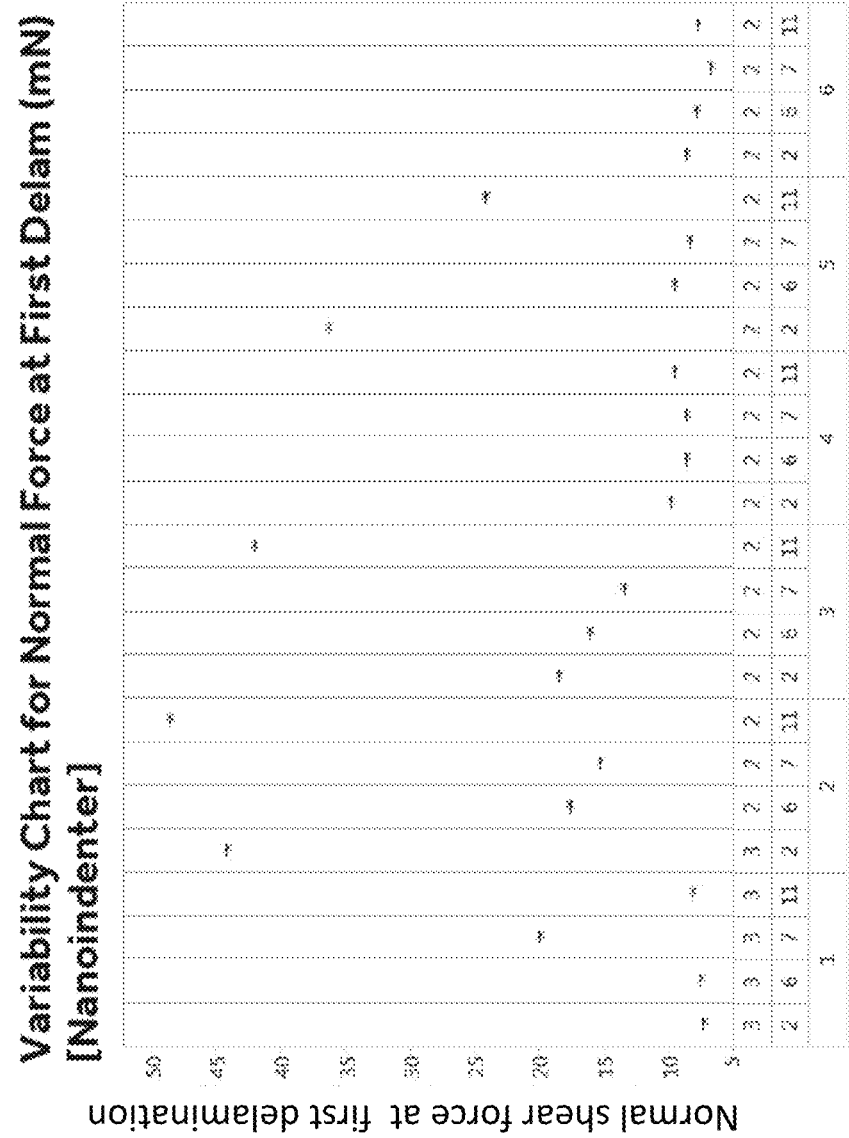
Figure 56:
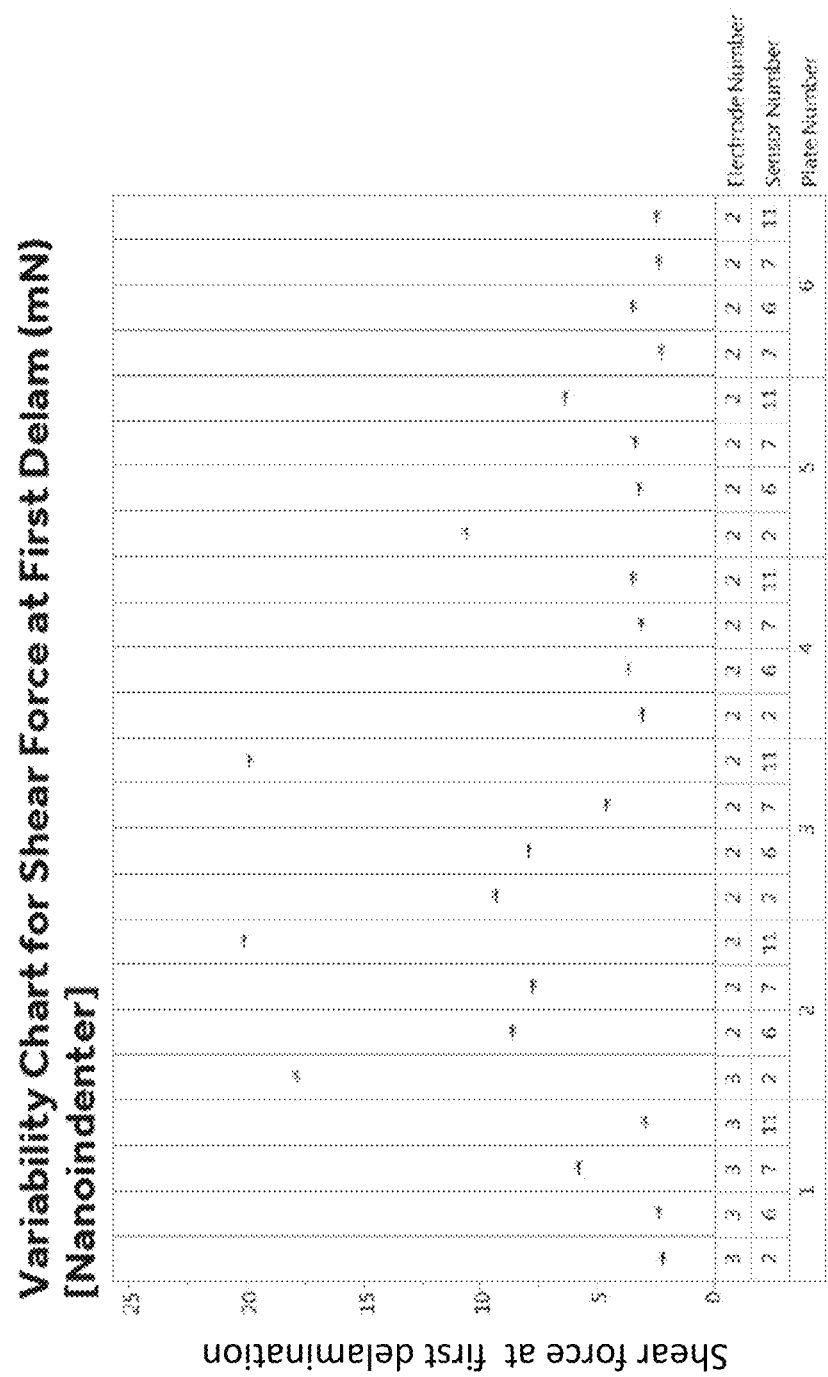
Figures 57A, 57B:
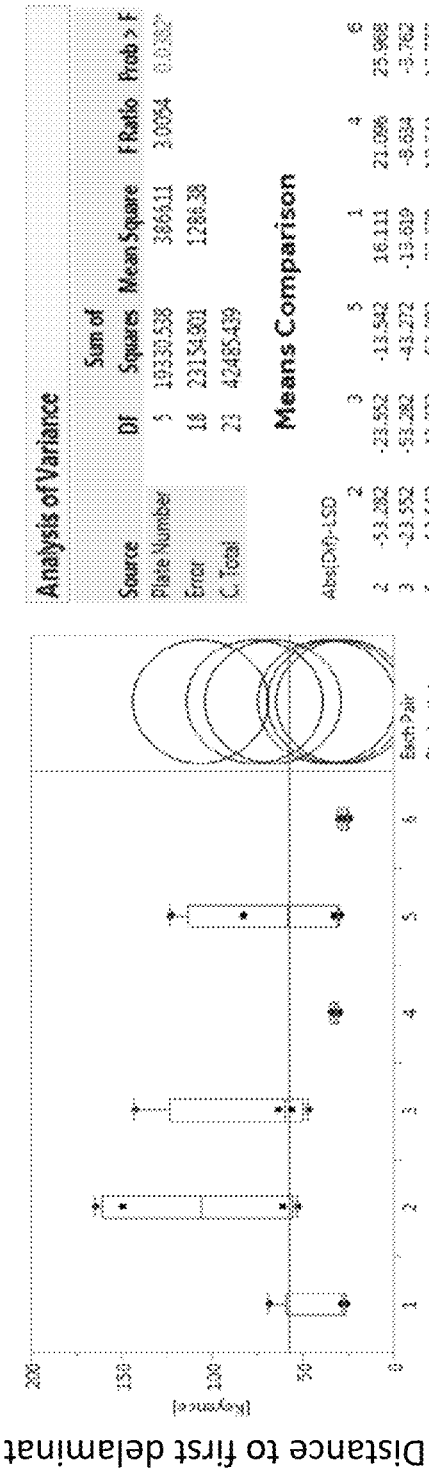
FIG. 57A and FIG. 57B illustrate analysis of variance for scratch distance to first delamination showing there is a statistical distance between plate number.
Figures 58A, 58B:
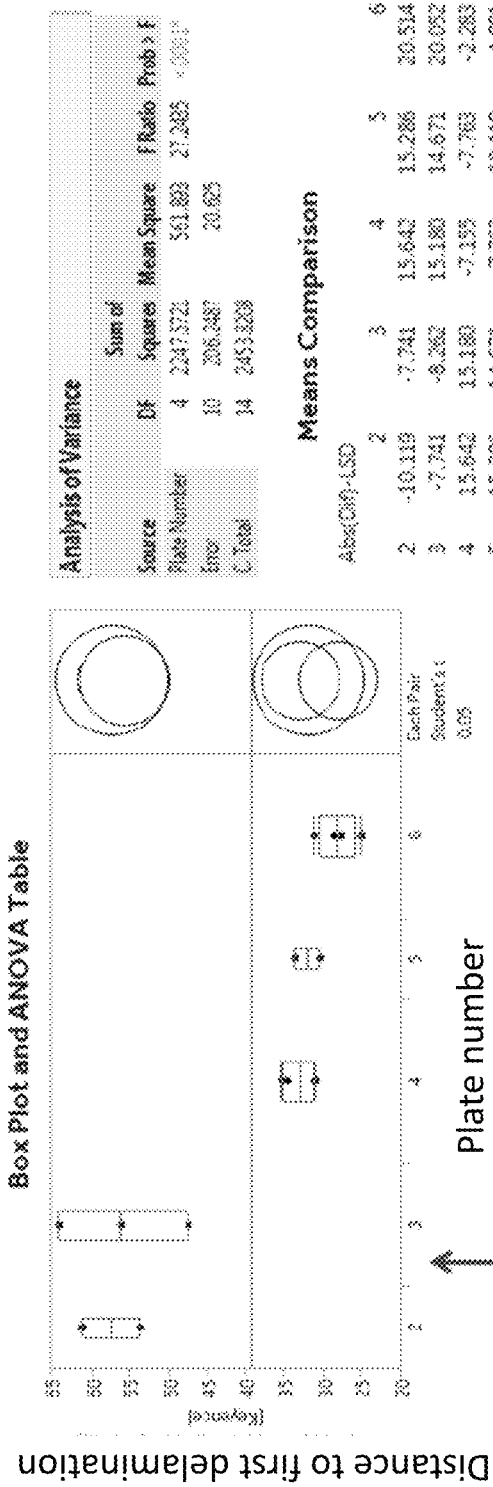
Figure 59:
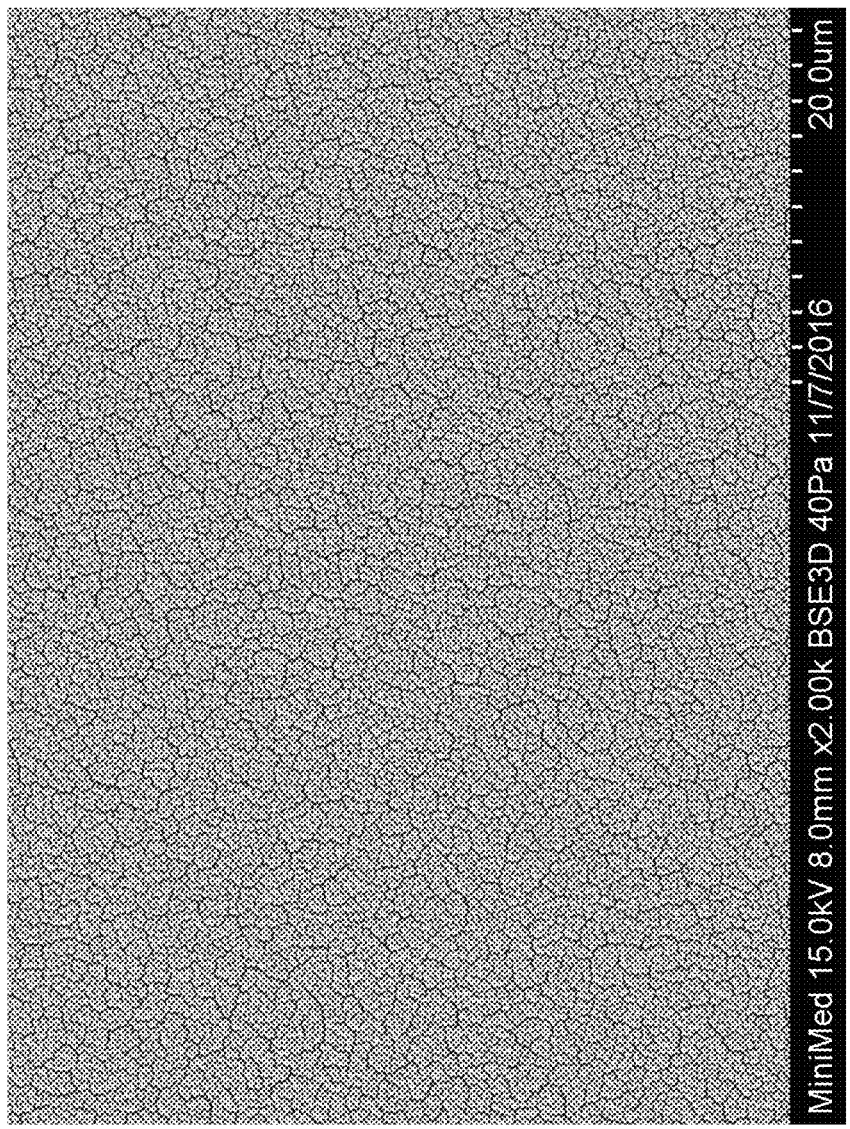
Figure 60:
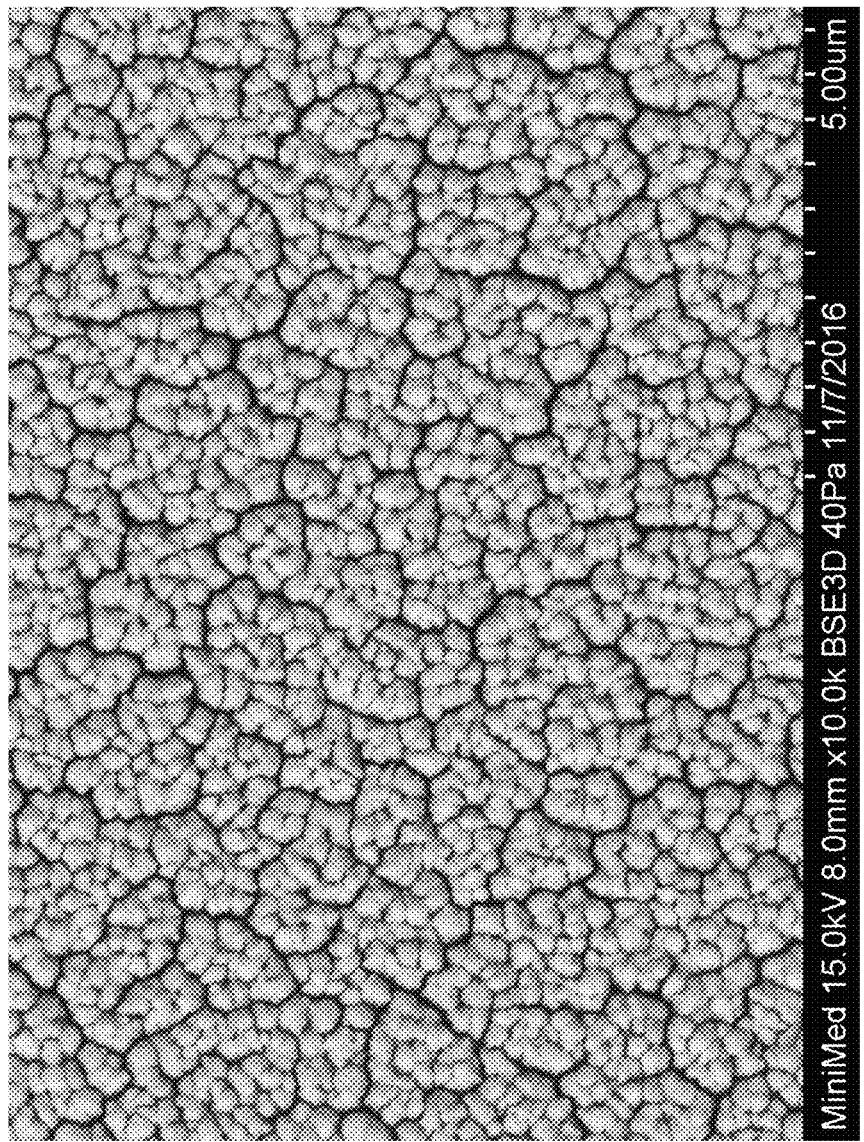
Figure 61:
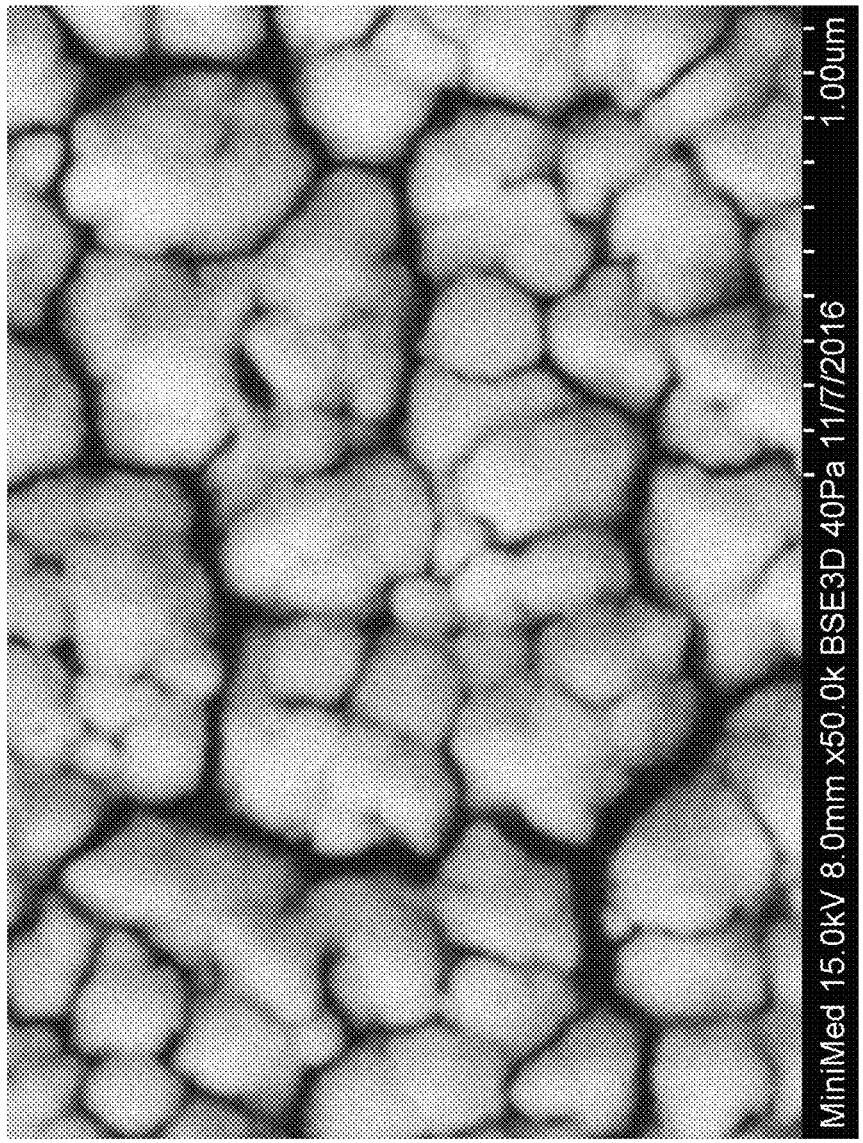
Figure 62:
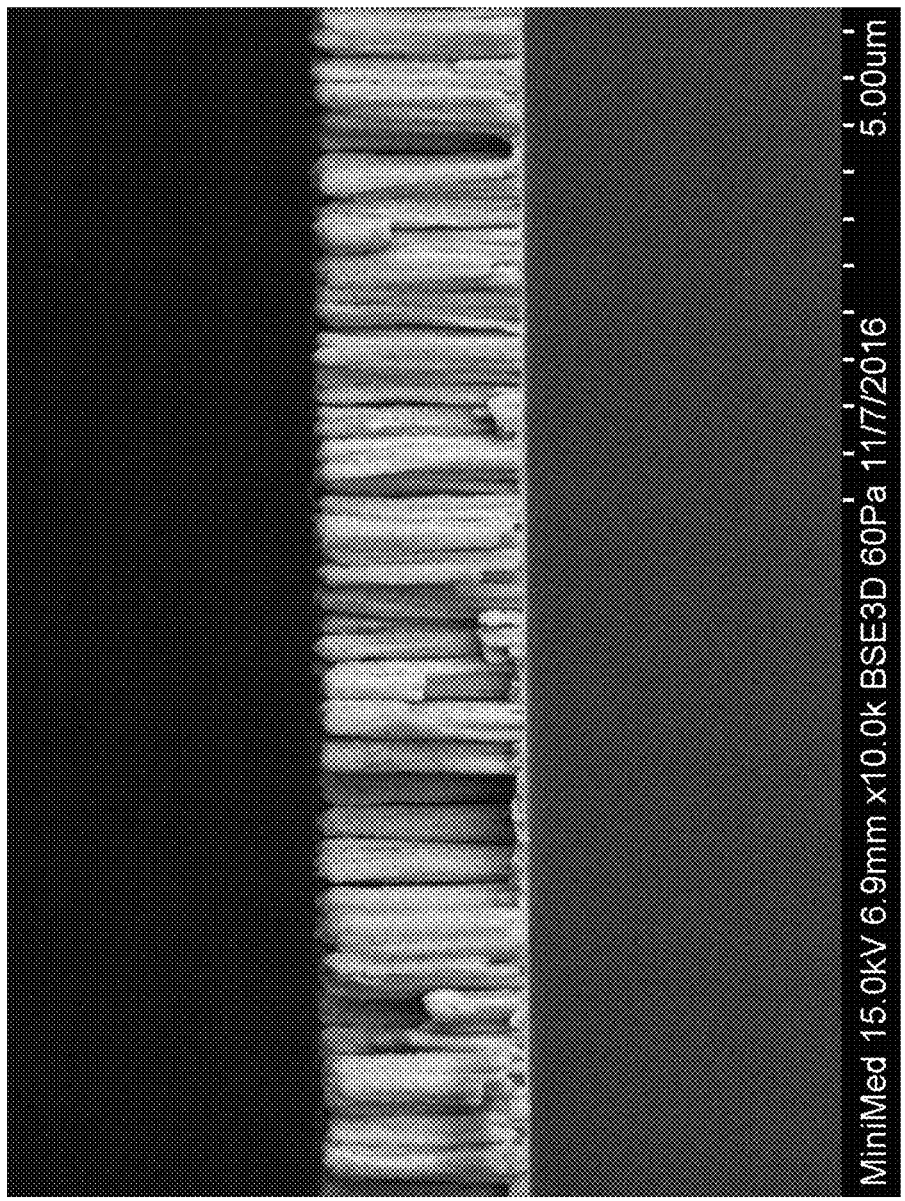
Figure 63:
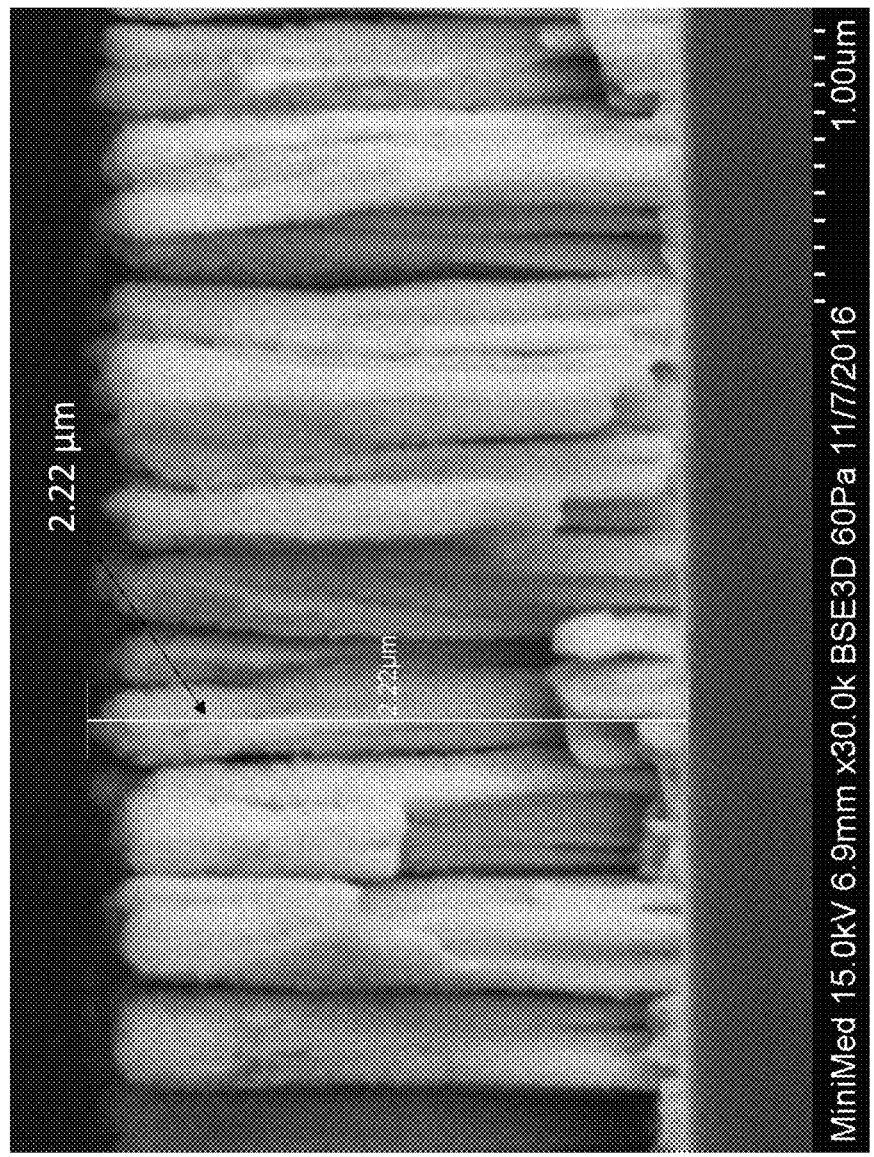

FIG. 34 shows sensor current, cal factor, and glucose as a function of time for sensors comprising Pt pillars (Pt pillar SAR=95) and nominal H1 sensors implanted in a dog. The data from measurements of 6 devices and using 2 dogs show comparable performance in Isig, Cal Factor and MARD for the Pt pillar devices and the nominal H1 sensors. This data evidences that Pt pillar sensors not require such a high SAR, enabling more uniform film deposition as compared to electroplated Pt and reduction in material cost and deposition time (a 60% lower SAR corresponds a 60% reduction in material cost and deposition time).

Example 8: Pig Testing (in House Clinical)

FIG. 35-38 present results of pig in-vivo experiments using sensors with Pt pillars as compared to Electroplated Pt. For the PIG trial, two groups of B2B sensor were used to obtain the data in FIGS. 35-38.

Group 1: PiPt95 & EpPt95 (n=4); flex1=sputtered Pt; flex2=electroplated Pt; SAR=95.

Group 2: PiPt250 & EpPt250 (n=10); flex1=sputtered Pt; flex2=electroplated Pt; SAR=250.

The results show the sputtered Pt sensor performed equivalently for both low and high SAR (i.e., the overall performance is similar among electroplated and sputtered Pt sensors, for both SAR 95 and SAR 250). Specifically, the data for day 1 (FIG. 38) shows comparable results for the electroplated and sputtered Pt sensor. Furthermore, the data shows no obvious change in 8 kHz imaginary impedance on sensitivity loss sensors.

Example 8: Pt Pillars Patterning Below Polyimide Insulation

FIGS. 39-43 are images of a novel implementation of pillars below & before the manufacturing process for the polyimide insulation layer in the sensors. Conventionally, the Pt pillars had been implemented above & after the manufacturing process for the polyimide insulation.

Example 9: Scratch Testing

FIGS. 44-58 illustrate scratch testing of Pt Pillars, and present results on adhesion testing performed to measure adhesion (until the point of failure) of the Pt Pillars to the underlying Gold electrode surface There is a need for a technique to quantify the adhesion strength between sputtered porous platinum and the trace metal layers of the H1 sensor substrates. Platinum black is electroplated onto a gold surface in conventional sensors. This Pt to Au interface cannot be evaluated for adhesion with current test methods. Delamination of platinum from gold is sometimes seen during downstream processes. Scratch testing for adhesion of Pt to Au allows characterization pre-plating treatments.

In addition, scratch test enables evaluation of new materials as possible replacements to platinum black.

In one or more embodiments, scratch testing is performed on the platinum layer to measure adhesion between the platinum and gold surface.

FIGS. 44-58 illustrate scratch testing of Pt Pillars, and present results on adhesion testing performed to measure adhesion (until the point of failure) of the Pt Pillars to the underlying Gold electrode surface. Adhesion between the different plates with sensors of varying thicknesses and processing conditions for sputtered porous platinum were evaluated by performing nano-scratch testing.

There are 2 groups (3 plates each) with sensors of varying thicknesses and processing conditions for sputtered porous platinum. For each plate, adhesion of the sputtered platinum on the counter electrodes of sensors 2, 6, 7, and 11 is evaluated (Group #1: Plate1, Plate2, and Plate3; Group #2: Plate4, Plate5, and Plate6). Scratch testing for plates #1-#6 was conducted on 1 out of 3 electrodes within sensors 2, 6, 7 and 11.

The electrodes that were chosen for scratch testing were as shown in Table 7

| Plate# | Sensor # | | | |
| --- | --- | --- | --- | --- |
| | 2 | 6 | 7 | 11 |
| 1 | Electrode3 | Electrode3 | Electrode3 | Electrode3 |
| 2 | Electrode3 | Electrode2 | Electrode2 | Electrode2 |
| 3 | Electrode2 | Electrode2 | Electrode2 | Electrode2 |
| 4 | Electrode2 | Electrode2 | Electrode2 | Electrode2 |
| 5 | Electrode2 | Electrode2 | Electrode2 | Electrode2 |
| 6 | Electrode2 | Electrode2 | Electrode2 | Electrode2 |

The electrode chosen for scratch testing within the sensor was not always the same throughout the testing.

Testing Apparatus

The low load head of the Micro Materials NanoTest system was used to perform scratch testing and Nano Test software was used for analyzing the scratch data. A 5 Micron Tip Indenter NT/CON090/005/020 was selected for testing the Pt—Au interface (SN: 16817e) All samples tested were subjected to the same testing parameters.

Example 10: Gold Structures

FIGS. 59-63 illustrate the same highly organized nano/micro pillar structures comprising gold instead of Pt. The gold pillars mimic the results observed for Platinum pillars.

The results evidence that the pillar structures may comprise metal compositions including all metals that can be sputtered. Thus, the present disclosure describes a composition of matter, comprising a base substrate; and pillars, towers, or columns disposed on the base substrate, wherein the pillars, towers, or columns each comprise a sputtered metal composition, have a height up to 10 micrometers, and have a diameter or width in a range of 1 nanometer-1000 nanometers. In some embodiments, the pillars, towers, or columns have a height in a range of 500 nm-4 micrometers and a diameter or width of 50 nm-200 nm. In other embodiments, the pillars, towers, or columns have a height in a range of 2 micrometers-4 micrometers and a diameter or width of 100 nm-900 nm. In one or more examples, the heights of the pillars, towers, or columns do not vary by more than 25% or 10% and/or the electroactive surface has a SAR in a range of 0-500. In one or more embodiments, the heights of the pillars, towers, or columns have a variation within 25%, within 10%, or within 5% and/or the top surface including the tops of all the pillars, towers, or columns has a SAR in a range of 0-500.

Example 11: Two Dimensional and Three Dimensional Structures

The pillars disclosed herein can form two dimensional or three dimensional structures. The pillars may be disposed, coated or grown on a non-planar base substrate or on a two dimensional or three dimensional structure. In one or more embodiments, the pillars are disposed on the surface of a cylinder, sphere, or other non planar surface. Thus, the pillars can be utilized with non-planar electrodes such as the leads in cardiac or neural electrodes.

Example 12: Full Electrical Circuits Formed from the Pillar Architectures

Conventional electrodes in sensor electrode configurations comprise an electroactive surface on an underlying metal comprising electrical traces and contact pads for connecting the electroactive surface to an external circuit or other parts of the sensor. Typically, the underlying metal comprises a composition (e.g., Au) that is different from the composition of the electroactive surface (e.g., Pt). fabricated from a different material from the pillars. One or more embodiments of the present invention do not require the underlying metal having the different metal composition. In one or more embodiments, a full electrical circuit (for interfacing with the sensor) is formed from/in the pillar structure. In one or more embodiments, the pillars include an electrical trace and electrical contact in operable contact with the sensor apparatus.

Furthermore, metal pillars can be used to make flexible electrodes and circuits because the region between the pillars can bend. Bulk material of the same thickness would result in cracks, delamination, etc., when flexed.

Example 13: Further Device Applications

Further medical applications include using the pillar structure as the electroactive surface of a cardiac lead or neural electrode.

However, the pillar architecture is useful in a variety of devices. Further implementations include, but are not limited to, using the pillar architecture as an electrode in a battery or solar cell, or as a catalyst layer (e.g., in a fuel cell). In one example, an electrode comprises the pillar architecture wherein the pillar architecture interfaces the electrode with an electrolyte. In another example. In another example, the electrode comprises the pillar architecture wherein the pillar architecture interfaces the electrode with another component in the device. In yet another example, the catalyst layer comprises the pillar architecture wherein the pillar architecture interfaces the catalyst layer with the catalyst.

Example 14: Composition of Matter Fabrication

Figure 64:
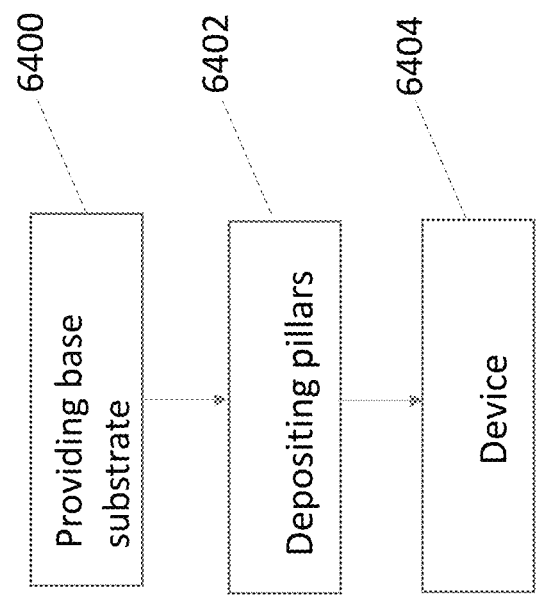
FIG. 64 is a flowchart illustrating a method of making a composition of matter.

FIG. 64 is a flowchart illustrating a method of making a composition of matter.

The method comprises the following steps (referring also to FIG. 8B and FIGS. 9A-9G).

Block 6400 represents providing a base substrate 902.

Block 6402 represents disposing pillars 904 on the base substrate 902, wherein the pillars 904 each comprise a sputtered metal composition 906, have a height 908 up to 10 micrometers, and have a diameter 910 in a range of 1 nanometer-1000 nanometers.

The composition of matter may be embodied in many ways, including, but not limited to, one or any combination of the following embodiments 1-5 listed below (unless indicated otherwise).

1. The heights of the pillars having a variation within 25%.

2. The composition of matter wherein a surface 912 of the pillars has a SAR in a range of 0-500.

3. The composition of matter wherein the metal composition 906 comprises at least one metal selected from platinum, gold, silver, copper, titanium, chromium, and iridium.

4. The composition of matter of embodiment 3, wherein the metal composition 906 comprises metal combined with a ceramic or a nitride.

5. The composition of matter wherein the pillars 904 are coated and/or grown on a two dimensional or three dimensional structure (e.g., on the base substrate comprising a two dimensional or three dimensional structure).

Block 6404 represents optionally disposing the composition of matter formed in Blocks 6400-6402 in a device such as, but not limited to, a sensor electrode configuration (e.g., as illustrated in FIG. 2) or in an electrode or catalyst layer, a fuel cell, or a solar cell.

The device may be embodied in many ways, including, but not limited to, the following embodiments listed below.

1. The sensor electrode configuration comprising a full electrical circuit formed from the pillars 904.

2. The sensor electrode configuration (e.g., of embodiment 1 or otherwise) wherein an electroactive surface 914 of the pillars 902 outputs a stimulus signal or receives a recording signal.

3. The sensor electrode configuration 450 of embodiment 2, wherein the electroactive surface 914 generates an electrochemical signal (e.g. Isig).

4. An electrode or catalyst layer comprising the composition of matter formed after Blocks 6400-6402 (e.g., composition of matter of one or any combination of embodiments 1-4 in Block 6402) or embodiment 1 in Block 6404.

5. The electrode of embodiment 4, wherein the electrode is a non-planar electrode such as a cardiac lead or neural electrode.

6. A flexible electrode and/or circuit comprising the composition of matter formed after Blocks 6400-6402 (e.g., composition of matter of one or any combination of embodiments 1-4 in Block 6402), wherein a region between the pillars can bend.

7. A fuel cell comprising the composition of matter formed after Blocks 6400-6402 (e.g., composition of one or any combination of embodiments 1-4 in Block 6402) or embodiment 1 in Block 6404.

8. A solar cell, solar panel, energy (e.g., solar) generating device, energy (e.g., solar energy) harvesting device, energy (e.g., solar energy) collecting device, or energy storing device (e.g., battery) comprising the composition of matter formed after Blocks 6400-6402 (e.g., composition of matter of one or any combination of embodiments 1-4 in Block 6402) or embodiment 1 in Block 6404. In one or more examples, the pillars are used in the light capture and/or energy conversion layer/region or energy storage layer/region of the device.

Example 15: Analyte Sensor Fabrication

Figure 65:
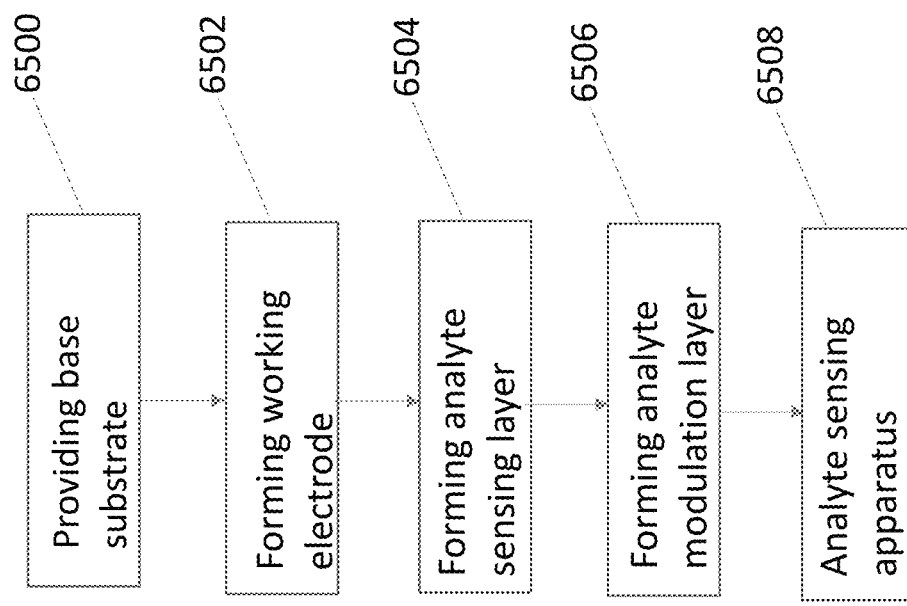
FIG. 65 is a flowchart illustrating a method of making an analyte sensing apparatus.

FIG. 65 is a flowchart illustrating a method of making an analyte sensor apparatus, e.g., as illustrated in FIG. 2.

The method comprises the following steps, referring also to FIG. 2, FIGS. 9A-9G, and FIG. 17C.

Block 6500 represents providing a base substrate 402, 902.

Block 6502 represents forming a working electrode WE on the base substrate 402, 902, wherein the working electrode WE 404 comprises pillars 904 comprising a metal composition 906, and the pillars 904 are formed from a process comprising depositing the metal composition 906 using sputtering so that the pillars 904 have a height 908 in a range up to 10 micrometers and a width 910 in a range of 1 nanometer-1000 micrometers, and the pillars 904 form an electroactive surface 914 of the electrode 404.

In one or more examples, the step comprises forming a mask on a surface of the base substrate, wherein the mask comprises openings exposing portions of the surface of the base substrate; sputter depositing the metal composition onto the mask and onto the portions of the surface exposed by the openings, so as to form the pillars extending through the openings; and removing the mask, leaving the pillars on the base substrate.

In yet further examples, forming the mask comprises depositing photoresist on surface of the substrate and photolithographically patterning the photoresist, and removing the mask comprises removing the photoresist using a photoresist lift-off process. In one or more embodiments, forming the mask comprises etching the substrate.

In one or more examples (e.g., referring to FIG. 5A), the sputter depositing comprises accelerating ionized gas particles 518 onto a target 520 comprising the metal composition 906 using an electric 524 and/or magnetic field 526 having a power. The ionized gas particles collide with the target and project material 522 comprising the metal composition onto the mask and the portions of the surface, and the power and a duration of the sputter depositing are selected so as to form the pillars having an SAR in a range of 0-500. In one or more further examples, the power and a duration of the sputter depositing are selected so as to form the working electrode having a surface area and impedance such that the sensor is at least as sensitive as a sensor fabricated using electroplated platinum. In yet further embodiments, a pressure of the ionized gas particles is in a range of 200 to 500 mTorr and a duration of the sputtering is in a range of 15-120 minutes.

In one or more embodiments, the step further comprises forming a polyimide insulation layer on the pillars after forming the pillars on the base substrate.

Block 6504 represents forming an analyte sensing layer 410 on or above the working electrode 404, wherein the analyte sensing layer 410 detectably alters the electrical current at the working electrode 404 in the presence of an analyte.

Block 6506 represents forming an analyte modulating layer 412 on or above the analyte sensing layer 410, wherein the analyte modulating layer 412 modulates the diffusion of analyte therethrough.

Block 6508 represents the end result, an analyte sensor apparatus 450, e.g., as illustrated in FIG. 2, comprising a base substrate 402, 902; and pillars 904 comprising a metal composition 906, wherein the pillars 904 are disposed on the base substrate 402 and form an electroactive surface 914 of a working electrode 404; an analyte sensing layer 410 disposed over the working electrode 404, wherein the analyte sensing layer 410 detectably alters the electrical current Isig at the working electrode 404 in the presence of an analyte; and an analyte modulating layer 412 disposed over the analyte sensing layer 410, wherein the analyte modulating layer 412 modulates the diffusion of analyte therethrough.

The analyte sensor apparatus 450 may be embodied in many ways, including, but not limited to, any of the following embodiments listed below or any combination of the embodiments 1-6 listed below.

1. The pillars 904 each having a height 908 in a range up to 10 micrometers and a diameter in a range of 1 nanometer-1000 nanometers, the heights 908 of the pillars having a variation within 25%, and the electroactive surface 914 having a SAR in a range of 0-500.

2. The pillars 904 having a spacing 916 (See FIG. 9A) that accommodates hydrogen peroxide so as to oxidize the hydrogen peroxide between the pillars 904 after an oxidoreductase enzyme in the analyte sensing layer 410 reacts with glucose to produce the hydrogen peroxide.

3. The metal composition 906 comprising at least one metal selected from platinum, gold, silver, copper, titanium, chromium, and iridium.

4. The metal composition 906 comprising a metal combined with a ceramic and/or a nitride.

5. The analyte sensor apparatus 450 further comprising a polyimide insulation layer (e.g., 406), wherein the pillars 904 are between the polyimide insulation layer and the base substrate.

6. The analyte sensor apparatus wherein the pillars 904 include an electrical trace and electrical contact in operable contact with the sensor apparatus 450.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

REFERENCES

The following references are incorporated by reference herein.

1. A Comprehensive Review of Glucose Biosensors Based on Nanostructured Metal-Oxides *Sensors* 2010, 10, 4855-4886; doi:10.3390/s100504855
2. High utilization of Pt nanocatalysts fabricated using a high-pressure sputtering technique, Journal of Power Sources 178 (2008) 547-553.
3. Hydrothermal Growth of Vertically Aligned ZnO Nanorods Using a Biocomposite Seed Layer of ZnO Nanoparticles, *Materials* 2013, 6, 3584-3597; doi:10.3390/ma6083584.
4. Nucleation and initial growth of platinum islands by plasma sputter Deposition, Surface and Coatings Technology 151-152 (2002) 122-127.
5. Plasma Sputtering Deposition of PEMFC Porous Carbon Platinum Electrodes, FUEL CELLS 08, 2008, No. 2, 81-86.
6. Characterization of porous Pt films deposited via sputtering, Applied Surface Science 282 (2013) 463-466.
7. Porous platinum electrodes derived from the reduction of sputtered platinum dioxide Journal of Applied Electrochemistry 29: 883-888, 1999.
8. Preparation and characterization of platinum black electrodes, JOURNAL OF MATERIALS SCIENCE 35 (2000) 3447-3457.
9. Strategies for the Fabrication of Porous Platinum Electrodes, *Adv. Mater.* 2011, 23, 4976-5008.

The invention claimed is:

1. A method of making an analyte sensor apparatus, the method comprising the steps of:
   providing a base substrate; and
   sputtering a metal composition onto the base substrate from a target, wherein;
      the target comprises the metal composition,
      the target is located off the base substrate, and
      the sputtering comprises:
         accelerating ionized gas particles onto the target using at least one of an electric or magnetic field, the ionized gas particles having a pressure greater than a threshold pressure and colliding with the target to project the metal composition onto the base substrate and into a pillar shape so that:
            the pillars have a height in a range up to 10 micrometers and a width in a range of 1 nanometer-1000 micrometers,
            the pillars consist essentially of the metal composition, and
            the pillars form an electroactive surface of electrode;
   forming an analyte sensing layer on the working electrode, wherein the analyte sensing layer detectably alters the electrical current at the working electrode in the presence of an analyte; and
   forming an analyte modulating layer on the analyte sensing layer, wherein the analyte modulating layer modulates the diffusion of analyte therethrough; and
   so that the analyte sensor apparatus is formed.

2. The method of claim 1, wherein the heights of the pillars have a variation within 25%.

3. The method of claim 1, wherein a surface of the pillars has a SAR in a range of 0-500.

4. The method of claim 1, wherein the metal composition comprises at least one metal selected from platinum, gold, silver, copper, titanium, chromium, and iridium.

5. The method of claim 4, wherein the metal composition comprises metal combined with a ceramic or a nitride.

6. The method of claim 1, wherein the pillars including the metal composition form an electroactive surface of the sensor electrode configuration.

7. The method of claim 6, comprising a full electrical circuit formed from the pillars, wherein the pillars including the metal composition form an electrical trace and an electrical contact for making an operable contact with a sensor apparatus.

8. The method of claim 7, wherein the electroactive surface outputs a stimulus signal or receives a recording signal.

9. The method of claim 6, wherein the electroactive surface generates an electrochemical signal.

10. The method of claim 1, wherein a region between the pillars can bend.

11. The method of claim 1, further comprising:
   forming a mask on a surface of the base substrate, wherein the mask comprises openings exposing portions of the surface of the base substrate;
   sputtering the metal composition onto the mask and onto the portions of the surface exposed by the openings, so as to form the pillars extending through the openings; and
   removing the mask, leaving the pillars on the base substrate.

12. The method of claim 11, wherein
   a power and a duration of the sputtering are selected so as to form the pillars having an SAR in a range of 0-500.

13. The method of claim 11, wherein
a power and a duration of the sputtering are selected so as to form the working electrode having a surface area and impedance such that the sensor is at least as sensitive as a sensor fabricated using electroplated platinum.

14. The method of claim 11, wherein
the pressure of the ionized gas particles is in a range of 200 to 500 mTorr and a duration of the sputtering is in a range of 15-120 minutes.

15. The method of claim 1, wherein the pillars extend from a non-planar surface of the base substrate.

* * * * *